US008853182B2

(12) United States Patent
Inoue et al.

(10) Patent No.: US 8,853,182 B2
(45) Date of Patent: Oct. 7, 2014

(54) CELL GROWTH INHIBITOR AND SCREENING METHOD THEREOF

(71) Applicant: The University of Tokyo, Tokyo (JP)

(72) Inventors: Satoshi Inoue, Tokyo (JP); Kenichi Takayama, Tokyo (JP)

(73) Assignee: The University of Tokyo, Tokyo (JP)

( * ) Notice: Subject to any disclaimer, the term of this patent is extended or adjusted under 35 U.S.C. 154(b) by 0 days.

(21) Appl. No.: 13/737,529

(22) Filed: Jan. 9, 2013

(65) Prior Publication Data

US 2013/0217750 A1 Aug. 22, 2013

Related U.S. Application Data

(63) Continuation-in-part of application No. 13/636,910, filed as application No. PCT/JP2011/057376 on Mar. 25, 2011.

(30) Foreign Application Priority Data

Mar. 26, 2010 (JP) ................................ 2010-072613

(51) Int. Cl.
*C12N 15/11* (2006.01)
*C12Q 1/68* (2006.01)
*A61K 31/713* (2006.01)
*C12N 15/113* (2010.01)

(52) U.S. Cl.
CPC ............ *A61K 31/713* (2013.01); *C12N 15/113* (2013.01); *C12N 2310/14* (2013.01)
USPC ......................................... 514/44 A; 435/6.1

(58) Field of Classification Search
None
See application file for complete search history.

(56) References Cited

U.S. PATENT DOCUMENTS

2003/0175736 A1 9/2003 Chinnaiyan et al.
2005/0246794 A1* 11/2005 Khvorova et al. ............ 800/286
2008/0113351 A1* 5/2008 Naito et al. ....................... 435/6
2008/0222741 A1 9/2008 Chinnaiyan
2009/0149403 A1 6/2009 MacLachlan et al.

FOREIGN PATENT DOCUMENTS

JP 2005-518522 A 6/2005
WO WO 2005116204 A1 * 12/2005

OTHER PUBLICATIONS

Sasaki et al, MEN epsilon/beta noncoding RNAs are essential for structural integrity of nuclear paraspeckles, Feb. 2009, PNAS, vol. 106, 8: 2525-2530.*
Suzuki et al., "Androgen receptor involvement in the progression of prostate cancer," Endocrine-Related Cancer, 10: 209-216 (2003).
Chen et al., "Molecular determinants of resistance to antiandrogen therapy," Nature Medicine, 10: 33-39 (2004).
Debes et al., "Mechanisms of Androgen-Refractory Prostate Cancer," New England Journal of Medicine, 351: 1488-1490 (2004).
Sun et al., "Adeno-associated virus-delivered short hairpin-structured RNA for androgen receptor gene silencing induces tumor eradication of prostate cancer xenografts in nude mice: a preclinical study," International Journal of Cancer, 126: 764-774 (2010).
Compagno et al., "SIRNA-Directed In Vivo Silencing of Androgen Receptor Inhibits the Growth of Castration-Resistant Prostate Carcinomas," PLoS One, 2: e1006 (2007).
Snoek et al., "In vivo Knockdown of the Androgen Receptor Results in Growth Inhibition and Regression of Well-Established, Castration-Resistant Prostate Tumors," Clinical Cancer Research, 15: 39-47 (2009).
Chinnadurai, "The Transcriptional Corepressor CtBP: A Foe of Multiple Tumor Suppressors," Cancer Research, 69: 731-734 (2009).
Nadauld et al., "Adenomatous Polyposis Coli Control of C-terminal Binding Protein-1 Stability Regulates Expression of Intestinal Retinol Dehydrogenases," Journal of Biological Chemistry, 281: 37828-37835 (2006).
Office Action issued in corresponding U.S. Appl. No. 13/636,910 dated May 13, 2013.

* cited by examiner

*Primary Examiner* — Tracy Vivlemore
*Assistant Examiner* — Kate Poliakova
(74) *Attorney, Agent, or Firm* — Morgan, Lewis & Bockius LLP

(57) ABSTRACT

An object is to provide a cell growth inhibitor also effective for androgen-independent prostate cancer. The present invention provides a cell growth inhibitor having, as an active ingredient, an expression inhibitor or function inhibitor of PSF.

10 Claims, 33 Drawing Sheets

Administration of siRNAs to Prostate Cancer Xenograft Model

CELL GROWTH INHIBITOR AND SCREENING METHOD THEREOF

A computer readable text file, entitled "SequenceListing.txt," created on or about Mar. 28, 2013 with a file size about 75 kb contains the sequence listing for this application and is hereby incorporated by reference in its entirety.

TECHNICAL FIELD

The present invention relates to a growth inhibitor of cells, such as prostate cancer cells, in which expression of a predetermined antisense RNA of a CTBP1 gene has been enhanced, a method of screening a cell growth inhibitor, and the like.

BACKGROUND ART

Prostate cancer is a cancer which manifests in men most frequently in Europe and United States. Also in Japan, with westernization of dietary habits and aging of population, the number of patients suffering from prostate cancer is increasing drastically. Methods used widely for the treatment of prostate cancer are surgical therapy including prostatectomy, chemotherapy with an anticancer agent, and radiation therapy. Surgical therapy is the first-line treatment, but when cancer is diagnosed as being in an advanced stage or when surgery cannot be selected because it is a recurrent cancer after surgery, a therapeutic method other than surgery is selected.

In general, proliferation of prostate cancer is stimulated by androgen. Androgen is a steroid hormone having functions such as sex differentiation into male, function maintenance of reproductive organs, secondary sexual development, spermatogenesis, and promotion of anabolic action in skeletal muscles and the like. Two androgens (testosterone and dihydrotestosterone (DHT) are mainly involved in masculinization of humans. Testosterone is, after synthesis in testicular interstitial cells, transported to target cells such as prostate cells via the blood stream. In the cells, testosterone is converted into DHT by 5-$\alpha$-hydrogenase and the resulting DHT binds to an androgen receptor (AR) in the cytoplasm. AR bound to DHT becomes an active type, is transported into the nucleus, and binds to an androgen responsive sequence on the target gene to function as a transcription factor activating expression of the target gene.

As therapeutic methods of prostate cancer other than surgical treatment, hormone therapy for inhibiting production and function of androgen is often employed and in most cases, it produces considerably good effects. Within several years after this hormone therapy, however, androgen-independent prostate cancer sometimes occurs. It therefore becomes an important object to control androgen-independent cancer.

Detailed molecular mechanism how androgen-dependent cancer progresses to androgen-independent cancer has not yet been elucidated, but involvement of AR in it has been suggested. More specifically, it has been suggested that in androgen independent cancer, AR which has undergone mutation or amplification shows sensitivity to ultra-low-concentration androgen or another steroid hormone (refer to, for example, Non-patent Documents 1 to 3). A method of treating prostate cancer by inhibiting binding of AR to ligand or inhibiting expression or function of AR by RNAi (RNA interference) method has been studied (refer to, for example, Non-patent Documents 4 to 6).

There is however a limitation in the method of inhibiting the function or expression of AR particularly for the treatment of prostate cancer which has recurred and a clinically sufficient method has not yet been developed.

PRIOR ART DOCUMENTS

Non-Patent Documents

Non-patent Document 1: Suzuki H, et al. Endocr. Relat. Cancer 10, 2003, 209-216
Non-patent Document 2: Chen C D, et al. Nat. Med. 10, 2004, 33-39
Non-patent Document 3: Debes J D, et al. N Eng J Med 351, 2004, 1488-1490
Non-patent Document 4: Sun A, et al. Int J. Cancer. 2009 Jul. 29. [Epub ahead of print] PMID: 19642108
Non-patent Document 5: Compagno D, et al. PLoS One. 2007 Oct. 10; 2(10): e1006.PMID: 17925854
Non-patent Document 6: Snoek R, et al. Clin Cancer Res. 2009 Jan. 1; 15(1): 39-47

DISCLOSURE OF THE INVENTION

Problem to be Solved by the Invention

An object of the present invention is to provide a cell growth inhibitor also effective for androgen-independent prostate cancer.

Means for Solving the Problem

With a view to overcoming the above-mentioned problem, the present inventors thought that since inhibition of AR was an important therapeutic method of prostate cancer and in androgen-independent cancer for which endocrine treatment was ineffective, AR signals were activated by mutation or amplification of AR, signals downstream of AR were useful as a therapeutic target. Based on this thought, an AR binding sites and a histone H3 acetylation sites were identified by using the chromatin immunoprecipitation method and a human whole genome tiling array in combination (ChIP-chip method; refer to, for example, Cawley S, et al. Cell 116, 2002, 499-509, Kaneshiro K, et al. Genomics. 89, 2007, 178-188) and moreover, by cap analysis gene expression (CAGE method, refer to, for example, Shiraki T, et al. Proc Natl Acad Sci USA. 100, 2003, 15776-81, FANTOM Consortium, Nat. Genet. 41, 2009, 553-562), transcriptional start sites were genome-widely identified and the promoter usage was profiled.

As a result, it has been found that a CTBP1 protein known to function as a corepressor in the nucleus functions as a transcription inhibitor of AR. It has been found during the study on CTBP1 that a transcript of a sense DNA in the vicinity of the AR binding site of the CTBP1 gene, that is, an antisense RNA in the vicinity of the AR binding site of the CTBP1 gene is induced strongly by androgen.

It has also been confirmed that suppression of the function of the antisense RNA by the RNAi enhances CTBP1 expression at both mRNA level and protein level, while it suppresses transcriptional activity of AR and suppresses proliferation of prostate cancer cells.

It has also been confirmed that the expression amount of the antisense RNA is significantly high in prostate cancer and metastatic cancer cells thereof compared with that of normal prostate and the expression amount of CTBP1 is significantly low in prostate cancer and metastatic cancer cells thereof compared with that of normal prostate.

It has further been confirmed that in a nude-mouse prostate cancer cell transplant model, the antisense RNA controls CTBP1 negatively and administration of a double-stranded RNA having an RNAi effect against the antisense RNA suppresses proliferation of prostate cancer.

Moreover, it has been confirmed that with regard to a mechanism of suppressing CTBP1-AS and thereby suppressing the growth of prostate cancer, PSF which is an RNA-binding transcriptional repressor binds to CTBP1-AS and this complex suppresses transcription of a cell cycle-inhibiting gene to promote cell growth; the complex suppresses the expression of CTBP1, resulting in promotion of transcription activation by AR; and accordingly, suppression of the expression of CTBP1-AS leads to inhibition of cell proliferation and suppression of activation of AR.

Furthermore, the present inventors have confirmed that suppression of PSF expression also results in inhibition of cell proliferation in prostate cancer, and completed the present invention.

The present invention therefore relates to:

[1] a cell growth inhibitor, which inhibits the growth of cells in which any of the following antisense RNAs (which will hereinafter be called "CTBP1-AS"):

(i) an antisense RNA of a CTBP1 gene containing a partial sequence of the base sequence represented by SEQ ID NO:1;

(ii) an antisense RNA of a CTBP1 gene containing the base sequence represented by SEQ ID NO:5; and (iii) a mutant or variant of the antisense RNA described above in (i) or (ii) or an antisense RNA in which one or several bases have been deleted, added, or substituted in the antisense RNA described above in (i) or (ii)

has been expressed, containing a CTBP1-AS expression inhibitor or function inhibitor as an active ingredient;

[2] the cell growth inhibitor as described in claim 1, wherein the CTBP1-AS is an antisense RNA having a base sequence described in any of SEQ ID NOS: 17 to 20;

[3] the cell growth inhibitor as described above in [1] or [2], wherein the expression inhibitor or function inhibitor is a compound selected from the group consisting of the following (a) to (d);

(a) antisense nucleic acids against CTBP1-AS or a portion thereof, (b) nucleic acids having ribozyme activity to specifically cleave CTBP1-AS;

(c) double-stranded nucleic acids having an RNAi effect against CTBP1-AS; and (d) nucleic acids encoding the nucleic acids described in any of (a) to (c);

[4] the cell growth inhibitor as described above in [3], wherein the expression inhibitor or function inhibitor is a double-stranded RNA having an RNAi effect against CTBP1-AS and one strand of the double-stranded RNA has a sequence complementary to consecutive 19 to 30 bases in CTBP1-AS;

[5] the cell growth inhibitor as described above in [3], wherein the expression inhibitor or function inhibitor is a double-stranded RNA having an RNAi effect against CTBP1-AS and one strand of the double-stranded RNA has a base sequence complementary to the base sequence represented by any of SEQ ID NOS:3 to 6 and 24 to 52;

[6] the cell growth inhibitor as described above in any one of [1] to [5], wherein the cells in which CTBP1-AS has been expressed are prostate cancer cells and/or metastatic cancer cells thereof;

[7] a pharmaceutical composition containing the cell growth inhibitor as described above in any one of [1] to [6];

[8] a method of preventing or treating prostate cancer, which includes administering a therapeutically effective amount of the cell growth inhibitor as described above in any one of [1] to [6];

[9] a method of screening growth inhibitors of cells in which CTBP1-AS has been expressed, including a step of bringing cells in which CTBP1-AS has been expressed or a cell extract thereof into contact with test compounds in the presence of androgen; a step of measuring an expression level of CTBP1-AS; and a step of selecting, from the test compounds, test compounds decreasing the expression level of CTBP1-AS compared with an expression level measured in the absence of the test compounds;

[10] a method of screening proliferation inhibitors of cells in which CTBP1-AS has been expressed, including a step of bringing cells which have expressed a CTBP1 gene or a cell extract thereof into contact with test compounds in the presence of androgen; a step of measuring an expression level of the CTBP1 gene; and a step of selecting, from the test compounds, test compounds increasing the expression level of the CTBP1 gene compared with an expression level measured in the absence of the test compounds;

[11] the method as described above in [9] or [10], wherein the cells in which CTBP1-AS has been expressed are prostate cancer cells and/or metastatic cancer cells thereof;

[12] a testing method for judging the prognosis of prostate cancer, including a step of measuring the expression level of CTBP1-AS in cells sampled from the prostate of a patient and a step of comparing the expression level with an expression level in normal prostate cells; and

[13] a testing method for judging the prognosis of prostate cancer, including a step of measuring the expression level of a CTBP1 gene in cells sampled from the prostate of a patient and a step of comparing the expression level with an expression level in normal prostate cells.

The present invention further relates to:

[14] A cell growth inhibitor, which inhibits the growth of cells in which any of the following antisense RNAs (which will hereinafter be called "CTBP1-AS"):

(i) an antisense RNA of a CTBP1 gene containing a partial sequence of the base sequence represented by SEQ ID NO:1;

(ii) an antisense RNA of a CTBP1 gene containing the base sequence represented by SEQ ID NO:5; and (iii) a mutant or variant of the antisense RNA described above in (i) or (ii) or an antisense RNA in which one or several bases have been deleted, added, or substituted in the antisense RNA described above in (i) or (ii)

has been expressed, comprising a PSF expression inhibitor or function inhibitor as an active ingredient;

[15] The cell growth inhibitor according to [14] above, wherein the CTBP1-AS is an antisense RNA having a base sequence described in any of SEQ ID NOS: 17 to 20;

[16] The cell growth inhibitor according to [14] above, wherein the expression inhibitor or function inhibitor is a compound selected from the group consisting of the following (a) to (d);

(a) antisense nucleic acids against PSF transcripts or a portion thereof, (b) nucleic acids having ribozyme activity to specifically cleave PSF transcripts;

(c) double-stranded nucleic acids having an RNAi effect against PSF transcripts; and (d) nucleic acids encoding the nucleic acids described in any of (a) to (c);

[17] The cell growth inhibitor according to [16] above, wherein the expression inhibitor or function inhibitor is a double-stranded RNA having an RNAi effect against PSF transcripts and one strand of the double-stranded RNA has a sequence represented by any of SEQ ID NOS:119 to 126;

[18] The cell growth inhibitor according to any one of [14] to [17] above, wherein the cells in which CTBP1-AS has been expressed are prostate cancer cells and/or metastatic cancer cells thereof;

[19] A pharmaceutical composition comprising the cell growth inhibitor as claimed in any one of [14] to [17] above;

[20] A method of preventing or treating prostate cancer, comprising administering a therapeutically effective amount of the cell growth inhibitor as claimed in any one of [14] to [17] above.

Effect of the Invention

The cell growth inhibitor of the present invention can efficiently inhibits the growth of cells in which expression of CTBP1-AS has been enhanced such as prostate cancer cells by inhibiting the expression or function of CTBP1-AS or PSF.

The cell growth inhibitor of the present invention suppresses transcriptional activity of signals downstream of AR by inhibiting expression or function of CTBP1-AS or PSF so that it is presumed to be effective against androgen-independent cancer in which AR signals have been activated by AR variation or amplification.

Using a double-stranded nucleic acid having an RNAi effect against CTBP1-AS or PSF as a cell growth inhibitor of the present invention enables high target specificity and high safety, because it makes use of a mechanism which cell originally have.

In addition, the present invention provides a screening method capable of efficiently selecting, from test compounds, a growth inhibitor of cells in which expression of CTBP1-AS has been enhanced; a method of preventing or treating prostate cancer; and a testing method for evaluating the prognosis of prostate cancer.

BRIEF DESCRIPTION OF THE DRAWINGS

FIG. 1 shows measurement results of the expression amount of CTBP1-AS when siRNA against CTBP1-AS or a control double-stranded RNA was administered to LNCaP cells. The CTBP1-AS expression was induced by androgen (R1881) and suppressed by the administration of siRNA against CTBP1-AS.

FIG. 2 shows measurement results of the expression amount of CTBP1 (mRNA level) when siRNA against CTBP1-AS or a control double-stranded RNA was administered to LNCaP cells. The CTBP1 expression was suppressed by androgen and the suppressive effect by androgen was decreased by the administration of siRNA against CTBP1-AS.

FIG. 3 shows measurement results of the expression amount of CTBP1 (protein level) when siRNA against CTBP1-AS or a control double-stranded RNA was administered to LNCaP cells. The CTBP1-AS expression was suppressed by androgen and the suppressive effect by androgen was decreased by the administration of siRNA against CTBP1-AS.

FIG. 4A shows the results of experiments to confirm the influence of CTBP1-AS on the transcriptional activity of AR obtained by introducing a PSA luciferase vector into LNCaP cells and administering siRNA against CTBP1-AS or a control double-stranded RNA to the resulting cells. Luciferase activity, that is, transcriptional activity of AR was increased by androgen and suppressed by the administration of siRNA against CTBP1-AS.

FIG. 6 shows the results of experiments to confirm the influence of function suppression of CTBP1-AS on a tumor volume in a mouse tumor model. Proliferation of tumor cells subcutaneously transplanted to mice was markedly suppressed by the administration of siRNA against CTBP1-AS.

FIG. 7 shows the results of experiments to confirm the influence of function suppression of CTBP1-AS on a tumor weight in a mouse tumor model. Proliferation of tumor cells subcutaneously transplanted to mice was markedly suppressed by the administration of siRNA against CTBP1-AS.

FIG. 16 shows the measurement results of a tumor volume (b), mRNA-level CTBP1-AS expression amount (c), and protein-level CTBP1 expression amount (d), after transplanting LTAD cells of an androgen-depletion resistant model to nude mice and locally injecting siRNA against CTBP1-AS.

FIG. 18 shows immunoprecipitation results showing androgen-dependent binding of PSF to CTBP1-AS.

FIG. 19 shows the results of analyzing localization of PSF and CTBP1-AS by RNA-FISH. Localization of PSF almost coincided with that of CTBP1-AS.

FIG. 22 shows the results of studying the control of a cell cycle-related factor by CTBP1-AS by using siRNA against CTBP1-AS.

MODE FOR CARRYING OUT THE INVENTION

Figure 1:
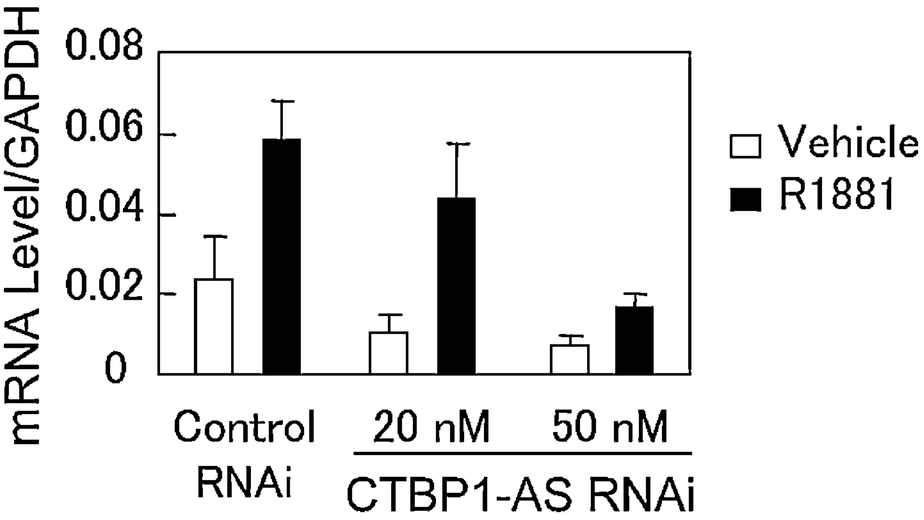

<Cell Growth Inhibitor Containing a CTBP1-AS Expression Inhibitor or Function Inhibitor>

The cell growth inhibitor according to the present invention is characterized in that it suppresses proliferation of cells in which CTBP1-AS has been expressed and that it contains a CTBP1-AS expression inhibitor or function inhibitor as an active ingredient.

The term "CTBP1" as used herein means a C-terminal binding protein 1 and the term "CTBP1 gene" means a gene encoding a CTBP1 protein. CTBP1 is known to function as a corepressor in the nucleus (Kim J H, et al. Nat Struct Mol. Biol. 12, 2005, 423-428, Senyuk V, et al. Arch Biochem Biophys. 441, 2005, 168-173). For example, involvement of CTBP1 in transcription suppression of a ZEB1 gene and the like has been reported and generally, it is presumed to negatively control the transcription (Chinnadurai G, Int J Biochem Cell Biol. 39, 2007, 1593-1607).

As described later in Examples, the present inventors have found that in prostate cancer cells, expression of CTBP1 is significantly reduced and it is controlled by androgen in both mRNA level and protein level expression.

The term "CTBP1-AS" as used herein means any one of antisense RNAs (i) to (iii) of a CTBP1 gene expressed in the vicinity of the AR binding site of the CTBP1 gene.

(i) An antisense RNA of a CTBP1 gene containing a partial sequence of the base sequence represented by SEQ ID NO:1, (ii) an antisense RNA of the CTBP1 gene containing the base sequence represented by SEQ ID NO:5, and (iii) a mutant or variant of the antisense RNA described above in (i) or (ii) or an antisense RNA in which one or several bases have been deleted, added, or substituted in the antisense RNA described above in (i) or (ii).

The term "antisense RNA" means a transcription product formed with a sense chain (sense DNA) of a double-stranded DNA of a gene as a template.

CTBP1-AS is a molecule which will be a target of the cell growth inhibitor according to the present invention. In the living body, there is a plurality of antisense RNAs capable of satisfying any one of the above (i) to (iii) and all of them will become CTBP1-AS. The antisense RNAs (i) to (iii) will next be described respectively in detail.

(i) Antisense RNA Of a CTBP1 Gene Containing a Partial Sequence of the Base Sequence Represented by SEQ ID NO:1

The antisense RNA of a CTBP1 gene having a base sequence represented by SEQ ID NO:1 is a transcription product of a sense DNA in the vicinity of the AR binding site of the CTBP1 gene and its cDNA is known to have Accession Number: AX747592 (SEQ ID NO:2).

Examples of the antisense RNA of a CTBP1 gene containing a partial sequence of the base sequence represented by SEQ ID NO:1 include:

an antisense RNA consisting of only a partial base sequence of the base sequence represented by SEQ ID NO:1;

an antisense RNA comprising a partial sequence containing the 5'-end of the base sequence represented by SEQ ID NO:1 and further having one or more bases bound to the 5'-end; and an antisense RNA comprising a partial sequence containing the 3' end of the base sequence represented by SEQ ID NO:1 and further having one or more bases bound to the 3' end.

The antisense RNAs expressed in the living body correspond to the antisense RNA of (i) insofar as it contains a partial sequence of the base sequence represented by SEQ ID NO:1. As a target of the cell growth inhibitor of the present invention, the antisense RNA consisting of a partial sequence containing the 3' end of the base sequence represented by SEQ ID NO:1 and the antisense RNA containing a partial sequence containing the 3' end of the base sequence represented by SEQ ID NO:1 and having one or more bases bound to the 3' end are particularly preferred. Examples of the "partial sequence containing the 3' end of the base sequence represented by SEQ ID NO:1" include, but not limited to, a partial sequence from position 1300 to the 3' end of the base sequence described in SEQ ID NO:1, a partial sequence from position 1200 to the 3' end, and a partial sequence from position 800 to the 3' end.

(ii) Antisense RNA of the CTBP1 Gene Containing the Base Sequence Represented by SEQ ID NO: 5.

Examples of the antisense RNA of the CTBP1 gene containing the base sequence represented by SEQ ID NO:5 include an antisense RNA consisting only of the base sequence represented by SEQ ID NO:5 and an antisense RNA having one or more bases bound to the 3' end and/or 5' end of the base sequence described in SEQ ID NO:5.

The base sequence represented by SEQ ID NO:5 corresponds to from position 2348 to position 2372 of the base sequence described in SEQ ID NO:1. The number of bases bound to the 3' end and/or 5' end is not particularly limited. The present inventors have confirmed that as shown later in Examples, administration of siRNA to this region as a target inhibits transcriptional activity of AR and also inhibits proliferation of prostate cancer cells. Accordingly, it is obvious that an expression inhibitor or function inhibitor of CTBP1-AS containing the base sequence represented by SEQ ID NO:5 is suited as an active ingredient of the cell growth inhibitor of the present invention.

As an example of the antisense RNA (ii), an antisense RNA containing the base sequence described in SEQ ID NO:23 is also preferred.

(Iii) Mutant or Variant Of the Antisense RNA as Described Above in (i) or (ii) or an Antisense RNA in which One or Several Bases have been Deleted, Added, or Substituted in the Antisense RNA Described in (i) or (ii).

Examples of the mutant or variant of the antisense RNA described in (i) or (ii) include various variants including splicing variants such as 5' alternative splicing and 3' alternative splicing, polymorphisms such as single nucleotide polymorphism (SNP) and copy number variation (CNV), and mutants (for example, cancer-derived mutants).

Also these mutants or variants can be expressed as a transcription product of a sense DNA in the vicinity of the AR binding site of a CTBP1 gene and will be a target of the cell growth inhibitor according to the present invention.

Although no particular limitation is imposed on the number of bases deleted or the like from the antisense RNA described in (i) or (ii) in which one or several bases have been deleted, added, or substituted insofar as it is a transcription product of a sense DNA in the vicinity of the AR binding site of the CTBP1 gene. The number is from 1 to 10, preferably from 1 to 5, more preferably from about 1 to 3 or corresponds to within 10%, preferably within 5%, more preferably within 1% of the entire length. Also the position of the bases to be deleted or the like is not particularly limited and it may be the base(s) at the 5' end or 3' end of the antisense RNA or the base(s) other than that at the ends. Alternatively, bases may be deleted, added, and/or substituted at a plurality of positions.

Such antisense RNAs may be expressed as a transcription product of the sense DNA at the AR binding site of CTBP1 gene and will be a target of the cell growth inhibitor according to the present invention.

Specific examples of the CTBP1-AS include RNAs consisting of the base sequence described in SEQ ID NOS:17 to 21.

The RNA having the base sequence described in SEQ ID NO:17 is an RNA of 3710 bases in total length which contains from position 698 to the 3' end of the base sequence described in SEQ ID NO:1 and further has an RNA of 522 bases bound to the 3' end (which will hereinafter be called “CTBP1-ASc”).

The RNA having the base sequence described in SEQ ID NO:18 is an RNA of 5041 bases in total length which contains from position 698 to the 3' end of the base sequence described in SEQ ID NO:1 and further has an RNA of 1853 bases bound to the 3' end (which will hereinafter be called “CTBP1-ASb”).

The RNA having the base sequence described in SEQ ID NO:19 is an RNA of 15756 bases in total length which contains from position 698 to the 3' end of the base sequence described in SEQ ID NO:1 and further has an RNA of 12568 bases bound to the 3' end (which will hereinafter be called “CTBP1-ASa”).

The RNA having the base sequence described in SEQ ID NO:20 is an RNA of 3189 bases in total length corresponding to from position 697 to the 3' end of the base sequence described in SEQ ID NO:1 (which will hereinafter be called “CTBP1-ASd”).

It has already been confirmed that any of these antisense RNAs has been expressed as a transcription product of a sense DNA in the vicinity of the AR binding site of a CTBP1 gene so that they will be a target of the cell growth inhibitor according to the present invention.

The present inventors have recently found newly by analysis using prostate cancer cells LNCaP that expression of CTBP1-AS is strongly induced by androgen. CTBP1-AS is a non-coding RNA which does not encode a protein motif. CTBP1-AS has an enhanced expression level in prostate cancer cells. Inhibition of CTBP1-AS by the RNAi method leads to suppression of transcriptional activity of AR and remarkable inhibition of cancer cell growth.

As will be described later in Examples, when CTBP1-AS binds to PSF, which is an RNA-binding transcriptional repressor, to form a complex, the resulting complex suppresses transcription of a cell-cycle inhibiting gene (for example, SMAD3 and p53). As a result, cell proliferation is accelerated.

On the other hand, the complex between CTBP1-AS and PSF also suppresses transcription of CTBP1 in cooperation with a histone deacetylation enzyme. Since CTBP1 originally has a function of suppressing transcription of an androgen receptor, suppression of transcription of CTBP1 enhances transcription activation by the androgen receptor. This leads to cell proliferation.

Accordingly, when the expression of CTBP1-AS is suppressed, as will be shown later in Examples, the proliferation of androgen-resistant cancer cells can also be suppressed.

The term “inhibition of cell growth” means that the proliferation of cells can be terminated or retarded.

The cell growth inhibitor according to the present invention is effective for all the cells in which CTBP1-AS has been expressed, but it is particularly useful for suppressing proliferation of cells showing enhanced CTBP1-AS expression. The term “cells showing enhanced CTBP1-AS expression” as used herein means cells having a significantly increased CTBP1-AS expression level compared with normal non-dividing cells. Examples of the cells having enhanced CTBP1-AS expression include, but not limited to, prostate cancer cells and metastatic cancer cells thereof. The term “metastatic cancer cells of prostate cancer” means cancer cells found in metastasis of prostate cancer.

The term “CTBP1-AS expression inhibitor” as used herein means a substance completely inhibiting transcription of CTBP1-AS, that is, transcription for production of CTBP1-AS using the DNA of a CTBP1 gene as a template or a substance significantly reducing such transcription. The term “expression” as used herein embraces transcription for production of a complementary RNA by using a DNA as a template and a transcriptase, synthesis of a protein based on genetic information which a DNA has, and translation for synthesis of a protein based on genetic information which mRNA has.

The term "CTBP1-AS function inhibitor" as used herein means a substance acting on CTBP1-AS itself and completely inhibiting its function or a substance significantly reducing the function. Examples include, but not limited to, substances promoting degradation of CTBP1-AS and substances hybridized with CTBP1-AS. The term "function of CTBP1-AS" as used herein means a function of suppressing expression of CTBP1 and activating AR signals downstream. Inhibition of the function of CTBP1-AS therefore means enhancing CTBP1 expression and suppressing activation of AR signals downstream.

The CTBP1-AS expression inhibitor or function inhibitor to be used in the present invention may be any substance insofar as it has the above-described function. Examples include low molecular compounds, high molecular compounds, proteins including antibodies and enzymes, and nucleic acids including single-stranded DNAs, double-stranded DNAs, single-stranded RNAs, double-stranded RNAs, chimeric nucleic acids containing a single-stranded or double-stranded DNA and a single-stranded or double-stranded RNA, and artificial nucleic acids (peptide nucleic acids (PNA) and locked nucleic acids (LNA)).

As the CTBP1-AS expression inhibitor or function inhibitor, the following ones are preferably used:

(a) antisense nucleic acids against CTBP1-AS or a portion thereof, (b) nucleic acids having ribozyme activity to specifically cleave CTBP1-AS, (c) double-stranded nucleic acids having an RNAi effect against CTBP1-AS, and (d) nucleic acids capable of expressing the nucleic acid described in any one of (a) to (c).

(a) Antisense Nucleic Acids Against CTBP1-AS or a Portion Thereof

The antisense nucleic acid method is well known as an expression inhibiting method. It is a method of introducing a single-stranded nucleic acid (antisense nucleic acid) having a base sequence complementary to a target gene (basically, mRNA which is a transcription product), hybridizing it with the target gene, and thereby inhibiting gene expression.

The antisense nucleic acid to be used in the present invention has preferably a sequence complementary to a portion of CTBP1-AS but it is not necessary that the sequence is completely complementary. For example, 90% or more, preferably 95% or more, more preferably 98% or more of the antisense nucleic acid is complementary to a portion of CTBP1-AS. No particular limitation is imposed on the length of the antisense nucleic acid insofar as it can produce an effect of inhibiting the function of CTBP1-AS. It has usually a length of from 10 bases to 100 bases, preferably a length of from 15 to 30 bases.

The antisense nucleic acid can be designed and synthesized as needed based on the base sequence of CTBP1-AS by those skilled in the art by using known software or the like. The antisense nucleic acid may be any of DNA, RNA, and chimeric nucleic acids containing DNA and RNA. They may be modified. Examples of the modified nucleic acid include those obtained by substituting a phosphate group with a thiophosphate group or a methyl phosphate group.

(b) Nucleic Acids Having Ribozyme Activity to Specifically Cleave CTBP1-AS

Examples of the CTBP1-AS function inhibitor also include nucleic acids having ribozyme activity to specifically cleave CTBP1-AS. Ribozyme is a nucleic acid molecule catalytically hydrolyzing a target RNA and is composed of an antisense region having a sequence complementary to a target RNA and a catalytic center region involved in cleavage reaction (for example, Ribozyme: Biochemistry and Biotechnology (Krupp, G. & Gaur, R. K. eds: Eaton Publishing, MA, 2000). Ribozyme which specifically cleaves CTBP1-AS can also be designed as needed in a manner known by those skilled in the art.

Ribozyme is usually an RNA molecule but a chimeric DNA-RNA molecule can also be used.

(c) Double-Stranded Nucleic Acids Having an RNAi Effect Against CTBP1-AS

As the CTBP1-AS function inhibitor, double-stranded nucleic acids having an RNAi effect against CTBP1-AS are also preferred. RNAi is a sequence-specific gene expression suppressing mechanism induced by a double-stranded nucleic acid. It has very high target specificity and is highly safe because it utilizes a gene expression suppressing mechanism originally present in the living body.

When it is used for mammal cells, a small double-stranded RNA (small interference RNA; siRNA) usually with from about 19 to 30 bases, preferably from about 21 to 25 bases is used. A longer double-stranded RNA which will be cleaved in the cell by an enzyme (Dicer) and become siRNA may also be used.

Cleavage of a target RNA molecule by RNAi is conducted as follows. First, siRNA is single-stranded by one-side chain cleavage by a protein called Argonaute or by rewinding by RNA helicase and then it binds to Argonaute to form a RISC (RNA induced silencing complex) which is an effector complex. In the RISC, siRNA serves as a guide molecule searching for the target RNA, while Argonaute functions as a ribonuclease (Slicer) cutting the target RNA.

A siRNA has typically a completely complementary double-stranded region of 19 bases and has two protruding bases (overhangs) at the 3' end of each of the sense strand and antisense strand but it may be a blunt end type having no overhangs. For example, a blunt end RNA with 25 bases is advantageous because it minimizes the activation of an interferon responsive gene, prevents an off-target effect derived from the sense strand, and has considerably high stability in the serum so that it is suited for use also in vivo.

Judging from the sequence of CTBP1-AS, the siRNA to be used in the present invention can be designed, by a known method for obtaining siRNA with high activity, by selecting a target region not having a sequence similar to that of another gene, containing a consensus sequence of siRNA with high activity, having a periodicity of three bases in its sequence, and having a GC content of from about 35 to 45%. For designing of siRNA, a known activity prediction algorithm can also be used. As such an activity prediction algorithm, siExplorer, siDirect, BIOPREDsi, and the like have been made public.

The double-stranded nucleic acid having an RNAi effect may be a double-stranded RNA or a chimeric DNA-RNA double-stranded nucleic acid, or it may contain an artificial nucleic acid. The chimeric type is obtained by substituting a portion of the double-stranded RNA having an RNAi effect with DNA so that it is known to have high stability in the serum and a low immunoresponse induction property.

The above-described double-stranded nucleic acid can have improved resistance to nuclease or be made more stable by modification of the 2'-OH group, phosphorothioate backbone substitution, modification with a boranophosphate group, or introduction of LAN (locked nucleic acid) having ribose bridged between the 2 and 4 positions thereof. Such a modified double-stranded nucleic acid is also embraced in the present invention.

(d) Nucleic Acids Capable of Expressing the Nucleic Acid Described Above in any One of (a) to (c)

The nucleic acids described above in (a) to (c) can be administered to the living body after synthesis. It is also possible to introduce a nucleic acid encoding any of these nucleic acids (a) to (c) into the living body and express the nucleic acid in cells.

For example, when a vector containing a DNA capable of expressing an antisense nucleic acid by transcription or a DNA capable of expressing a nucleic acid having ribozyme activity by transcription is introduced into cells, RNA expressed in the cells can inhibit the function of CTBP1-AS.

Further, a vector containing DNAs encoding the respective strands of a double-stranded RNA having an RNAi effect against CTBP1-AS may be introduced into cells. These two strands are expressed respectively and hybridized in the cells and as a result, produce an RNAi effect against CTBP1-AS. Alternatively, in order to express a double-stranded RNA having an RNAi effect, a vector containing a DNA encoding a single-stranded RNA obtained by binding respective strands of the double-stranded RNA via a loop can also be used. The single-stranded RNA thus expressed is hybridized in the molecule, constitutes a short hairpin RNA, is cleaved with Dicer at the loop structure portion thereof, and becomes an siRNA.

A construct capable of expressing a desired nucleic acid in cells can be designed as needed by those skilled in the art and introduced into the cells.

Examples of the double-stranded nucleic acids (c) having an RNAi effect against CTBP1-AS include those that target regions, in the base sequence of CTBP1-AS represented by SEQ ID NO:1, from position 1804 to position 1828 (SEQ ID NO:3), from positions 1894 to position 1918 (SEQ ID NO:4), from position 2348 to position 2372 (SEQ ID NO:5), and from position 3063 to position 3087 (SEQ ID NO:6).

Examples of the double-stranded nucleic acids targeting them include those having, as one of two strand, an RNA having a base sequence complementary to these targets and, as the other strand, an RNA having a base sequence complementary to the former one. Such double-stranded nucleic acids are shown in the following table.

the sequence of CTBP1-AS represented by SEQ ID NOS:24 to 52. Such double-stranded nucleic acids include double-stranded nucleic acids having an RNA composed of a base sequence represented by SEQ ID NOS:53 to 78 and an RNA complementary thereto. Of these, nucleic acids Nos. 3, 4, 6, 10, 12, 18, and 24 are highly effective for suppressing the expression of CTBP1-AS.

<Cell Growth Inhibitor Containing a PSF Expression Inhibitor or Function Inhibitor>

The term "PSF" as used herein means a RNA-binding transcription inhibitor, also called as PSF/SFPQ (slicing factor, proline-glutamine rich). As described above, PSF binds to CTBP1-AS and forms a complex that suppresses transcription of a cell-cycle inhibiting genes such as SMAD3 and p53, which results in acceleration of cell proliferation.

Furthermore, the complex of CTBP1-AS and PSF suppresses the transcription of CTBP1 cooperatively with a histone deacetylation enzyme. Since CTBP1 has a function of suppressing transcription of an androgen receptor, suppression of transcription of CTBP1 enhances transcription activation by the androgen receptor. As a result, the cell growth is inhibited.

The inventors of the present application have found, as will be shown later in Examples, that the suppression of PSF expression, like the suppression of CTBP1-AS expression, leads to the suppression of the growth of androgen resistant cancer cells.

The cell growth inhibitor containing a PSF expression inhibitor or function inhibitor according to the present invention is effective for all the cells in which CTBP1-AS has been expressed, but it is particularly useful for suppressing proliferation of cells showing enhanced CTBP1-AS expression.

The terms that are used in the descriptions of the cell growth inhibitor containing a PSF expression inhibitor or function inhibitor and are also used in the descriptions of the cell growth inhibitor containing a CTBP1-AS expression inhibitor or function inhibitor have the same meaning as those used in the descriptions of the cell growth inhibitor containing a CTBP1-AS expression inhibitor, unless otherwise specified.

TABLE 1

| Abbreviation | Target | siRNA |
|---|---|---|
| siRNA[1] | 1804-1828 | UGACCAGUCCGUUUGACACUGAGUG (SEQ ID NO. 7)<br>CACUCAGUGUCAAACGGACUGGUCA (SEQ ID NO. 8) |
| siRNA[2] | 1894-1918 | UUGAGAUGCCGGAAACAUUGAUGGG (SEQ ID NO. 9)<br>CCCAUCAAUGUUUCCGGCAUCUCAA (SEQ ID NO. 10) |
| siRNA[3] | 2348-2372 | UUAUGUCUCCAGCAAGCUUGGUCUU (SEQ ID NO. 11)<br>AAGACCAAGCUUGCUGGAGACAUAA (SEQ ID NO. 12) |
| siRNA[4] | 3063-3087 | GAGACAGGAGGAUGUAGUUUCUAAU (SEQ ID NO. 13)<br>AUUAGAAACUACAUCCUCCUGUCUC (SEQ ID NO. 14) |

The double-stranded nucleic acids of the present invention include the double-stranded nucleic acids having the above-described four regions as a target consisting of a strand having mismatches with the target RNA at from one to three bases and the other strand having a base sequence complementary to it, insofar as they produce an RNAi effect.

As the CTBP1-AS function inhibitor or expression inhibitor, an siRNA (for example, siRNA [3]) targeting a region represented by SEQ ID NO:5 is particularly preferred.

Examples of the double-stranded nucleic acids (c) having an RNAi effect against CTBP1-AS include those that target The term "expression" as used herein embraces transcription for production of a complementary RNA by using a DNA as a template and a transcriptase, and translation for synthesis of a protein based on genetic information which mRNA has. The term "PSF expression inhibitor" means a substance that completely inhibits transcription or translation, or significantly reduces such transcription or translation.

The term "PSF function inhibitor" as used herein means a substance acting on PSF itself and completely inhibiting its function or a substance significantly reducing the function. Examples include, but not limited to, substances promoting degradation of PSF and substances hybridized with nucleic acids encoding PSF. The term “function of PSF” as used herein means a function of forming a complex with CTBP1-AS and activating AR signals downstream. Inhibition of the function of PSF therefore means enhancing CTBP1 expression and suppressing activation of AR signals downstream.

The PSF expression inhibitor or function inhibitor to be used in the present invention may be any substance insofar as it has the above-described function. Examples include low molecular compounds, high molecular compounds, proteins including antibodies and enzymes, and nucleic acids including single-stranded DNAs, double-stranded DNAs, single-stranded RNAs, double-stranded RNAs, chimeric nucleic acids containing a single-stranded or double-stranded DNA and a single-stranded or double-stranded RNA, and artificial nucleic acids (peptide nucleic acids (PNA) and locked nucleic acids (LNA)).

As the PSF expression inhibitor or function inhibitor, the following ones are preferably used:

(a) antisense nucleic acids against PSF transcripts or a portion thereof, (b) nucleic acids having ribozyme activity to specifically cleave PSF transcripts, (c) double-stranded nucleic acids having an RNAi effect against PSF transcripts, and (d) nucleic acids capable of expressing the nucleic acid described in any one of (a) to (c).

Examples of (c) double-stranded nucleic acids having an RNAi effect against PSF transcripts include the siRNAs, one strand of which has a sequence selected from the followings:

```
                                        (SEQ ID NO: 119)
GCACGUUUGAGUACGAAUAUU

                                        (SEQ ID NO: 120)
GGCACGUUUGAGUACGAAUAU

                                        (SEQ ID NO: 121)
GCAUAUUAGGCUACGUAUUCC

                                        (SEQ ID NO: 122)
GAUGAUCGUGGAAGAUCUACA

                                        (SEQ ID NO: 123)
GGGAGAUCCCUAUGGUUCAGG

                                        (SEQ ID NO: 124)
GUUUGGGCAGGUAAAAUUAUG

                                        (SEQ ID NO: 125)
CAUAGGUUAUGAAGCUAAUCC

                                        (SEQ ID NO: 126)
GGCAUAGGUUAUGAAGCUAAU
```

<Pharmaceutical Composition>

The pharmaceutical composition of the present invention contains the above-mentioned cell growth inhibitor according to the present invention, i.e., (i) the cell growth inhibitor containing a CTBP1-AS expression inhibitor or function inhibitor or (ii) the cell growth inhibitor containing a PSF expression inhibitor or function inhibitor. The pharmaceutical composition of the present invention administered to cells in which CTBP1-AS expression has been enhanced therefore produces a proliferation suppressive effect against these cells so that it is particularly useful as a preventive or remedy of diseases in which AR-dependent cell proliferation is involved. Examples of the diseases in which AR-dependent cell proliferation is involved include AR-dependent cancers (typically, prostate cancer) and benign prostatic hyperplasia.

The pharmaceutical composition of the present invention may contain a pharmaceutically acceptable carrier or additive. Examples of such a carrier include, but not limited to, water, saline, phosphate buffer, dextrose, glycerol, pharmaceutically acceptable organic solvents such as ethanol, collagen, polyvinyl alcohol, polyvinylpyrrolidone, carboxyvinyl polymer, carboxymethyl cellulose sodium, sodium polyacrylate, sodium alginate, water-soluble dextran, carboxymethyl starch sodium, pectin, methyl cellulose, ethyl cellulose, xanthan gum, gum Arabic, casein, agar, polyethylene glycol, diglycerin, glycerin, propylene glycol, petrolatum, paraffin, stearyl alcohol, stearic acid, human serum albumin, mannitol, sorbitol, lactose, surfactants, excipients, flavoring agents, preservatives, stabilizers, buffers, suspending agents, tonicity agents, binders, disintegrants, lubricants, fluidity accelerators, taste corrigents, and the like.

The pharmaceutical composition of the present invention can be formulated into various forms, for example, liquids (such as injections), dispersants, suspensions, tablets, pills, powders, and suppositories. A preferred mode of the pharmaceutical composition is an injection and it is preferably administered parenterally (for example, intravenously, transdermally, intraperitoneally, or intramuscularly).

When the pharmaceutical composition of the present invention contains, as a cell proliferation inhibitor, a nucleic acid such as that described above in (a) to (c), preparations can be obtained by enclosing the nucleic acid with a carrier such as liposome, high-molecular micelle, or cationic carrier. A nucleic acid carrier such as protamine may be used. An affected part is preferably targeted by an antibody or the like bound to such a carrier. In addition, the retention in the blood can be improved by binding cholesterol or the like to the nucleic acid.

When a nucleic acid encoding the nucleic acid described above in any of (a) to (c) is contained as the cell growth inhibitor, the nucleic acid inserted in a virus vector such as retrovirus, adenovirus, or Sendai virus or in a non-virus vector such as liposome may be administered to cells.

<Therapeutic Method>

The method of preventing or treating prostate cancer according to the present invention is characterized by that a therapeutically effective amount of the cell growth inhibitor of the present invention, i.e., (i) the cell growth inhibitor containing a CTBP1-AS expression inhibitor or function inhibitor or (ii) the cell growth inhibitor containing a PSF expression inhibitor or function inhibitor, is administered.

The term “therapeutically effective amount” as used herein means an amount of an acting substance that ameliorates, to a certain extent, one or a plurality of symptoms to be treated. In prostate cancer, therefore, it means the amount that can achieve at least one of reduction in tumor size, inhibition (retardation or termination) of metastasis of tumor, inhibition (retardation or termination) of tumor growth, and relaxation of one or more symptoms related to cancer. The cell growth inhibitor can be administered as the above-mentioned pharmaceutical composition.

<Screening Method>

In a first mode, a method of screening cell growth inhibitors according to the present invention includes a step of bringing cells expressing CTBP1-AS or a cell extract thereof into contact with test compounds in the presence of androgen, a step of measuring the expression level of CTBP1-AS, and a step of selecting, from the test compounds, test compounds decreasing the expression level of CTBP1-AS compared with an expression level measured in the absence of the test compounds The cells in which CTBP1-AS has been expressed are not particularly limited insofar as they are cells in which CTBP1-AS has been expressed. For example, a variety of human cancer cells can be used. Of these, prostate cancer cells (LnCap cells and the like) showing high expression of CTBP1-AS and metastatic cancer cells thereof are preferred. Uterine cervix cancer cell strain HeLa cells, cell line 293 cells derived from kidney, mammary tumor cell line MCF27 cells, and the like can also be used. Cells in which CTBP1-AS has not been expressed sufficiently can be used as the cells in which CTBP1-AS has been expressed after introduction of an expression vector containing a DNA encoding CTBP1-AS.

In the screening method of the present invention, not cells themselves but a cell extract can be used. The cell extract can be prepared in a known manner by those skilled in the art.

Although test compounds to be used in the screening method of the present invention are not particularly limited, examples include organic compounds, inorganic compounds, nucleic acids (antisense nucleic acids, ribozymes, siRNAs, RNA adaptors, and the like), peptides, proteins (antibodies), and saccharides.

The test compounds can be brought into contact with cells in which CTBP1-AS has been expressed or a cell extract thereof, for example, by adding the test compounds to a medium of the cells or the cell extract.

When a nucleic acid is used as the test compound, the test compound can be introduced into cells by using cationic liposome method, electroporation method, microinjection method or the like. When siRNA is used as the test compound, a commercially available transfection kit may be used according to its instruction.

By bringing the test compounds into contact with cells or a cell extract in the presence of androgen, CTBP1-AS expression can be enhanced stably, making it possible to confirm the effect of the test compounds. For example, it is recommended to add androgen to the medium of cells or a cell extract three days after bringing the test compounds into contact with the medium or cell extract.

The step of measuring the expression level of CTBP1-AS can be performed by any method capable of measuring the expression amount of mRNA. For example, RNA collected from cells can be analyzed using Real-time PCR or northern hybridization method. It is to be noted that CTBP1-AS is a non-coding RNA so that the term "expression level" means an expression level of RNA.

The term "measured in the absence of the test compounds" means that the expression level of CTBP1-AS is measured by adding only androgen, without adding the test compounds, to similar cells or cell extract to those or that with which the test compounds are brought into contact. When compared with the value measured in this case, the value is significantly lower when measured by bringing the test compounds into contact with the cell or cell extract, the test compounds are selected as a cell growth inhibitor for cells showing enhanced CTBP1-AS expression.

In a second mode, a method of screening cell growth inhibitors according to the present invention includes a step of bringing cells in which a CTBP1 gene has been expressed into contact with test compounds in the presence of androgen, a step of measuring the expression level of the CTBP1 gene, and a step of selecting, from the test compounds, test compounds increasing the expression level of the CTBP1 gene compared with an expression level measured in the absence of the test compounds.

From the first mode, the second mode is different in using cells in which a CTBP1 gene has been expressed and selecting the test compounds increasing the expression level of the CTBP1 gene.

As the cells in which CTBP1 gene has been expressed, for example, prostate cancer cells (LNCap cells, etc.) or metastatic cancer cells thereof can be used. The cells in which CTBP1 has been expressed can also be prepared by introducing, into cells in which the CTBP1 gene has not been expressed, an expression vector containing a DNA encoding the CTBP1 gene. When the expression vector is introduced, a portion of the CTBP1 gene may be expressed not only by using a DNA encoding the full length of the CTBP1 gene but also by using a DNA encoding a portion of it. The CTBP1 gene encodes a CTBP1 protein so that the term "expression" embraces both transcription and translation.

In the expression level of the CTB1 gene, either the mRNA level expression or the protein level expression can be measured by those skilled in the art in a known manner. The mRNA level expression can be measured using Real-time PCR or northern hybridization similar to the measurement of CTBP1-AS. The protein level expression can also be measured by using electrophoresis such as SDS-PAGE or western blotting using an antibody against CTBP1 protein.

As described above, inhibition of the expression or function of CTBP1-AS leads to an increase in expression of CTBP1 protein, suppression of transcriptional activity of AR, and suppression of proliferation of cells showing enhanced CTBP1-AS expression. It is therefore possible to obtain proliferation inhibitors for cells having enhanced CTBP1-AS expression by selecting test compounds capable of increasing the expression level of the CTBP1 gene compared with the expression level measured in the absence of the test compounds.

The screening methods of the present invention may further include a step of administering the test compounds to cells having enhanced CTBP1-AS expression such as prostate cancer cells and performing cell proliferation assay (MTS assay) or a step of administering the test compounds to cancer-carrying animals to confirm the effect of them against the proliferation of cancer cells. By these steps, the effect of the test compounds can be examined further.

<Test Method>

The test method for evaluating the prognosis of prostate cancer according to the present invention includes a step of measuring the expression level of CTBP1-AS or a CTBP1 gene in cells collected from the prostate gland of a patient and a step of comparing the expression level with the expression level in normal prostate cells.

The present inventors have confirmed that the expression amount of CTBP1-AS in the prostate cancer cells of a patient and metastatic cancer cell thereof is significantly greater than that in normal cells and the expression amount of a CTBP1-gene is significantly smaller than that in normal cells. In addition, they have found that an increase in the expression amount of CTBP1-AS or a decrease in the expression amount of the CTBP1 gene has a correlation with the prognosis of a prostate cancer patient.

Accordingly, when as a result of the test using the test method of the present invention, expression of CTBP1-AS is significantly higher than that in normal cells, there is a high possibility of poor prognosis, while when the expression of CTB1 is significantly smaller than that in normal cells, there is a high possibility of good prognosis.

EXAMPLES

The present invention will hereinafter be described in detail based on Examples, but it should be noted that the invention is not limited by them.

I. The Cell Growth Inhibitor Containing CTBP1-AS Expression Inhibitor or Function Inhibitor Methods employed in the following Examples will next be described.

[RNA Fish and Fluorescent Immunostaining]

An antisense CTBP1-AS probe for detecting CTBP1-AS was prepared by using an RNA labeling kit (Roche) according to its manual. For colocalization study, LNCaP cells were cultured on a cover glass in a 24-well culture vessel. Twenty four hours after treatment with androgen, the cells were washed with PBS, allowed to stand in 3.6% formaldehyde and 10% acetic acid (in PBS) at room temperature for 20 minutes to fix them, and allowed to stand in 0.5% Triton X-100 at room temperature for 5 minutes for permeabilization. After washing with PBS, the cells were hybridized with the probe (overnight at 42° C. in a moist chamber) and detected using a donkey anti-DIG antibody bound to Alexa555. Endogenous PSF was reacted overnight with a rabbit anti-PSF antibody at 4° C. and detected using an anti-rabbit IgG antibody bound to Alexa488, followed by imaging using a confocal microscope.

[RNA Immunoprecipitation (RIP)]

Confluent LNCaP cells were collected on a 15-cm dish and re-suspended in 1 ml NP40 lysis buffer (50 mM Tris pH 8.0, 150 mM NaCl, and 1% NP40). An antibody to Sin3A, PSF, or NONO or IgG (Santa cruz Biotechnology, Sigma, BD, or Sigma, respectively) was added to the supernatant and the resulting mixture was rotated overnight at 4° C. Protein G beads (30 μL) were added and the mixture was incubated at 4° C. for 2 hours while mildly rotating it. The beads were washed three times with a lysis buffer and then re-suspended in 1 ml ISOGEN. The RNA co-precipitated was isolated and the mRNA level of CTBP1-AS was analyzed using qRT-PCR.

[Northern Blotting]

Preparation of an antisense CTBP1-AS probe and subsequent analysis by northern blotting were conducted by using a Northern blot starter kit (Roche) according to its manual. Total RNA (1 μg) was modified and then loaded on a formaldehyde-containing agarose gel (in 1×MOPS buffer). RNA was transferred on a Hybond-XL membrane (Roche) and detected using an RNA probe labeled with DIG and extending across the center portion of CTBP1-AS.

[Microarray]

The total RNA of LNCaP cells was collected using an ISOGEN reagent (Nippon Gene). As an expression analysis microarray, Gene chip human exon 1.0 ST array (Affymetrix) was used according to its manual. Data were analyzed using Affymetrix Microarray Suite software. With regard to a comparison array, data from all probe sets were standardized.

[ChIP and Quantitative Real Time PCR]

ChIP was performed in a conventional manner (Takayama K, et al. Oncogene 26, 4453-63 (2007)). After treatment for 5 minutes with 1% formaldehyde to crosslink protein and DNA, the cells were collected and a protein-DNA extract was prepared. The extract was subjected to sonication. After reaction overnight with a specific antibody and a non-specific IgG, the protein-DNA complex was collected using a protein A/G agarose. The complex was then washed and reacted overnight at 65° C. to de-crosslink it. DNA was collected by ethanol precipitation. Fold enrichment relative to IgG control was quantified by real time PCR using SYBR green PCR master mix (Applied Biosystems) and ABI Prism 7000 system (product of Applied Biosystems) based on SYBR green I fluorescence. PCR products thus obtained respectively were relatively quantified by the Comparative cycle threshold method (Ct method). GAPDH was used as an external standard. The sequences of the primers used are shown in the following table.

TABLE 2

| Gene | Primer | SEQ ID NO. |
|---|---|---|
| CTBP1 (intron 1) | F: GGACGCCTGTATGGAAGCA | 105 |
| | R: TCCGCAGACGCCTTTTG | 106 |
| CTBP1-ARBS | F: GCACTGTGTGGCATAAAAAGAAAA | 107 |
| | R: TGGAACGTGCCCCAGAA | 108 |

[Real Time RT-PCR]

The total RNA was isolated using an ISOGEN reagent. The first cDNA strand was produced using a Primescript RT reagent kit (Takara) and mRNA was quantified using real time PCR.

The primers used are shown in the following table.

TABLE 3

| Gene | Primer | SEQ ID NO. |
|---|---|---|
| CTBP1 | F: TGGCCACTGTGGCCTTCT | 109 |
| | R: CGTTCAGGACCTTCTCATGGA | 110 |
| CTBP1-AS | F: AACCTGGCAGCACGGAAGT | 111 |
| | R: GAGCACAACCACCACCTCATC | 112 |
| TMPRSS2 | F: TCAACCCCTCTAACTGGTGTGA | 113 |
| | R: AGGCGAACACACCGATTCTC | 114 |
| SMAD3 | F: CCCCAGAGCAATATTCCAGA | 115 |
| | R: GGCTCGCAGTAGGTAACTGG | 116 |
| p53 | F: CCCCTCTGAGTCAGGAAACA | 117 |
| | R: TCATCTGGACCTGGGTCTTC | 118 |

[siRNA]

A Stealth RNAi system targeting CTBP1-AS, CTBP1 (HSS102437), NONO(HSS143135), PSF (HSS109643), and Sin3A (HSS177954) and a negative control were purchased from Invitrogen. Transfection of cells was conducted using a Lipofectamine RNAi MAX reagent (Invitrogen) from 48 to 72 hours before the test. The sequence of siRNA against CTBP1-AS is siRNA 5'-UUAUGUCUCCAGCAAGCUUGGUCUU.

[In Vivo Tumor Formation Assay]

LNCaP cells ($3\times10^6$ cells) or LTAD cells ($1\times10^7$ cells) were transdermally injected to both sides of 20 male, 5-week-old nude mice. From the mice transplanted with the LTAD cells, the testicle was removed by surgery at the time when the tumor volume reached 100 $mm^3$. Three times a week, 5 μg of siRNA against CTBP1-AS or control siRNA was transfected into the tumor by using Lipofectamine RNAi MAX transfection Reagent. The tumor volume was determined according to the following formula: $0.5\times r1\times r2\times r3$ ($r1<r2<r3$).

[Cell Proliferation Assay]

Cells were cultured on a 96 well plate at $3\times10^3$ cells/well. Stable cell lines of pcDNA3 CTBP1-AS were inoculated onto a 1%-FBS-containing PRMI medium. For RNAi test, the cells were transfected with stealth RNA 24 hours after transfer to the plate. MTS assay was performed using a cell titer reagent (Promega) according to its manual. The test was repeated five times for each.

[Cell Culture and Reagent]

LNCaP cells (human prostate cancer cells) were cultured on a RPMI medium containing 10% FBS, 50 units/ml of penicillin, and 50 μg/ml of streptomycin. Prior to treatment with androgen, the cells were cultured for from 48 hours to 72 hours on a phenol red free medium containing 5% dextran charcoal stripped FBS. The antibodies used were Sin3A (AK-11), p53 (Pab-240), p21 (F-5), CyclinD1 (C-20), CyclinA (H-432), CyclinB1 (H-433) (Santa cruz Biotechnology), CTBP1 (#612042), NONO (#611278) (BD bioscience), ACH3K9 (#07-352) (Upstate), PSF (#61045) (Novus Biologicals), and SMAD3 (#04-1035) (Millipore). Antibodies against AR, ACH3, and β-actin are described in the report of Takayama, et al. (Takayama K, et al. Oncogene 26, 4453-63 (2007); Cancer Res. 69(1):137-42 (2009); Oncogene 30(5): 619-30 (2011)). Dihydrotestosterone and Bicaltamide were purchased from Wako Pure Chemical Industries.

[Western Blotting, Immunoprecipitation]

Conducted in a conventional manner (Takayama K, et al. Oncogene 26, 4453-63 (2007)). The cells were collected in an NP40 buffer and a protein extract was prepared. AN adequate amount of the extract was boiled for 5 minutes in a Laemmli sample buffer and separated using SDS-PAGE. After transcription to a PVDF membrane, it was blocked with 5% non-fat dry milk and reacted overnight with a primary antibody at 4° C. The reaction product was then reacted for one hour with a secondary antibody against rabbit or mouse IgG, followed by color development and photographing.

[Luciferase Assay]

Prior to transfection, LNCaP cells were incubated for 24 hours on a phenol red free medium containing 5% charcoal stripped FBS. Then, with a FuGENE6 reagent (Roche Diagnostics), the cells were transfected with an ARBS-containing pGL3 vector and tk-PRL. Twenty four hours after transfection, luciferase activity was measured in a conventional manner. In a luciferase assay using RNAi in combination, the transfection of RNA was conducted 72 hours before stimulation with androgen.

[Analysis of Cell Cycle]

After transfection of control siRNA or siRNA against PSF, incubation was conducted for 96 hours and cells were collected. The cells were centrifuged and washed with PBS. While agitating mildly, 3 ml of ice-cooled 70% ethanol was added slowly to fix them. Until use, they were stored at 4° C. On the cell cycle analysis day, the cells were centrifuged, washed with PBS, re-suspended in PBS containing 100 μg/ml RNaseA (Takara) at $10^6$ cells/ml, and incubated at 37° C. for 30 minutes. In order to measure the DNA content, 30,000 cells were analyzed by FACS Calibur flow cytometry using Cell Quest software (BD Biosciences).

[Analysis of Microarray Data]

Microarray analyses of siRNA against CTBP1-AS and siRNA against PSF were conducted, independently. As a result of a test using siRNA against PSF, 700 genes are presumed to be suppressed by PSF. The function of these target genes were identified using DAVID and for pathway analysis, REACTOME was used. In each analysis, 300 genes obtained from the control sample were identified as genes suppressed by androgen.

<Discovery of CTBP1-AS>

Considering that inhibition of signals downstream of AR is effective as a target of prostate cancer treatment, the present inventors have established a method of finding a gene directly targeted by AR by using chromatin immunoprecipitation and tiling array in combination (ChIP-chip method) (Takayama K. et al. Oncogene 26, 2007, 4453-4463, Takayama K. et al. Cancer Res. 69, 2009, 137-142). Moreover, to elucidate the transcription network by androgen, ChIP-chip analysis was conducted on the whole human genome level by using, in addition to AR, an antibody against acetylation at histone H3K9/K14 to identify the AR binding site (ARBS) and the histone H3 acetylation site (ACH3).

In addition, Cap Analysis gene expression (CAGE) was conducted using LNCaP cells. CAGE is a method of sequencing concatemers of DNA tags derived from 20 bases from the 5' end of mRNA, carrying out genome-wide identification of a starting point of transcription, and profiling the promoter usage and is therefore a high throughput method. A region where CAGE tags were mapped to the human genome and aggregated as a result of CAGE analysis was defined as a tag cluster (TC). Of the TCs, those undergoing a significant change in the distribution of tags were identified.

Based on the recent report (Katayama S. et al. Science 309, 2005, 1564-1566) that an antisense transcription product controls the expression of genes in the vicinity of the product and the finding that transcription control of AR is an important signal of the onset of prostate cancer, the relationship between the transcriptional activity of AR and an antisense transcription product was considered to be an important factor for describing the advance of cancer. As a result of searching for an androgen responsive gene controlled by an antisense, CTBP1 was found.

In addition, in the vicinity of ARBS of CTBP1, an antisense TC to be activated by androgen was found. According to GENBANK, it was found to have ex3 of AX747592 as a starting point of transcription. The antisense RNA was therefore named CTBP1-ASd (SEQ ID NO:20).

CTBP1-ASd contains a sequence encoding the sequence of 330 amino acids. It has been found from the analysis by the present inventors by using Pfam that this amino acid sequence does not encode a protein motif. Analysis using Netstart has revealed that the first methionine is unlikely to function as a starting point of protein translation. Furthermore, as a result of a test by the IVT method (in vitro transcription method), protein synthesis from CTBP1-ASd was not recognized (data not shown). These results mean that CTBP1-ASd is a non-coding RNA not encoding a protein motif.

<Preparation of siRNA Having RNAi Effect Against CTBP1-ASd>

As siRNA, stealth RNAi (Invitrogen) designed based on the base sequence of CTBP1-Asd was used. It is a blunt end type double-stranded RNA having a length of 25 bases longer than the typical siRNA and is characterized by that it can minimize the activation of an interferon responsive gene, can prevent an off-target effect derived from the sense strand, and has very high stability in the serum. It also has actual using results in vivo.

The optimum site of the siRNA sequence was determined using the RNAi Designer on Invitrogen's website. The sequence of siRNA thus prepared is as described below.

TABLE 4

| Abbreviation | Target | siRNA |
|---|---|---|
| siRNA[1] | 1804-1828 | UGACCAGUCCGUUUGACACUGAGUG (SEQ ID NO. 7)<br>CACUCAGUGUCAAACGGACUGGUCA (SEQ ID NO. 8) |
| siRNA[2] | 1894-1918 | UUGAGAUGCCGGAAACAUUGAUGGG (SEQ ID NO. 9)<br>CCCAUCAAUGUUUCCGGCAUCUCAA (SEQ ID NO. 10) |

TABLE 4-continued

| Abbreviation | Target | siRNA |
|---|---|---|
| siRNA[3] | 2348-2372 | UUAUGUCUCCAGCAAGCUUGGUCUU (SEQ ID NO. 11) |
| | | AAGACCAAGCUUGCUGGAGACAUAA (SEQ ID NO. 12) |
| siRNA[4] | 3063-3087 | GAGACAGGAGGAUGUAGUUUCUAAU (SEQ ID NO. 13) |
| | | AUUAGAAACUACAUCCUCCUGUCUC (SEQ ID NO. 14) |

In Examples described below, the above-mentioned siRNA [3] was administered to a siRNA administration group. As a control in the siRNA test (except in vivo test), a double-stranded RNA (Stealth™ RNAi Negative Control Medium GC Double-stranded, Invitrogen 12935-300) not showing a RNAi effect against CTBP1-ASd was administered.

<Androgen-Dependent Expression of CTBP1-AS and Effect of SiRNA Administration on Androgen-Dependent Expression Suppression of CTBP1 Gene>

In the test, LNCaP cells of an AR-positive human prostate cell line were used. For cell culture, RPMI1640 (Sigma) containing 10% fatal bovine serum (FBS, Sigma), 100 μg/ml streptomycin, and 100 U/ml penicillin (Invitrogen) was used as a cell broth. The cells were cultured at 37° C. in an incubator containing 5% carbon dioxide gas in the air.

On a 6-well plate, $1\times10^5$ LNCaP cells were cultured. On the following day, 20 nM and 50 nM siRNAs were introduced into the cells by using Hiperfect Transfection Reagent (Quiagen) and OPTI-MEM (Invitrogen). Forty eight hours later, the resulting cells were stimulated with 10 nM androgen R1881 or Vehicle. After culturing for further 24 hours, RNA was collected using ISOGEN (Nippon gene).

Expression analysis of mRNA was conducted using Real-time PCR (Prism7000 system; Applied biosystems). From an amplification curve available by the Real-time PCR method, an intracellular expression amount of a transcription product was determined by the ΔΔCt method. The expression amount was corrected based on the expression amount of a GADPH gene.

Measurement results of the CTBP1-AS expression are shown in FIG. 1. In Control, expression of CTBP1-AS was accelerated androgen-dependently, but in the cells of the siRNA administration group, CTBP1-AS expression was suppressed in a siRNA-concentration dependent manner. In the cells administered with 50 nM siRNA, expression induction by androgen was suppressed by from 60 to 80%.

Figure 2:
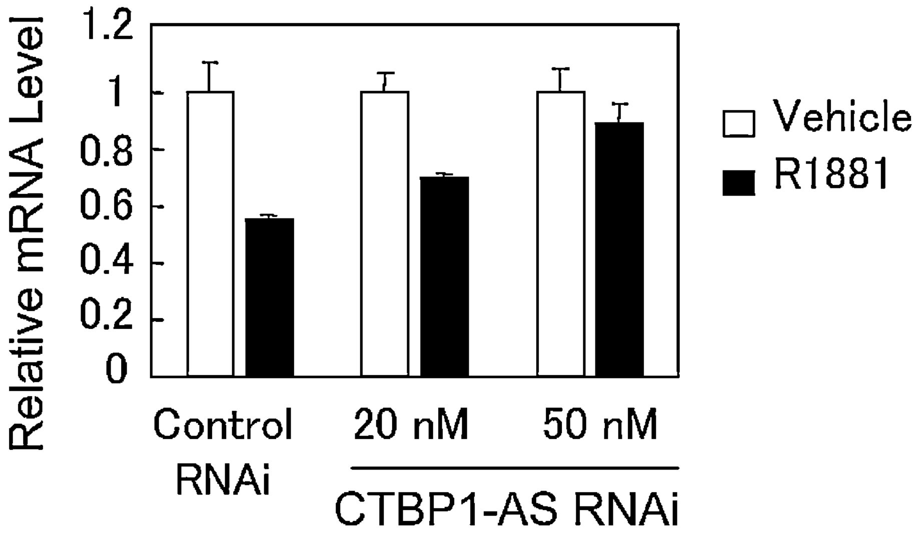

The measurement results of the expression of mRNA of CTBP1 are shown in FIG. 2. In Control, the expression of mRNA of CTBP1 was suppressed by androgen. On the other hand, in the siRNA administration group, the expression suppression effect of CTBP1 by androgen disappeared in a siRNA-concentration dependent manner.

Figure 3:
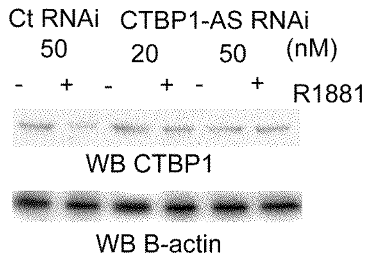

In addition, 24 hours after treatment with 10 nM R1881, a protein was collected and the protein-level expression amount of CTBP1 was measured by western blotting. The results are shown in FIG. 3. The protein-level expression was also suppressed by androgen administration, but due to the administration of siRNA, the expression suppression effect decreased in a siRNA-concentration dependent manner.

<Luciferase Assay>

Luciferase assay was conducted to confirm the influence of CTBP1-AS on transcriptional activity of AR.

A luciferase vector was prepared by inserting, in the promoter region of pGL3-basic (Promega), the promoter and enhancer of PSA (Prostate specific antigen), that is, a typical androgen responsive gene (PSA-LUC). PSA-LUC has an AR binding site and the promoter is activated androgen-responsively.

LNCaP cells were sprayed and cultured on a 24-well plate at $3\times10^4$ cells/well. After culturing for 2 days on a phenol red-free medium containing 2.5% charcoal serum, PSA-LUC was introduced. On the following day, the resulting cells were stimulated with 10 nM R1881 or Vehicle. The cells were collected after 24 hours. Luciferase activity was measured using a Dual-Luciferase Reporter Assay System (Promega).

Two days before introduction of the vector into the cells, siRNA and control double-stranded RNA were administered by the above-described method.

Figure 4A:
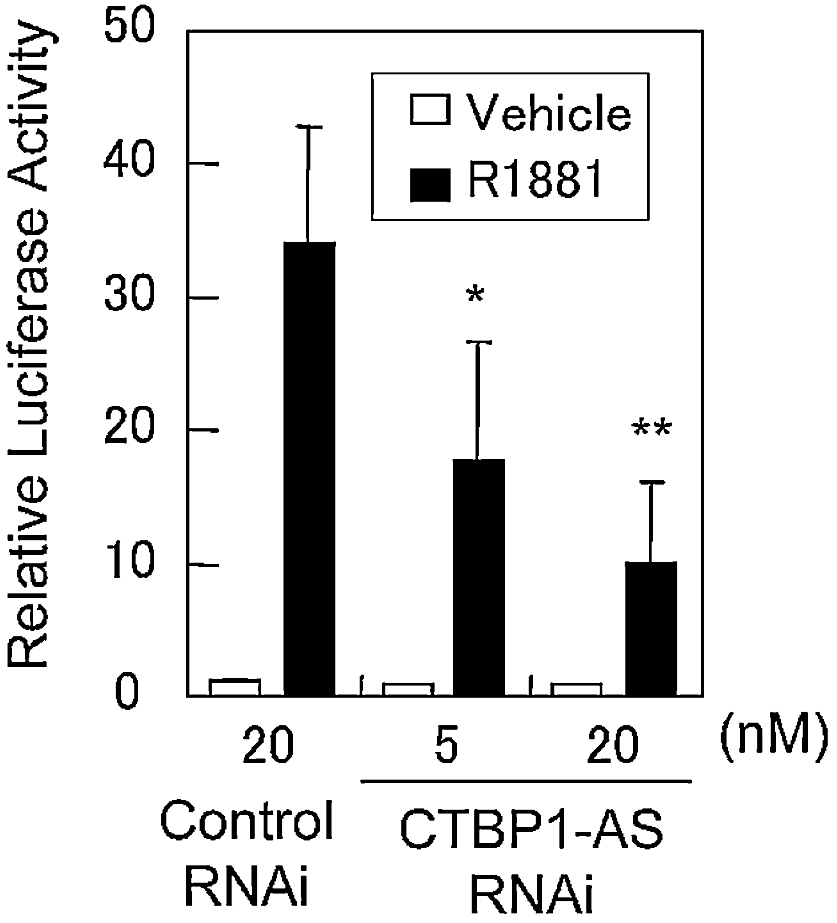

The results are shown in FIG. 4A. It has been demonstrated in Control that luciferase activity showed a marked increase and administration of androgen enhanced AR transcriptional activity, which activated the PSA promoter and enhancer. In the siRNA administration group, on the other hand, luciferase activity was markedly suppressed.

Figure 4B:
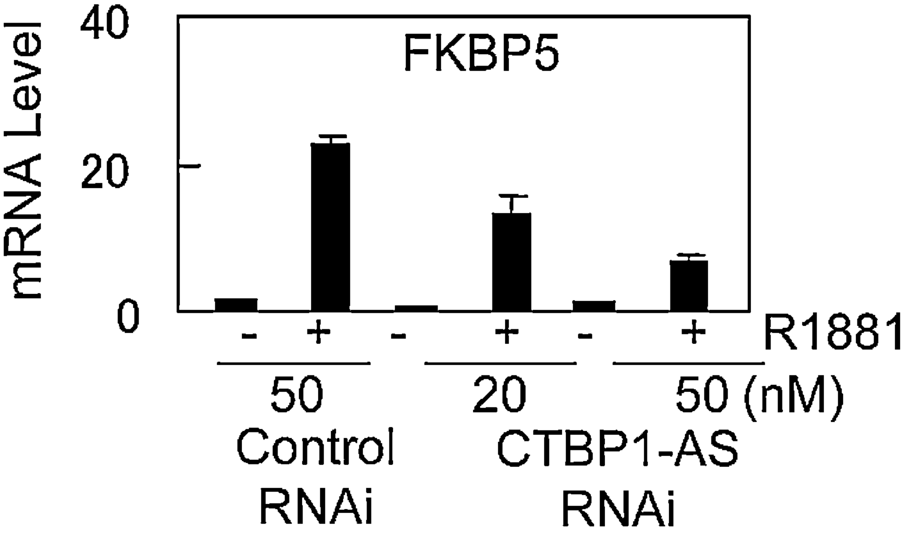
FIG. 4B is studying results of the expression of an androgen responsive gene FKBP5 in the cells. The expression amount of the androgen responsive gene was increased by androgen, but suppressed by the administration of siRNA.
Figure 4C:
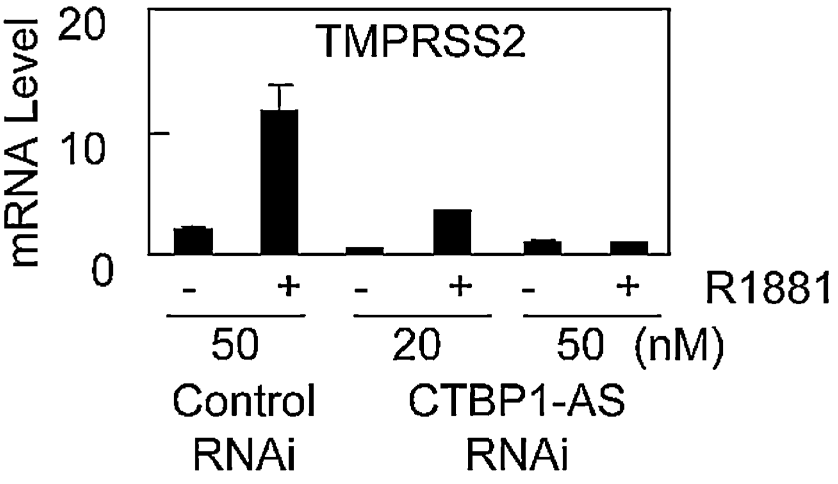
FIG. 4C is studying results of the expression of an androgen responsive gene TMPRSS2 in the cells. The expression amount of the androgen responsive gene was increased by androgen, but suppressed by the administration of siRNA.

The results of studying the expression of an androgen responsive gene in the same cells are shown in FIGS. 4B and 4C. In Control, the expression amounts of FKBP5 and TMPRSS2, that is, typical androgen responsive genes, increased, while in the siRNA administration group, an increase in the expression amount was suppressed in a concentration dependent manner.

It has been confirmed from the above-mentioned results that suppression of CTBP1-AS leads to suppression of AR transcriptional activity.

<Influence of Function Suppression of CTBP1-AS on Proliferation of LNCaP Cells>

The cell-level influence of CTBP1-AS on LNCaP cell was analyzed using MTS assay.

On a 96-well plate, LNCaP cells were continuously cultured at $3\times10^3$ cells/well. Similar to luciferase assay, siRNA was administered on the following day. Forty eight hours, 72 hours, and 96 hours after administration, the resulting cells were reacted for one hour by using Cell titer 96 (Promega).

MTS assay is a method of measuring a viable cell count based on a reduction reaction for converting, via PES (phenazine ethosulfate), a tetrazolium salt (3-(4,5-dimethylthiazol-2-yl)-5-(3-carboxymethoxyphenyl)-2-(4-sulfophenyl)-2H-tetrazolium, inner salt; MTS) into a formazan product which is a chromogenic substance. The cell proliferation ability was measured at an absorbance of 490 nm by using a microplate reader.

Figure 5:
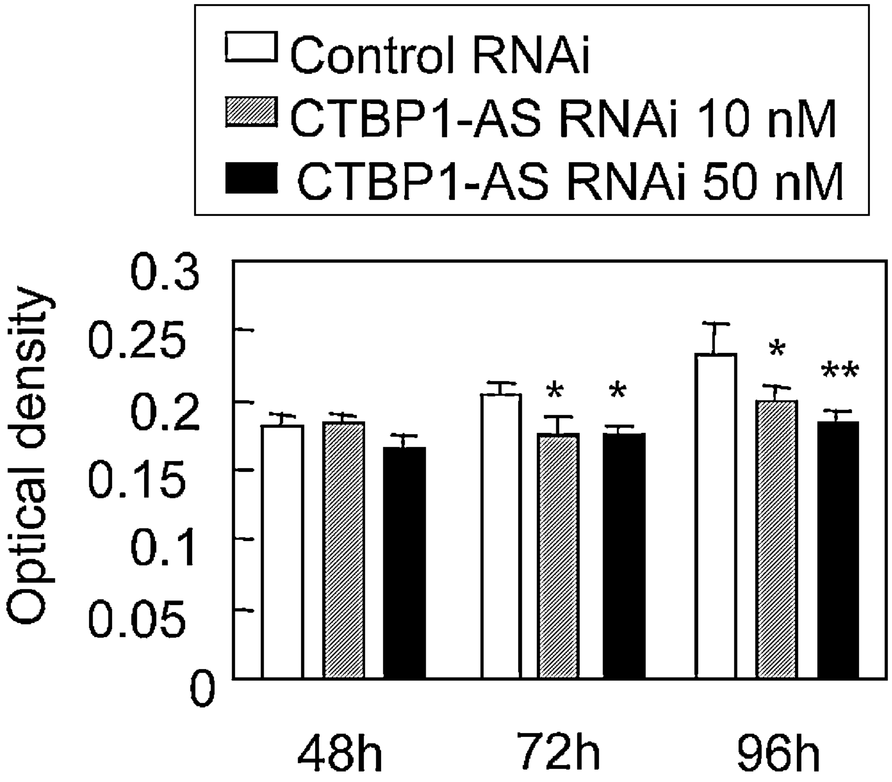
FIG. 5 shows the results of experiments to investigate the influence of function suppression of CTBP1-AS on the proliferation of LNCaP cells by using MTS assay. Administration of siRNA against CTBP1-AS suppressed cell proliferation.

The results are shown in FIG. 5. It has been found that in the siRNA administration group, compared with Control, cell proliferation was significantly suppressed and CTBP1-AS promoted the proliferation of LNCaP cells.

<Influence of Function Suppression of CTBP1-AS on Tumor Proliferation In Vivo>

Influence of CTBP1-AS and function suppression of CTBP1-AS on the tumor proliferation in vivo was analyzed.

To subcutaneously transplant LNCaP cells to mice, they were mixed with PBS and matrigel (BD bioscience). The mixture for 20 mice was prepared at a time so that the cells, PBS, and matrigel per mouse be $1\times10^7$ cells/mice, 100 μl, and 100 μl, respectively.

The mixture was injected subcutaneously to 6-week-old male BALB/c nude mice (CLEA Japan) by using a 25G injection needle.

Injection of siRNA into tumor was conducted using Gene silencer (Genlantis). A mixture obtained by mixing 5 μg of siRNA with 5 μl of Gene silencer in OPTI-MEM was locally injected into the mouse tumor. In control group, a double-stranded RNA having the following base sequence was similarly administered.

```
                                    (SEQ ID NO: 15)
AAGACGAUCGUUCGGGACAACAUAA

                                    (SEQ ID NO: 16)
UUAUGUUGUCCCGAACGAUCGUCUU
```

The siRNA injection was started two weeks after the cancer cells transplanted into mice seemed to be subcutaneously engrafted and it was conducted twice a week.

The size of the mouse tumor was measured once a week. The major axis (r1) and the minor axes (r2, r3) were measured at two positions and the size of the tumor was determined based on the formula: (r1×r2×r3)/2.

Ten weeks after transplantation, mice were sacrificed and their tumor was excised from under the skin. After the tumor was weighed, a portion of it was provided for RNA extraction using ISOGEN. After cDNA synthesis, RNA level expression amounts of CTBP1-AS and CTBP1 were measured using Real time-PCR. Another portion was dissolved in an SDS lysis buffer (10 mM Tris-HCl, pH7.5, 2% SDS, 10% mercaptoethanol). The resulting solution was provided for protein extraction and a CTBP1 expression amount was measured using western blotting.

The results are shown in from FIG. 6 to FIG. 9.

Figure 6:
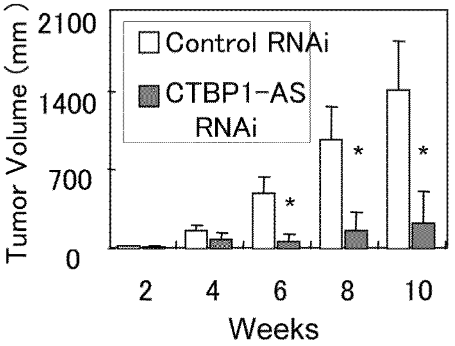
Figure 6:
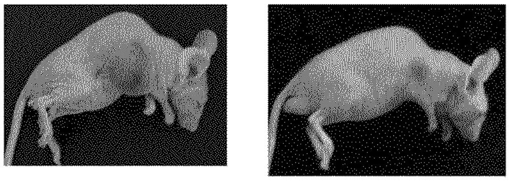
Figure 7:
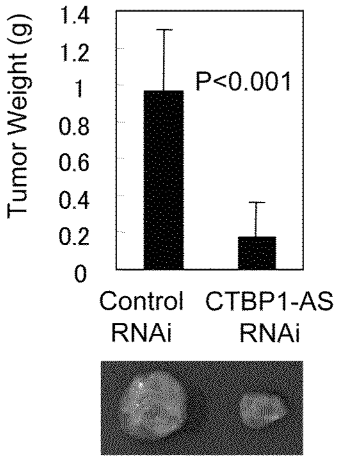

As shown in FIG. 6, in the siRNA administration group, compared with Control, proliferation of the tumor was significantly suppressed ($p<0.01$). As shown in FIG. 7, it has been observed that in the siRNA administration group, an increase in the tumor weight was suppressed markedly ($p<0.001$).

Figure 8:
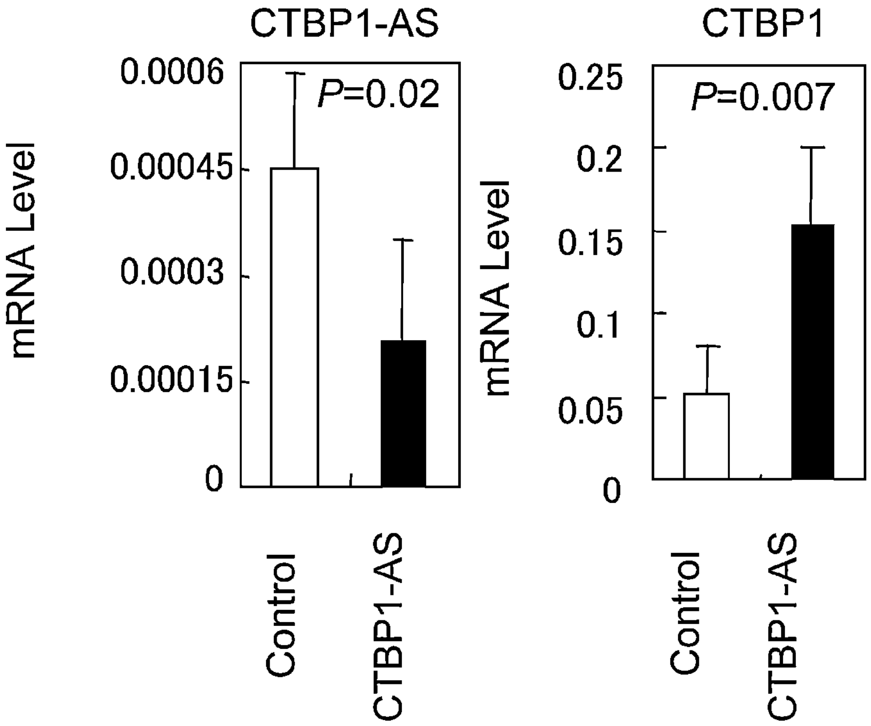
FIG. 8 shows the measurement results of the RNA level expression amounts of CTBP1-AS and CTBP1 in mouse tumor model. Administration of siRNA against CTBP1-AS decreased the expression amount of CTBP1-AS in tumor but increased the expression amount of CTBP1.

FIG. 8 shows the measurement results of the RNA level expression amount of CTBP1-AS and CTBP1 in the tumor by using Real time-PCR. Compared with Control group, the expression level of CTBP1-AS in the tumor of four mice was reduced by administration of RNAi against CTBP1-AS. On the other hand, the expression amount of CTBP1 was increased by the administration of RNAi against CTBP1-AS compared with Control group. These results have revealed that also in vivo, CTBP1 is under negative control of CTBP1-AS.

Figure 9:
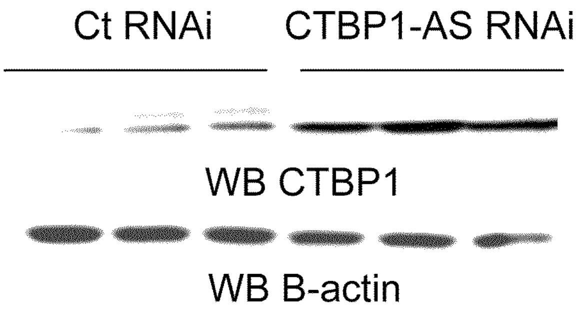
FIG. 9 shows the measurement results of the protein level expression amounts of CTBP1 in mouse tumor model. Administration of siRNA against CTBP1-AS increased the expression amount of the CTBP1 protein in tumor.

FIG. 9 shows the measurement results of the protein-level expression amount of CTBP1 in tumor by western blotting. In the RNAi administration group, compared with Control group, the protein level expression amount of CTBP1 was also increased.

It has been confirmed from the above results that a mechanism of suppressing CTBP1 by CTBP1-AS also functions in in vivo tumor proliferation in the tumor model and suppression of tumor proliferation is promoted by the suppression targeting CTBP1-AS.

<Expression of CTBP1-AS in Actual Tumor>

Expression profile data (GSE3325) of prostate and prostate cancer cases using Human Genome U133 Plus 2.0 array of Affymetrix made public in GEO Datasets on NCBI (http://www.ncbi.nlm.nih.gov) were downloaded.

Signal intensity was extracted while paying attention to the probe (1563571_at) specific to CTBP1-AS (AX747592) of normal, cancer, and metastasis samples. Mann-Whitney U test was conducted and the expression amount was compared among these groups.

Figure 10:
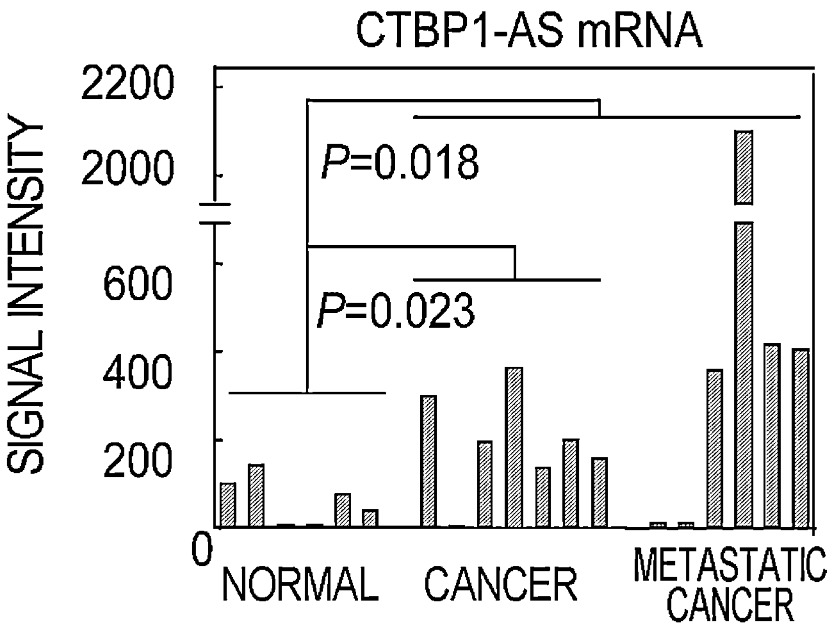
FIG. 10 shows the comparison results of the expression amount among normal, cancer, and metastatic cancer samples determined by extracting the signal intensity of a probe specific to AX747592 based on the published expression profile data. The expression amount of CTBP1-AS in cancer and metastasis cancer tissues was significantly higher than that in normal prostate.

The results are shown in FIG. 10. The expression amount of CTBP1-AS in cancer and the cancer tissue of distant metastasis were significantly higher than that of normal prostate ($p<0.05$, Mann-Whitney U test). It has been presumed from this result that CTBP1-AS is involved in the onset and development of cancer.

<Expression of CTBP1 in Actual Cancer>

Expression of CTBP1 in the actual prostate cancer was assessed by immunostaining. Immunostaining was performed according to the method of Suzuki, et al. (Suzuki T. et al. Clin. Cancer Res. 2005 Sep. 1; 11(17): 6148-54).

Cases were selected from 104 cases with a surgical specimen of prostate cancer excised from 1987 to 2001 in the Urology/the University of Tokyo Hospital. After 99 sections corresponding to the normal site and 101 sections corresponding to the prostate cancer were fixed in formalin, paraffin sections were prepared. As a primary antibody, CTBP1-specific mouse monoclonal antibody (BD Bioscience) was used. With Histofine Kit (Nichirei) for immunohistochemical staining, staining was conducted with a 3,3'-diaminobenzidine solution [1 mmol/L 3,3'-diaminobenzidine, 50 mmol/L Tris-HCl buffer (PH7.6), and 0.006% $H_2O_2$]. Images of sections representative of normal prostate and prostate cancer are shown in FIG. 11C.

A labeling index (LI) in the nucleus of CTBP1 in each section was measured. The expression of CTBP1 protein in the normal tissue and cancer tissue was quantified and compared.

Figure 11A:
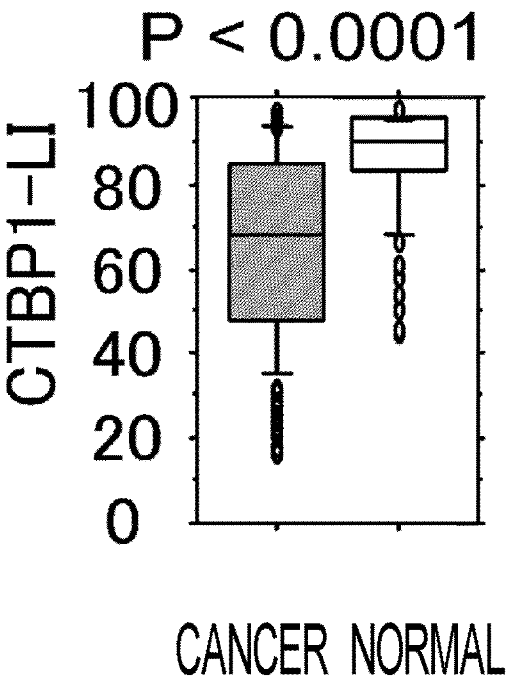
FIG. 11A shows the results of experiments to assess the CTBP1 expression in prostate cancer cells by using immunostaining method. The CTBP1 expression amount was decreased in prostate cancer cells compared with that in normal cells.

The results are show in FIG. 11A. The expression amount of CTBP1 decreased in prostate cancer cells compared with that in normal cells.

With regards to 101 prostate cancer cases, a survival rate was compared between a CTBP1 high expression group and a CTBP1 low expression group based on the data obtained by tracking the progress on an outpatient basis every three months after surgery for five years and the results were analyzed using the Kaplan-Meier method with the Long-rank test. The classification into the high expression group and the low expression group was conducted based on the median of Labeling Indices showing the expression of CTBP1.

Figure 11B:
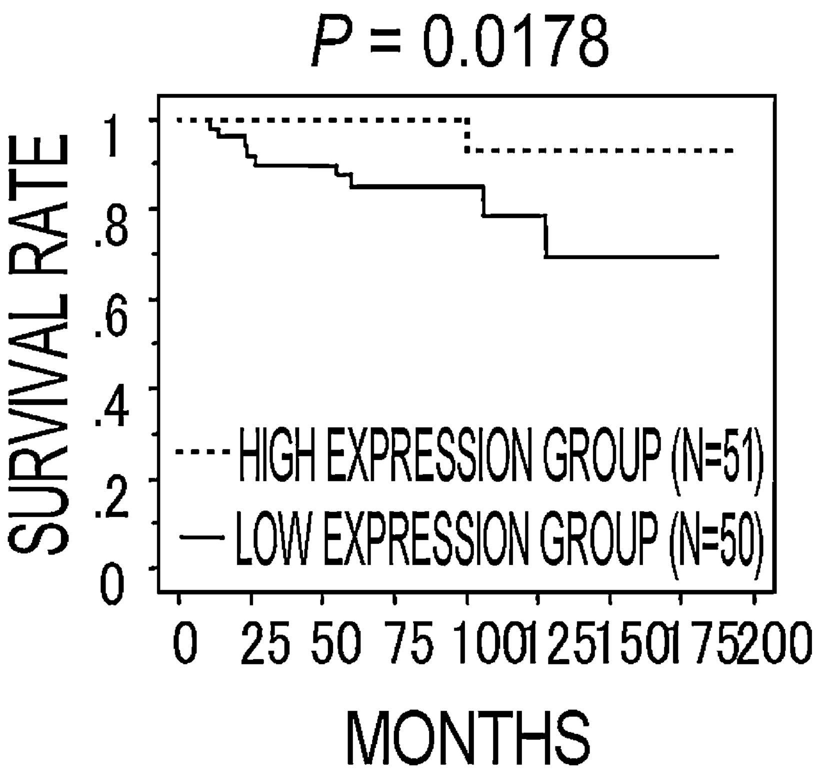
FIG. 11B shows the comparison results of a survival rate between CTBP1 high expression group and low expression group. The survival rate was significantly higher in the CTBP1 high expression group than that in the low expression group.
Figure 11C:
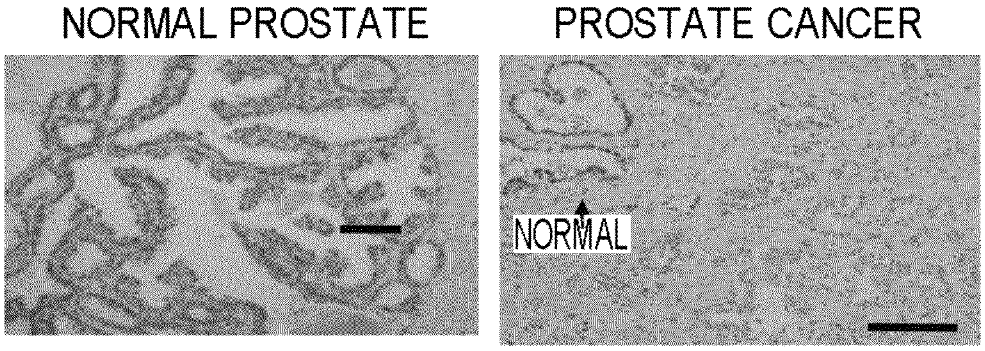
FIG. 11C shows images of typical sections of normal prostate and prostate cancer obtained by immunostaining method.

The results are shown in FIG. 11B. The survival rate was significantly high in the CTBP1 high expression group compared with that in the low expression group.

It has been confirmed from the above results that a suppressing mechanism of CTBP1 by CTBP1-AS also functions in proliferation of actual tumor.

<Identification of CTBP1-AS Except CTBP1-ASd>

CTBP1-ASs except CTBP1-ASd expressed in prostate cancer cells were searched in the following manner.

Twenty four hours after stimulation of LNCaP cells with 10 nM R1881, RNA was collected. RNA (1 μg) was treated with 1 μl of DNase (Roche, 10 U/μl) and a reverse transcription reaction was then conducted using a RACE Kit (Roche). Next, a PCR reaction was conducted using primers obtained by the CAGE method, one of which was in the vicinity of a starting point of transcription and the other one had an adapter-specific sequence at the terminal. The PCR product thus obtained was inserted into a plasmid by using a TA Cloning Kit (Invitrogen). The plasmid was sequenced and the sequence of the transcription product obtained by the PCR reaction was analyzed. The sequence thus obtained was mapped to a human genome sequence and a range of the transcription product was determined.

The following are the 3' RACE primer and PCR adaptor primer used.

```
3'RACE primer:
                                        (SEQ ID NO: 21)
5'-GACCACGCGTATCGATGTCGACTTTTTTTTTTTTTTTTV-3'

PCR adaptor primer:
                                        (SEQ ID NO: 22)
5'-GACCACGCGTATCGATGTCGAC-3'
```

Figure 12:
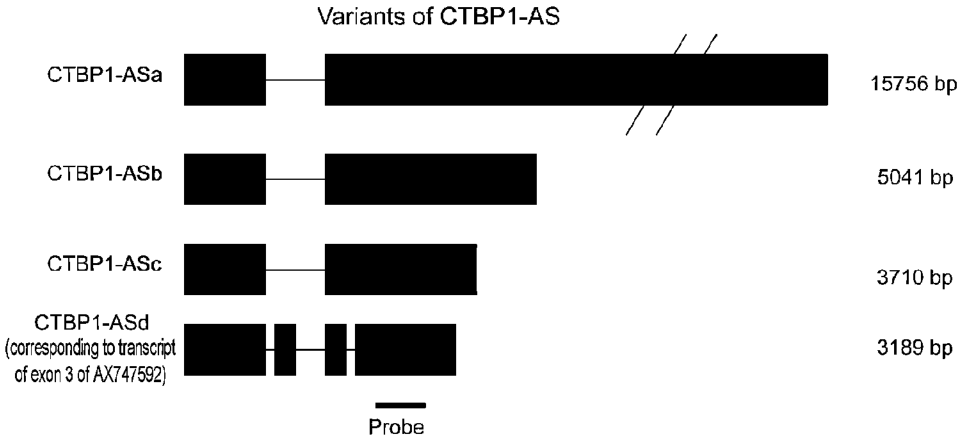
FIG. 12 is a schematic view showing sequences of CTBP1-ASa, CTBP1-ASb, and CTBP1-ASd whose existence has been confirmed as a result of searching for CTBP1-ASs other than CTBP1-ASd by using the 3' RACE PCR method.

The results show that there are at least four kinds of CTBP1-AS as shown in FIG. 12. One of them is the above-described CTBP1-ASd. The base sequence of CTBP1-ASa is shown in SEQ ID NO:19, the base sequence of CTBP1-ASb is shown in SEQ ID NO:18, and the base sequence of CTBP1-ASc is shown in SEQ ID NO:17.

These CTBP1-Ass each contain the target sequence of siRNA described in the above table. It is therefore presumed that in the expression suppression test using siRNA in the above Example, expression of these CTBP1-AS was also suppressed.

A probe for detecting, as a sequence which CTBP1-ASa to CTBP1-ASd have in common, a region (SEQ ID NO:23) from position 1286 to position 3515 of the RNA sequence described in SEQ ID NO:1 was prepared and northern blotting was conducted. The probe was prepared following the protocol by using DIG Northern Starter Kit (Roche).

LNCaP cells were stimulated with 10 nM R1881 and 0, 6, 12, 18, 24, and 48 hours later, RNAs were collected. RNAs (each, 1 μg) were electrophoresed on an agarose gel containing formaldehyde and transferred to a membrane. The membrane was hybridized with the above probe (100 ng/ml) and a DIG-specific antibody was used for detection.

In order to measure the amount of RNA used in the test, a probe (Roche) against β actin was purchased at the same time and the same membrane was used for detection.

Figure 13:
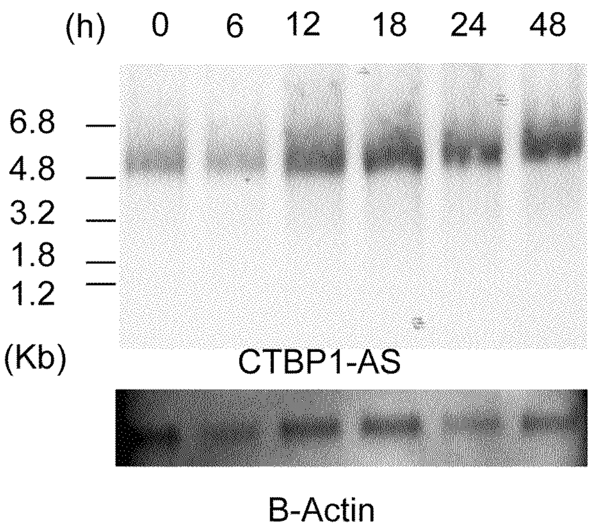
FIG. 13 shows the northern blotting results by which expression of CTBP1-AS was confirmed using LNCaP-cell-derived RNA. An about 5-kb long transcription product is detected, suggesting that CTBP1-ASb is expressed mainly.

The results are shown in FIG. 13. A transcription product having a length of about 5 kb was detected, suggesting that among the above-mentioned four kinds of CTBP1-ASs, CTBP1-ASb was expressed mainly.

<Localization of CTBP1-AS>

LNCaP cells were treated for 24 hours with 10 nM R1881 or Vehicle. From the cells collected, intranuclear RNA and cytoplasmic RNA were extracted using a PARIS kit (Ambion). From respective samples of them, 1 μg of RNA was electrophoresed and an expression amount was analyzed using northern blotting. As Loading Control, a probe against β-actin was hybridized and an expression amount was measured. The expression amount of each of the genes was corrected by GAPDH.

Figure 14:
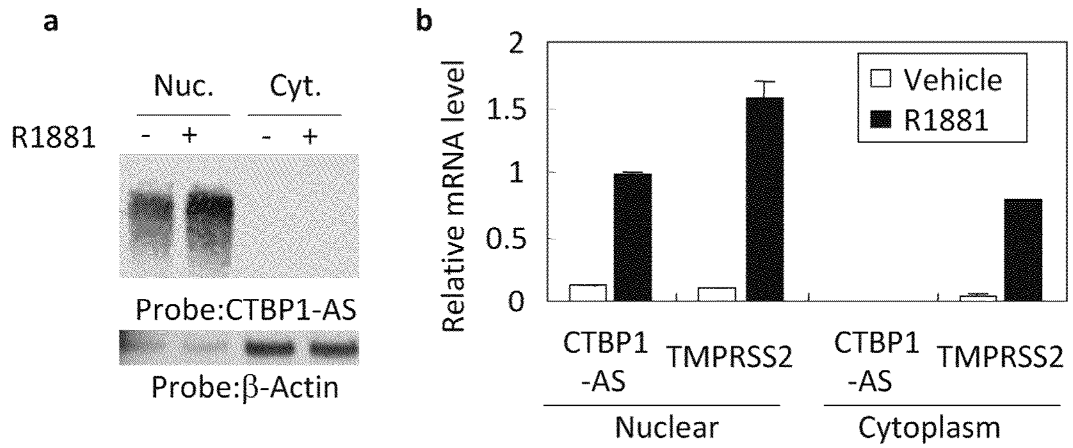
FIG. 14 shows the results of analyzing localized CTBP1-AS by northern blotting using nuclear RNA and cytoplasmic RNA (FIG. 14*a*) and the results of measuring the expression amount of cDNA synthesized from RNA by using qRT-PCR (FIG. 14*b*, corrected by GAPDH).

The results are shown in FIG. 14. Intranuclear localization of CTBP1-AS was confirmed.

<Involvement of CTBP1-AS in Androgen-Depletion Resistant Cancer Cell Proliferation—In Vitro>

Lysates of LTAD cells and LNCaP cells (2.5% charcoal serum, cultured for 3 days, stimulated with R1881, R1881+ Bicaltamide added) and western blotting was conducted using a CTBP1 antibody. A probe against β-actin was used as a Roding Control.

In order to compare the expression amount of CTBP1-AS between LTAD cells and LNCaP cells, Total RNA of LTAD cells and LNCaP cells (2.5% charcoal serum, cultured for 3 days, stimulated with R1881, R1881+Bicaltamide added) were collected. The RNA (1 μg) was electrophoresed, transferred, and subjected to northern blotting with a probe against CTBP1-AS.

Figure 15:
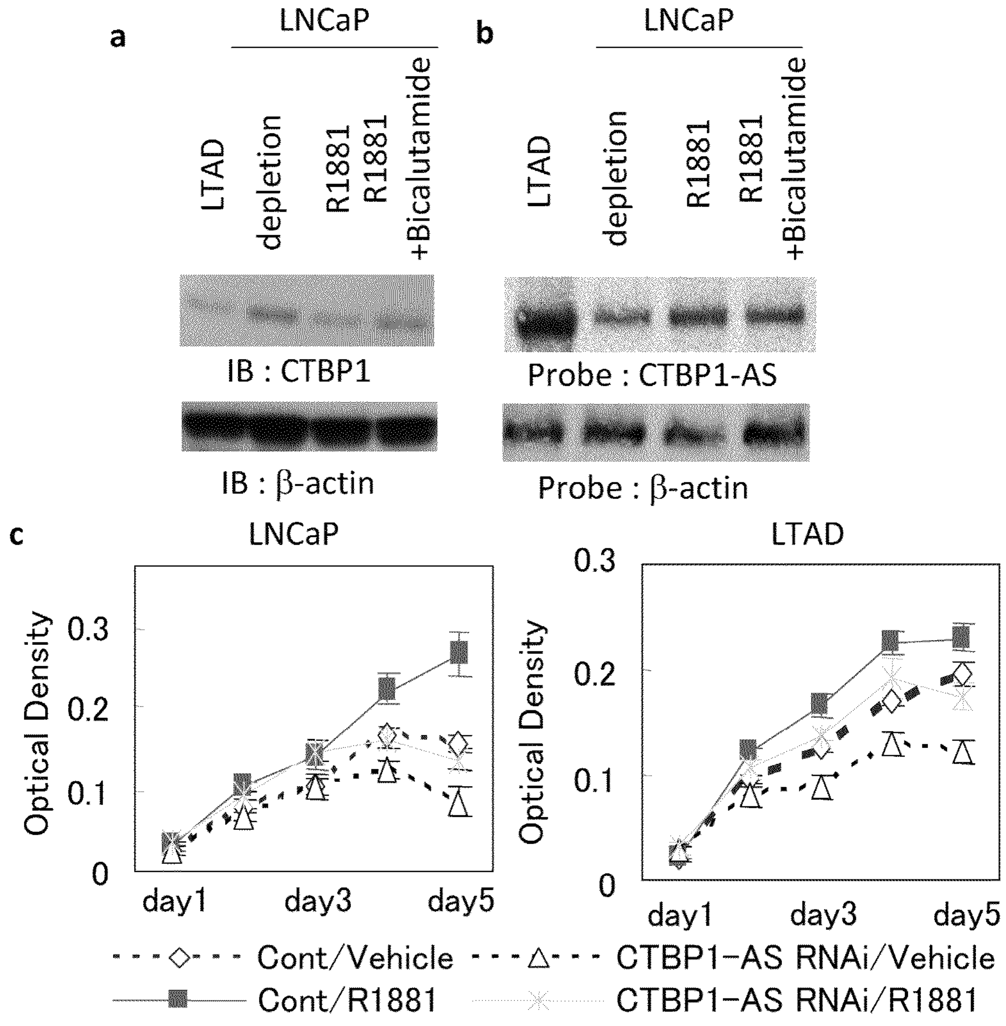
FIGS. 15*a* and 15*b* show the analysis results of the influence of androgen stimulation on the expression of CTBP1 and CTBP1-AS in LNCaP cells and LTAD cells which will be an androgen depletion resistant model by western blotting and northern blotting.
FIGS. 15*c* and 15*d* show comparison results of cell proliferation ability compared by suppressing CTBP1-AS expression by RNAi method with or without androgen stimulation in LNCaP cells or LTAD cells.

The results are shown in FIGS. 15*a* and 15*b*. The LTAD cells were cultured under an androgen-depleted state to be a hormone therapy resistant model. When the LNCaP cells were stimulated with androgen, expression of CTBP1 was decreased to a similar level to that of the LTAD cells. In the LTAD cells, expression of CTBP1-AS was increased remarkably.

Next, an influence of CTBP1-AS on hormone-dependent or hormone-depleted proliferation of prostate cancer cells was analyzed.

LNCaP cells were sprayed on a phenol red-free medium containing 2.5% charcoal serum at $3\times10^3$ cells/well. On the following day, RNAi against CTBP1-AS was transfected. Two days later, the cells were stimulated with Et or R1881 and on Day 1, 3, and 5, MTS assay was performed to evaluate proliferation ability.

Separately, the LTAD cells were sprayed on a phenol red-free medium containing 2.5% charcoal serum at $3\times10^3$ cells/well. On the following day, RNAi against CTBP1-AS was transfected. Two days later, the cells were stimulated with Et or R1881 and on Day 1, 3, and 5, MTS assay was performed to evaluate proliferation ability.

The results are shown in FIG. 15*c*. Cancer cells proliferate even without stimulating the androgen depletion resistant LTAD cells with androgen. Either androgen-dependent proliferation or androgen-independent proliferation was suppressed by knockdown of CTBP1-AS.

<Involvement of CTBP1-AS in Androgen-Depletion Resistant Cancer Cell Proliferation—In Vitro>

The role of CTBP1-AS in proliferation of hormone therapy resistant cells was analyzed in vivo.

LTAD cells were subcutaneously transplanted to nude mice at $1\times10^7$ cells/mouse. The testicle was removed by surgery at the time when the tumor volume reached 100 $mm^3$. Control siRNA or siRNA against CTBP1-AS was locally injected (5 μg/mouse, twice/week).

Figure 16:
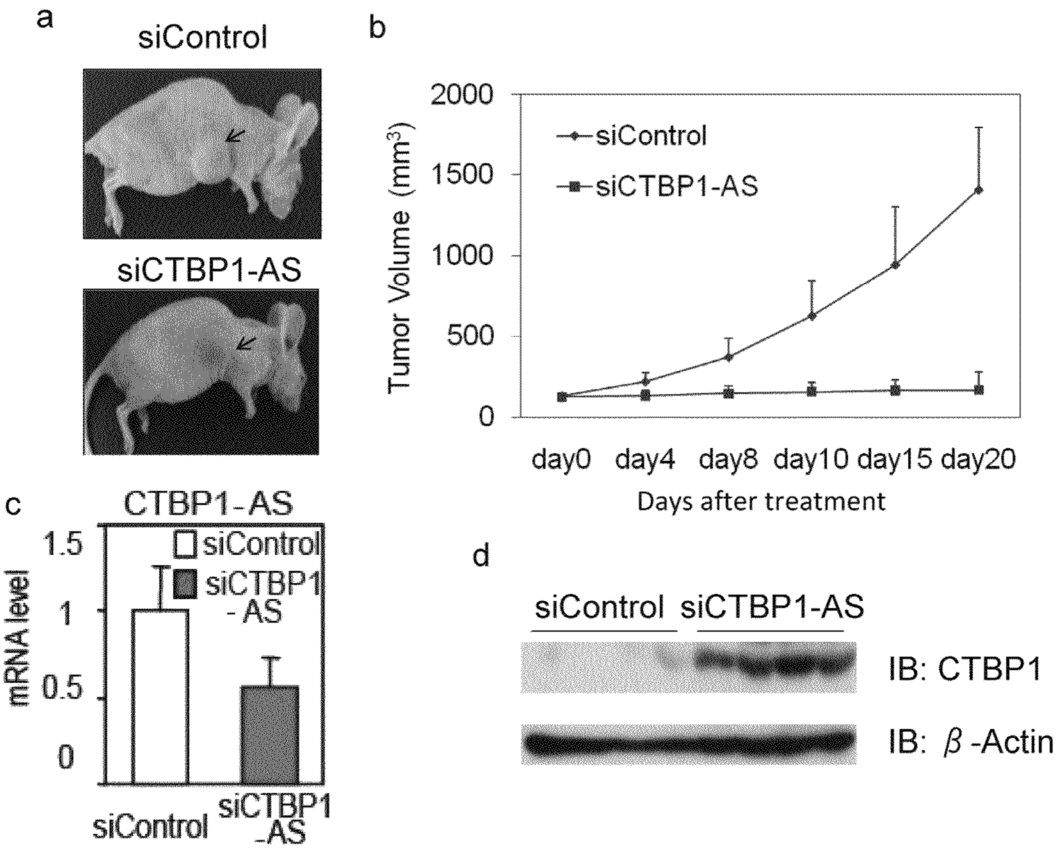

The results are shown in FIG. 16. Even in vivo, by suppressing expression of CTBP1-AS, an increase in the volume of the androgen-depletion resistant tumor was suppressed (FIGS. 16*a* and 16*b*). As a result of measurement of the expression amount of CTBP1-AS in tumor by qRT-PCR, decrease in the mRNA level expression has been confirmed (FIG. 16*c*). On the other hand, CTBP1 in tumor was measured by western blotting. Due to knock down of CTBP1-AS, the expression amount of CTBP1 increased (FIG. 16*d*).

<Involvement of RNA-Binding Protein PSF in Expression Suppression of CTBP1>

Expression of three genes, that is, PSF, NONO, and Sin3A was suppressed by RNAi. LNCaP cells were transfected with siRNAs against PSF, NONO, and Sin3A. Two days later, lysates were collected and the expression amount was examined by western blotting. It has been confirmed that any of the siRNAs specifically suppressed the target expression.

LNCaP cells were treated with ethanol or R1881 for 24 hours and two days before stimulation, the resulting cells were transfected with control siRNA or siRNA against PSF. The RNA was collected, cDNA was synthesized, and an expression amount of CTBP1 was analyzed by RT-PCR.

Figure 17:
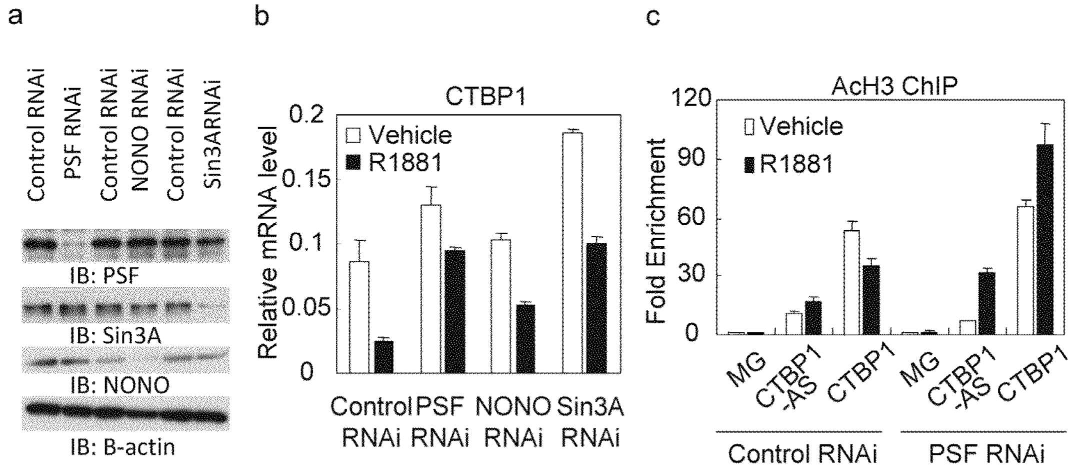
FIG. 17 shows the results of experiments to confirm the involvement of PSF, an RNA-binding transcriptional repressor, in expression suppression of CTBP1. When transcription of PSF was suppressed by RNAi, the suppression degree of CTBP1 expression by androgen stimulation decreased.

The results are shown in FIG. 17*b*. When the expression of PSF was suppressed, the suppression degree of CTBP1 expression by stimulation with androgen decreased.

In addition, ChIP was conducted using an ACH3 antibody. A histone acetylation level of a promoter region of CTBP1 and CTBP1-AS was measured using the real time PCR, followed by correction with GAPDH. The myoglobin exon region was used as a negative control.

The results are shown in FIG. 17*c*. When the expression of PSF was suppressed, the suppression degree of CTBP1 expression by stimulation with androgen decreased. This has suggested a promoter-level involvement of PSF in CTBP1 expression.

<Androgen-Dependent Binding of PSF to CTBP1-AS>

PSF is a RNA-binding transcriptional repressor. The presence or absence of binding between PSF and CTBP1-AS was analyzed.

LNCaP cells were treated with ethanol or R1881 for 24 24 hours and two days before stimulation, the resulting cells were transfected with control siRNA or siRNA against PSF. After a nuclear compartment was extracted and a lysate was collected, immunoprecipitation was conducted using an antibody specific to Norman IgG, PSF and NONO. Immunoprecipitation was conducted using Protein G and after washing, RNA was extracted using Isogen. A reverse transcription reaction was performed using total RNA and expression amounts of GAPDH, Myoglobin (MG), and CTBP1-AS were measured using the real time RT-PCR.

Figure 18:
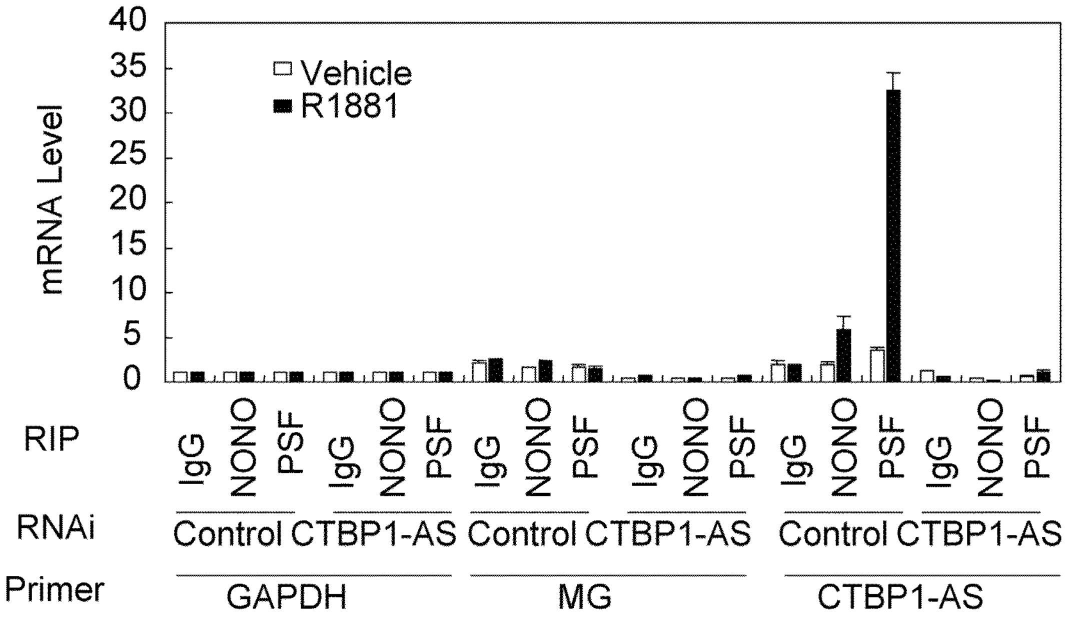

The results are shown in FIG. 18. It has been confirmed that CTBP1-AS binds to PSF in an androgen-dependent manner.

<Analysis of CTBP1-AS Localization by RNA-FISH>

Intranuclear localization of PSF and CTBP1-AS was analyzed. Ethanol or R1881 was added to LNCaP cells, followed by reaction for 24 hours. Then, RNA FISH of CTBP1-AS was performed. After fixed with formalin and methanol, the cells were reacted overnight at 42° C. for binding by using a probe against DIG-labeled CTBP1-AS. On the following day, a fluorescence-labeled antibody against DIG was bound and after washing, immunostaining with an anti-PSF antibody was performed. A second antibody against a mouse antibody was reacted for detection. The nucleus was stained with DAPI.

Figure 19:
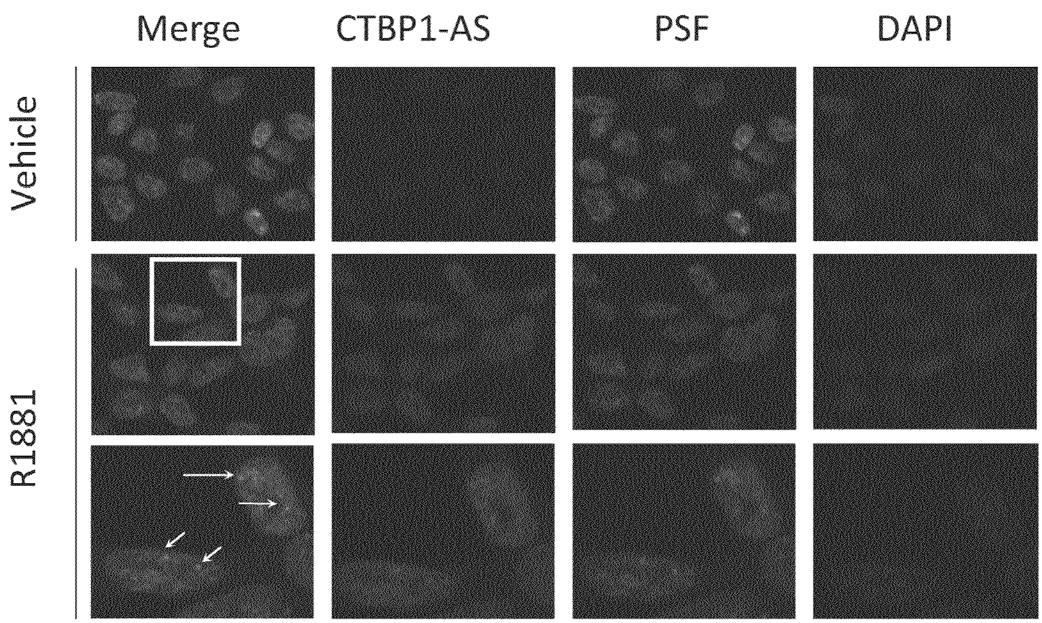

The results are shown in FIG. 19. PSF and CTBP1-AS showed almost the same localization, suggesting that they have been bound to each other.

<Control of Cell Cycle by PSF>

Next, another gene whose transcription was suppressed by PSF was searched.

Figure 20:
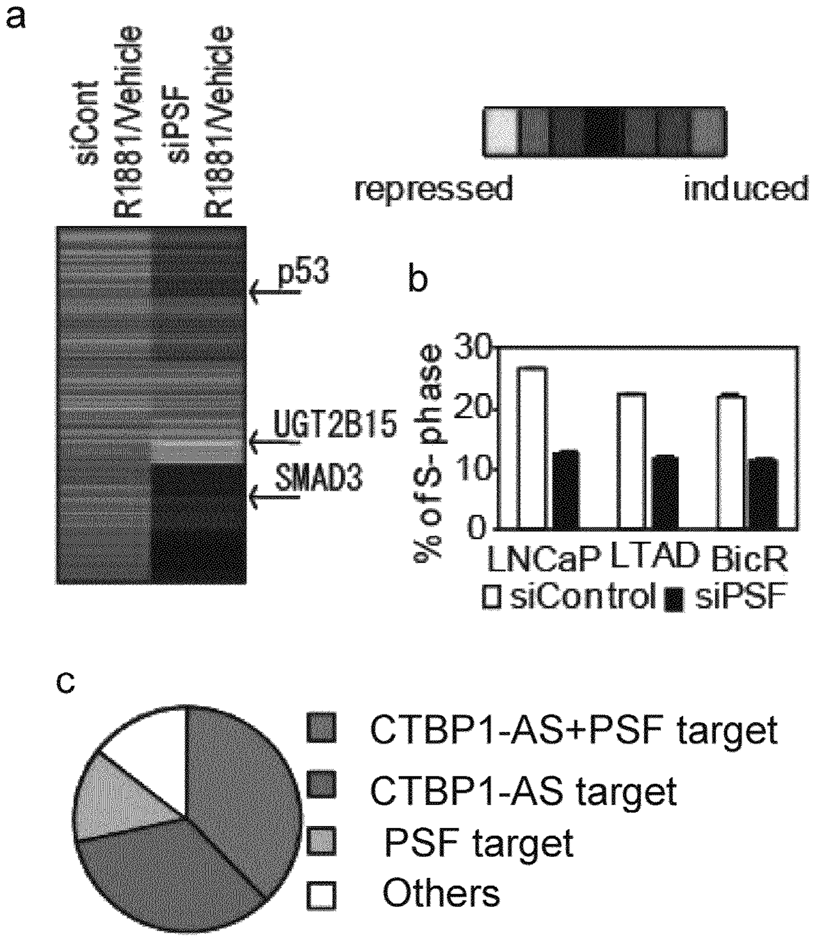
FIG. 20 shows the results of analyzing the relationship between PSF and cell cycle.

Cells were transfected with control siRNA or siRNA against PSF. Twenty four hours after stimulation with ethanol or R1881, RNA was collected. The RNA was amplified and gene expression was analyzed using a microarray. From an expression-suppressed gene group and an expression-enhanced gene group, a gene whose change was suppressed by androgen was extracted. A change rate of gene expression caused by androgen was Log 2 transformed and a Heat map was created using Cluster and Tree view (FIG. 20*a*). Suppressed transcription is shown with a lighter color.

70% of the gene suppressed by androgen was released from the suppression by siPSF. Moreover, induction of most of the androgen-mediated genes was suppressed by siPSF. This suggests that PSF widely mediates the expression suppression by androgen.

The gene group in which PSF was engaged in androgen action was subjected to pathway analysis. It has been found as a result of analysis of the gene group whose change was suppressed by PSF suppression, among the gene groups suppressed by androgen, that genes involved in cell cycle such as p53 and SMAD3 were concentrated (in the drawing, UGT2B15 is a negative control whose expression is suppressed by androgen but is not influenced by PSF).

Next, an influence of suppression by PSF on the cell cycle was analyzed using FACS. LNCaP cells, LTAD cells, and BicR cells were transfected with control siRNA or siRNA against PSF and 96 hours later, the cells were collected. The cell cycle was analyzed using FACS. A change in the percentage of S-phase cell fraction is shown in FIG. 20*b*. When PSF was knocked down, the tendency to decrease in the percentage of the DNA synthesis S-phase and retardation of the cell cycle were found.

A similar test to that in FIG. 20*a* was conducted except that CTBP1-AS, instead of PSF, was knocked down and kinds of genes to be released from the androgen-mediated suppression were compared. The results are shown in FIG. 20*c*. About 50% of the cells to be released from the androgen-mediated suppression by knockdown of PSF showed a tendency of being released from the androgen-mediated suppression even by knockdown of CTBP1-AS. This suggests that CTBP1-AS and PSF are cooperatively involved in androgen-mediated suppression of gene expression.

<Analysis of p53 and SMAD3, Target Genes of PSF>

Influence of PSF on the expression of p53 and SMAD3 was analyzed.

Figure 21:
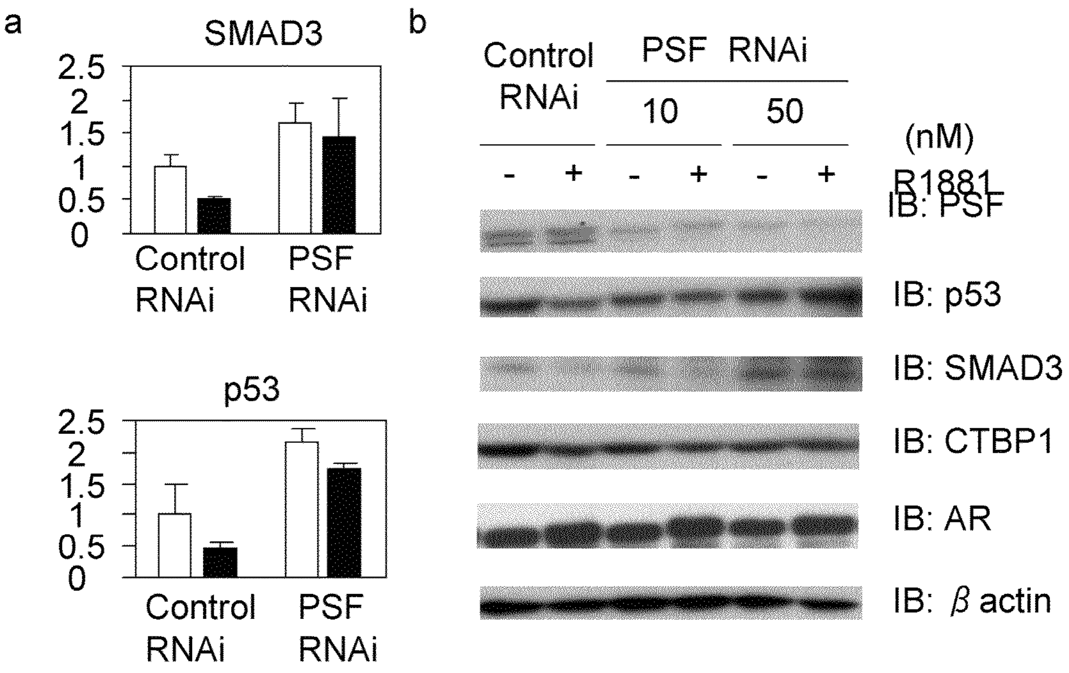
FIG. 21 shows the results of analyzing PSF-mediated control of SMAD3 and p53 by using siRNA against PSF through qRT-PCR (a) and western blotting (b).

LNCaP cells were transfected with control siRNA or siRNA against PSF and 48 hours after the transfection, they were stimulated with ethanol or R1881. Twenty four hours later, RNA and protein were collected. Measurement results of the expression amount of p53 and SMAD3 by qRT-PCR are shown in FIG. 21*a* (corrected by GAPDH). The results of western blotting are shown in FIG. 21*b* (β actin was used as Loading control).

Stimulation with androgen decreased both the mRNA level expression and protein level expression of SMAD3 and p53. When expression of PSF was suppressed, the androgen-mediated suppression of expression tended to be released. This suggests that SMAD3 or p53 is hardly influenced by androgen without PSF, in other words, suppression of SMAD3 or p53 expression by androgen is mediated by PSF.

<Androgen-Dependent Expression Suppression of Cell-Cycle-Related Factors by CTBP1-AS>

The influence of CTBP1-AS on the expression of p53 and SMAD3 was analyzed.

Figure 22:
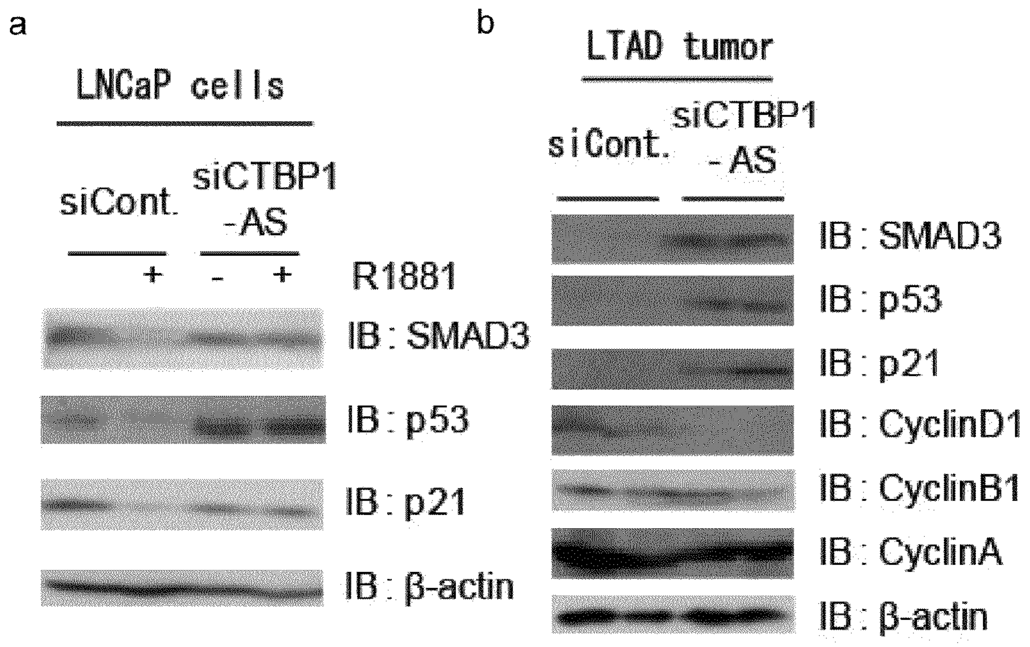

LNCaP cells were transfected with control siRNA or siRNA against CTBP1-AS and 48 hours later, they were stimulated with ethanol or androgen. Forty eight hours later, RNA and protein were collected and the expression amounts of p53, p21, and SMAD3 were analyzed by western blotting. The results are shown in FIG. 22*a*.

Expression of each of p53, p21, and SMAD3 was decreased by stimulation with androgen, but a decreasing degree was reduced by suppressing the expression of CTBP1-AS.

LTAD cells, that is, hormone-depletion resistant prostate cancer cells were transplanted to nude mice. After formation of a tumor, their testis was excised and locally injected with control siRNA or siRNA against CTBP1-AS. Three weeks later, the tumor was excised, protein was collected, and the expression amount of a cell cycle-related gene product was analyzed by western blotting. The results are shown in FIG. 22*b* (each, n=2). Suppression of the expression of CTBP1-AS led to release of androgen-dependent expression suppression of the cell cycle-related gene product.

Figure 23:
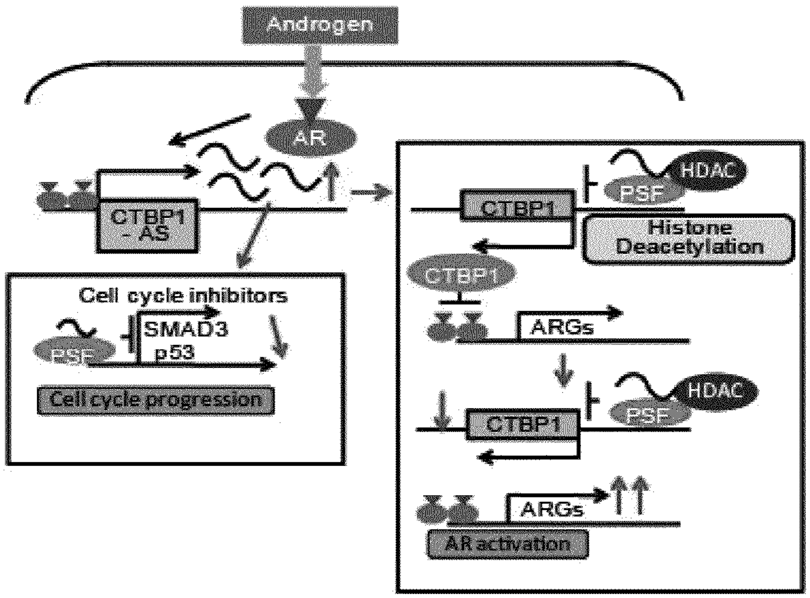
FIG. 23 is an explanatory view showing a gene expression control mechanism by CTBP1-AS and PSF.

FIG. 23 is a schematic view showing a gene expression control mechanism by CTBP1-AS and PSF which is suggested by the above results.

First, when androgen binds to an androgen receptor AR, transcription of CTBP1-AS increases.

As a result, in a global genome region (within the left framework in the drawing), CTBP1-AS binds to PSF to form a complex and this complex suppresses expression of SMAD3 or p53. SMAD3 or p53 is a cell cycle inhibiting gene so that when its expression is suppressed, cell proliferation is promoted.

On the other hand, locally (within the right framework in the drawing), when transcription of CTBP1-AS increases, a complex of CTBP1-AS and PSF binds to a histone deacetylation enzyme (HDAC) and suppresses transcription of CTBP1. Since CTBP1 is a transcription suppressor of an androgen receptor, suppression of the transcription of CTBP1 increases the transcription of the androgen receptor and activates the receptor.

Thus, either globally or locally, an increase in the transcription of CTBP1-AS serves to cause proliferation of cancer cells. This mechanism has proved that suppression of CTBP1-AS or PSF leads to suppression of the proliferation of cancer cells.

<Expression Suppression of CTBP1-AS by siRNA>

After designing and synthesizing siRNAs against CTBP1-AS shown in the following table, their effect on the expression suppression of CTBP1-AS was measured.

TABLE 5

| Oligo name | Target sequence (target sequence for designing siRNA) | SEQ ID NO. | >sense_strand | SEQ ID NO. | >antisense_strand | SEQ ID NO. |
|---|---|---|---|---|---|---|
| No. 1 | accaacaggaaacgtcctactta | 24 | CAACAGGAAACGUCCUACUUA | 53 | AGUAGGACGUUUCCUGUUGGU | 79 |
| No. 2 | ctcaacatcagaccaattaatta | 25 | CAACAUCAGACCAAUUAAUUA | 54 | AUUAAUUGGUCUGAUGUUGAG | 80 |
| No. 3 | accaactgtcaagaaacaattag | 26 | CAACUGUCAAGAAACAAUUAG | 55 | AAUUGUUUCUUGACAGUUGGU | 81 |
| No. 4 | ctcactgctgctgatgattgtag | 27 | CACUGCUGCUGAUGAUUGUAG | 56 | ACAAUCAUCAGCAGCAGUGAG | 82 |
| No. 5 | gacataccacacaaacactgatc | 28 | CAUACCACACAAACACUGAUC | 57 | UCAGUGUUUGUGUGGUAUGUC | 83 |
| No. 6 | gaccaattaattagaccacaaaa | 29 | CCAAUUAAUUAGACCACAAAA | 58 | UUGUGGUCUAAUUAAUUGGUC | 84 |
| No. 7 | tcccacatcaacacggtaacacc | 30 | CCACAUCAACACGGUAACACC | 59 | UGUUACCGUGUUGAUGUGGGA | 85 |
| No. 8 | cacccggcctaacatggagaatt | 31 | CCCGGCCUAACAUGGAGAAUU | 60 | UUCUCCAUGUUAGGCCGGGUG | 86 |
| No. 9 | acccggcctaacatggagaattt | 32 | CCGGCCUAACAUGGAGAAUUU | 61 | AUUCUCCAUGUUAGGCCGGGU | 87 |
| No. 10 | ggcctcataacgcactaggataa | 33 | CCUGAUAACGCACUAGGAUAA | 62 | AUCCUAGUGCGUUAUGAGGCC | 88 |
| No. 11 | aacgctgtgggatatgaggttgg | 34 | CGCUGUGGGAUAUGAGGUUGG | 63 | AACCUCAUAUCCCACAGCGUU | 89 |
| No. 12 | cccggcctaacatggagaattta | 35 | CGGCCUAACAUGGAGAAUUUA | 64 | AAUUCUCCAUGUUAGGCCGGG | 90 |
| No. 13 | gcctaacatggagaatttagaac | 36 | CUAACAUGGAGAAUUUAGAAC | 65 | UCUAAAUUCUCCAUGUUAGGC | 91 |
| No. 14 | tcctacttaatggtgaaatgtca | 37 | CUACUUAAUGGUGAAAUGUCA | 66 | ACAUUUCACCAUUAAGUAGGA | 92 |
| No. 15 | ctctatactattaataacagaca | 38 | CUAUACUAUUAAUAACAGACA | 67 | UCUGUUAUUAAUAGUAUAGAG | 93 |
| No. 16 | gcctcataacgcactaggataac | 39 | CUCAUAACGCACUAGGAUAAC | 68 | UAUCCUAGUGCGUUAUGAGGC | 94 |
| No. 17 | ttctcccacatcaacacggtaac | 40 | CUCCCACAUCAACACGGUAAC | 69 | UACCGUGUUGAUGUGGGAGAA | 95 |
| No. 18 | gcctcggcctcataacgcactag | 41 | CUCGGCCUCAUAACGCACUAG | 70 | AGUGCGUUAUGAGGCCGAGGC | 96 |
| No. 19 | tgctgctgatgattgtagctaat | 42 | CUGCUGAUGAUUGUAGCUAAU | 71 | UAGCUACAAUCAUCAGCAGCA | 97 |
| No. 20 | aggaactaactctatactattaa | 43 | GAACUAACUCUAUACUAUUAA | 72 | AAUAGUAUAGAGUUAGUUCCU | 98 |
| No. 21 | cactaagcagagtataggttaaa | 44 | CUAAGCAGAGUAUAGGUUAAA | 73 | UAACCUAUACUCUGCUUAGUG | 99 |
| No. 22 | ttaacacctgattaatataaaag<br>(ttgacacctgattaatataaaag) | 45<br>(46) | GACACCUGAUUAAUAUAAAAG | 74 | UUUAUAUUAAUCAGGUGUCAA | 100 |
| No. 23 | tgaacactcaagaggcaaagact<br>(tggacactcaagaggcaaagact) | 47<br>(48) | GACACUCAAGAGGCAAAGACU | 75 | UCUUUGCCUCUUGAGUGUCCA | 101 |
| No. 24 | gaccgtctaaacgcactacatcc | 49 | CCGUCUAAACGCACUACAUCC | 76 | AUGUAGUGCGUUUAGACGGUC | 102 |
| No. 25 | cccgcgaacgtggtgtctcctgc | 50 | CGCGAACGUGGUGUCUCCUGC | 77 | AGGAGACACCACGUUCGCGGG | 103 |
| No. 26 | tgacaacaagtgtggatgtaaac<br>(tggcaacaagtgtggatgtaaac) | 51<br>(52) | GCAACAAGUGUGGAUGUAAAC | 78 | UUACAUCCACACUUGUUGCCA | 104 |

Figure 24:
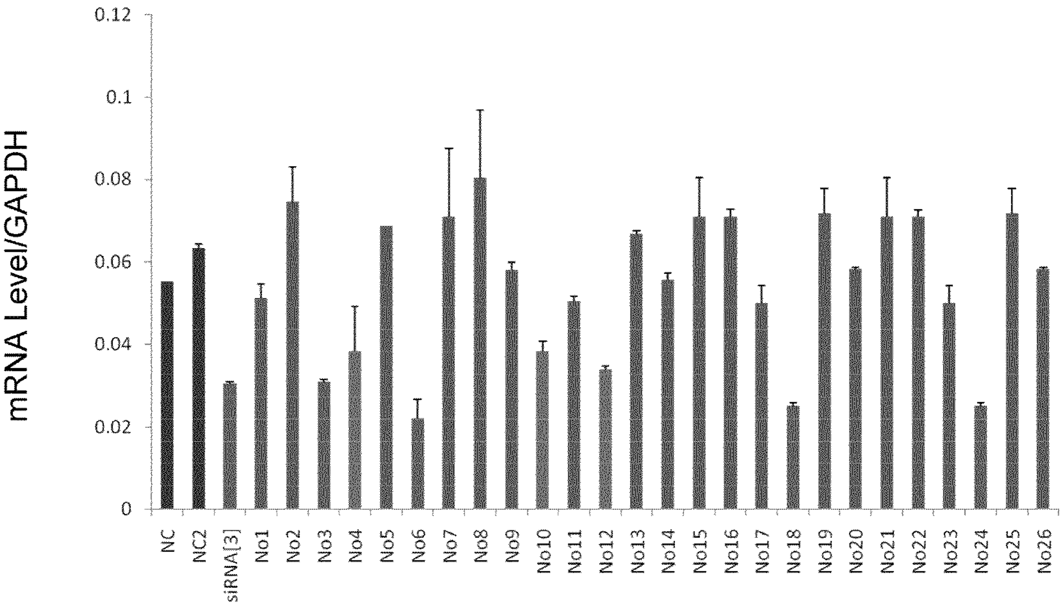
FIG. 24 shows the results of studying the CTBP1-AS expression suppression effect of 26 siRNAs.

The results are shown in FIG. 24. In this drawing, NC and NC2 are negative controls. It has been confirmed that compared with the negative controls, siRNAs of Nos. 3, 4, 6, 10, 12, 18, and 24 suppress the transcription of CTBP1-AS.

II. The Cell Growth Inhibitor Containing PSF Expression Inhibitor or Function Inhibitor Cell Line Human prostate cancer cell line LNCaP was grown in RPMI-1640 supplemented with 10% FBS, 100 U/ml penicillin, and 100 μg/ml streptomycin. Cells were incubated at 37 deg C. in an atmosphere including 5% $CO_2$.

Design of siRNA siRNAs targeting PSF was purchased from SIGMA (St. Louis, Mo.). These siRNAs were designed by the inventors' program so that the sense oligonucleotides would not induce off-target effect. SiRNA sequences designed by this program have previously been used successfully for the biological experiments in vivo. We determined that the siRNA sequences against PSF by surveying all other annotated genes so that the siRNA sequences would not match the gene sequences and confirmed that the possibility of off-target effect was low. The negative control siRNA (siControl) did not have off-target effects on other mammalian genes. The knockdown effects were evaluated using prostate cancer cells and the siRNA sequence showing most efficient RNAi effect was selected for the xenograft experiment.

The siRNAs used for the following Examples are listed below.

| siPSF # | Sense strand (5'->3') 21mer | Antisense strand (5'->3') 21mer | Target sequence | |
|---|---|---|---|---|
| 1 | GCACGUUUGAGUACGAAUAUU (SEQ ID NO: 119) | UAUUCGUACUCAAACGUGCCA (SEQ ID NO: 127) | 1542-1564* | CDS** |
| 2 | GGCACGUUUGAGUACGAAUAU (SEQ ID NO: 120) | AUUCGUACUCAAACGUGCCAU (SEQ ID NO: 128) | 1541-1563 | CDS |
| 3 | GCAUAUUAGGCUACGUAUUCC (SEQ ID NO: 121) | AAUACGUAGCCUAAUAUGCAU (SEQ ID NO: 129) | 2586-2608 | 3'UTR |
| 4 | GAUGAUCGUGGAAGAUCUACA (SEQ ID NO: 122) | UAGAUCUUCCACGAUCAUCCA (SEQ ID NO: 130) | 1304-1326 | CDS |
| 5 | GGGAGAUCCCUAUGGUUCAGG (SEQ ID NO: 123) | UGAACCAUAGGGAUCUCCCAU (SEQ ID NO: 131) | 1951-1973 | CDS |
| 6 | GUUUGGGCAGGUAAAAUUAUG (SEQ ID NO: 124) | UAAUUUUACCUGCCCAAACAG (SEQ ID NO: 132) | 2355-2377 | 3'UTR |
| 7 | CAUAGGUUAUGAAGCUAAUCC (SEQ ID NO: 125) | AUUAGCUUCAUAACCUAUGCC (SEQ ID NO: 133) | 2008-2030 | CDS |
| 8 | GGCAUAGGUUAUGAAGCUAAU (SEQ ID NO: 126) | UAGCUUCAUAACCUAUGCCAC (SEQ ID NO: 134) | 2006-2028 | CDS |

*base number

**CDS = coding sequence, 3'UTR = 3' untranslated region

Transfection of siRNA to Cells and mRNA Expression Analysis

LNCaP cells were plated at $3\times10^5$ cellsper well on 6 well plates. The next day, the cells were transfected with siRNAs (10 nM) using Lipofectamine RNAi Max reagent (Invitrogen, Carlsbad, Calif.) 72 hours before experiments. Total RNA was isolated using ISOGEN reagent (NIPPON Gene, Tokyo, Japan). Using 500 ng RNA as template, first-strand cDNA was synthesized using the Primescript RT reagent kit (TaKaRa Bio) according to manufacturer's protocol.

mRNA was quantified by real-time-PCR using the synthesized cDNA (2 μl of ten times dilution) by KAPA SYBR Fast qPCR Kit (NIPPON Genetics, Tokyo, Japan) and StepOne real-time PCR system (Life technologies, Tokyo, Japan) based on SYBR green fluorescence. The evaluation of relative differences of PCR product amounts among the treatment groups was carried out by the comparative cycle threshold (Ct) method, using glyceraldehyde-3-phosphate dehydrogenase as an internal control.

Figure 25:
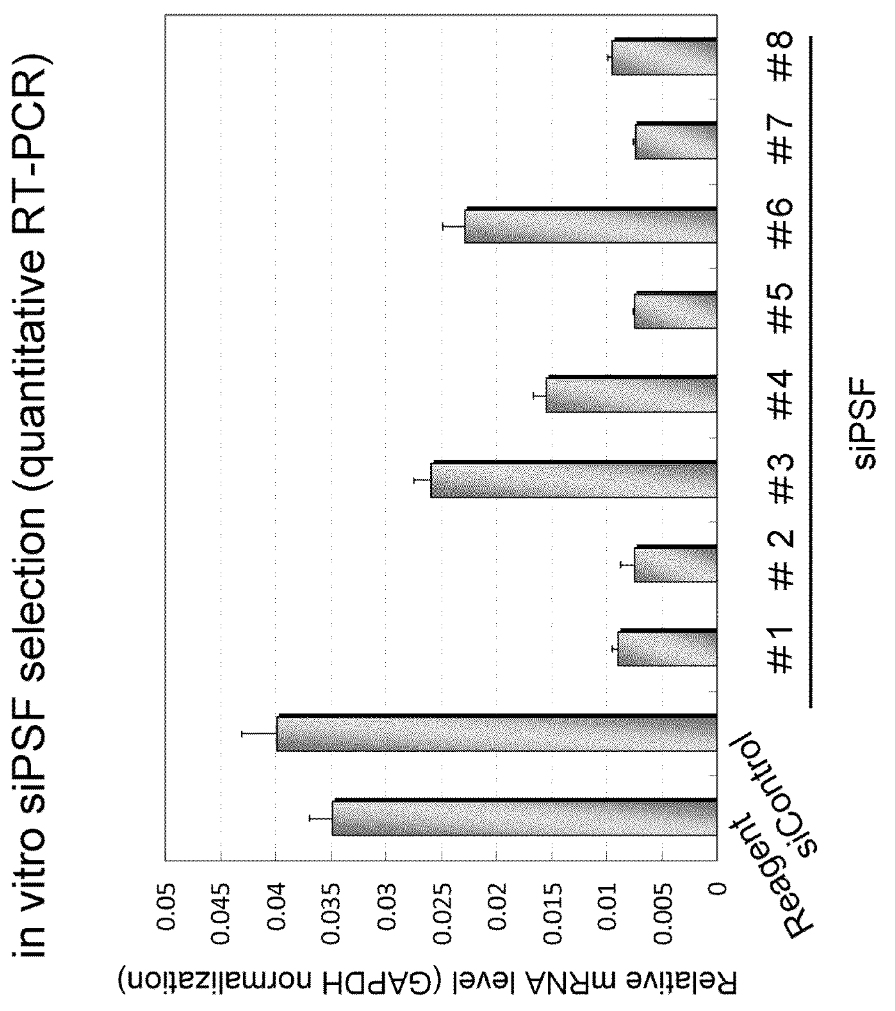
FIG. 25 shows the results of experiments to determine the expression amount of PSF after each siRNA against PSF or control siRNA (siControl) has been introduced into LNCaP cells.

The results are shown in FIG. 25. Compared to siControl- or Reagent-administered group, PSF mRNA expression decreased in siPSF-administered group. The expression suppression effect of siPSF#1, 2, 5, 7, 8 was particularly high.

Cell Proliferation Assay (MTS Assay)

LNCaP Cells were plated at $3\times10^3$ cells per well on 96-well plates and cultured in RPMI-1640 containing 10% FBS. The next day, the cells were transfected with siRNAs targeting PSF (siPSFs) or negative control siRNA at the concentration mentioned above. 0, 3, and 5 days after transfection, MTS assays were carried out using cell titer reagent (Promega Corp., Madison, Wis.) according to the manufacturer's protocol. In short, the number of cells were measured by the dehydrogenase reaction converting a tetrazolium compound (MTS; 3-(4,5-dimethylthiazol-2-yl)-5-(3-carboxymethoxyphenyl)-2-(4-sulfophenyl)-2H-tetrazolium, inner salt]) by the electron coupling reagent PMS (phenazine methosulfate) into a formazan product. The quantity of formazan product was measured by the amount of 490 nm absorbance. The experiments were performed in quintuplicate.

Figure 26:
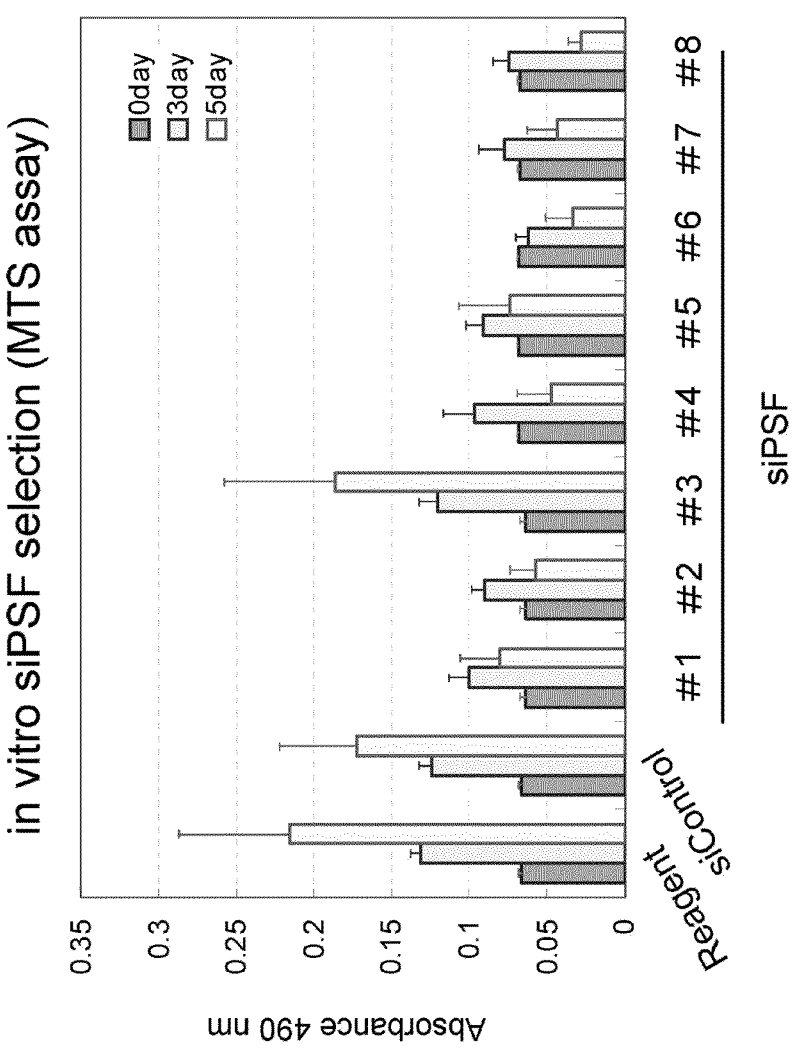
FIG. 26 shows the results of MTS assay after each siRNA against PSF or control siControl has been introduced into LNCaP cells.

The results are shown in FIG. 26. Time-dependent cell growth was observed in Reagent- or siControl-administered group. On the other hand, cell growth was suppressed in most siPSF-administered group.

Western Blot Analysis

Whole-cell lysates were prepared using NP40 lysis buffer [50 mM Tris-HCl (pH 8.0), 150 mM NaCl, 1% NP-40, and Protease inhibitor cocktail (Nacalai tesque, Kyoto, Japan)] and resolved in SDS lysis buffer. Lysates were electrophoresised by 8% SDS-PAGE and electroblotted onto Immobilon-P Transfer Membrane (Millipore Corp., Billerica, Mass.). Membranes were first incubated with primary antibody [anti-PSF (1:1000), anti-β-actin (1:1000)] and then with peroxidase-conjugated antimouse IgG antibody for 1 hour. After extensive washing, the antibodies were detected using enhanced ImmunoCruz Western blotting detector system (Santa Cruz Biotechnology, Inc).

Figure 27:
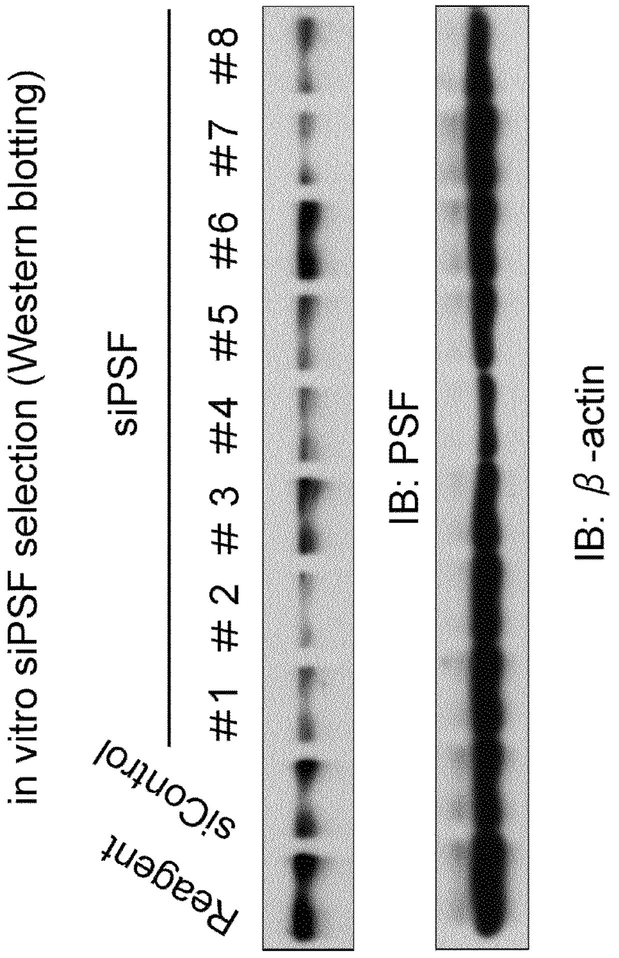
FIG. 27 shows the results of western blotting to determine the expression amount of PSF protein after each siRNA against PSF or siControl has been introduced into LNCaP cells.

The results are shown in FIG. 27. The expression of PSF protein was suppressed by the administration of siPSF#1, #2, #4, #5, #7, and #8.

Prostate Cancer Xenograft Model

Ten million cells in 100 μl PBS with 100 μl of Matrigel (BD Biosciences, San Jose, Calif.) were injected subcutaneously into each side of 6-week-old male BALB/c nude mice (Nihon Crea, Tokyo, Japan) using 25 G syringe. These mice were untreated until tumors could be observed.

Injection of siRNA into Tumors

When the volume of tumors reached approximately 100 $mm^3$ (i.e. in 4-8 weeks after injection), siControl (BannoNegaCon) or siPSF#2 was injected into the tumors two times per week (Control group n=5, siPSF group n=6). For the injection, 5 μg siRNA (per mouse) was mixed with 15 μl RNAi MAX in OPTI-MEM were used.

Measurements of Tumor Growth and Evaluation of PSF Expression

Tumors were measured with calipers two times per week. Tumor volume was determined using the formula 0.5×r1×r2×r3 (r1<r2<r3: three axes of tumor). Mice were killed by cervical dislocation 10 weeks after the transplantation. Animal care was maintained in accordance with institutional guidelines. Proteins were extracted by SDS lysis buffer (10 mM Tris-HCl PH7.5, 2% SDS, 10% 2-mercaptoethanol).

Figure 28:
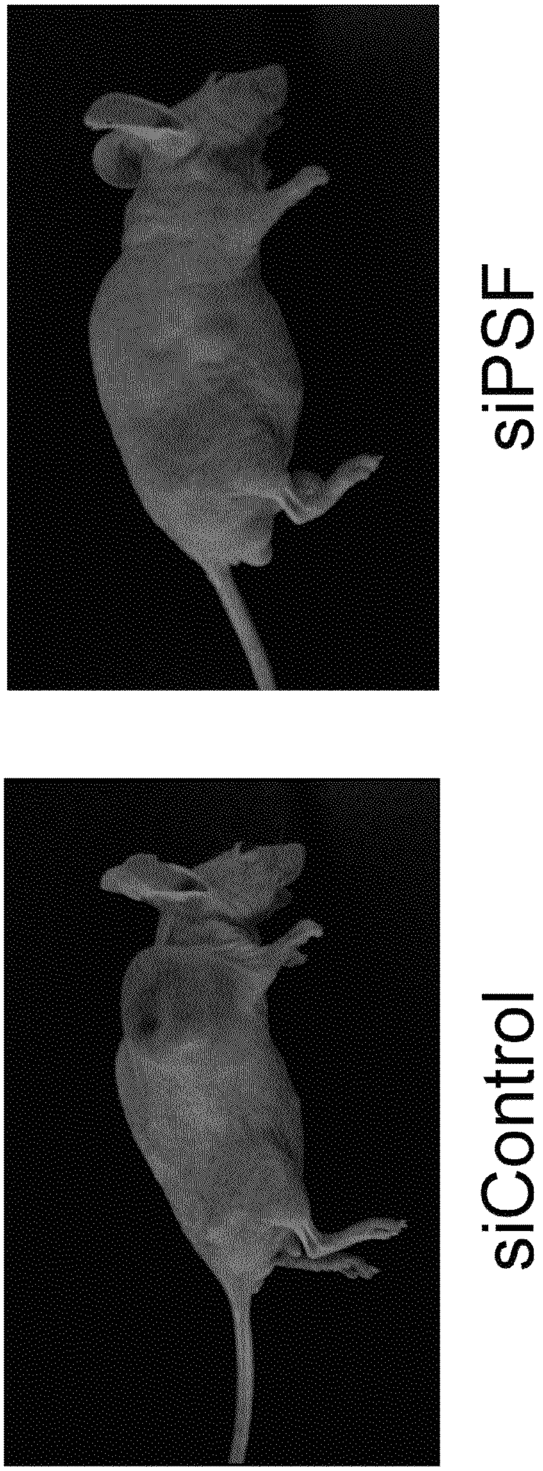
FIG. 28 shows the picture of mouse prostate cancer xenograft models five weeks after the administration of siPSF or siControl.
Figure 29:
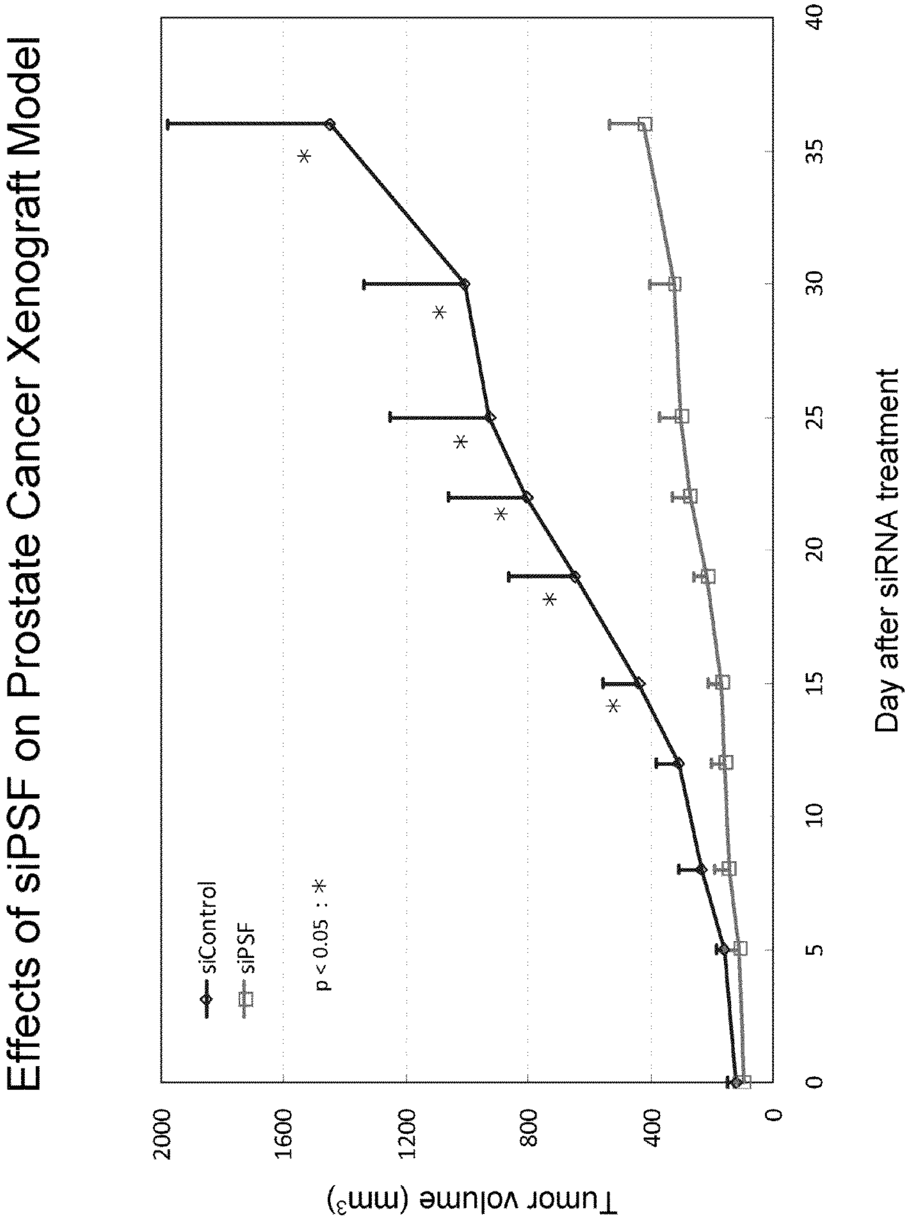
FIG. 29 shows the change of tumor volume in the prostate cancer xenograft models after the administration of siPSF or siControl.

The results are shown in FIGS. 28 and 29. The tumor growth in prostate cancer xenograft model was well suppressed by the administration of siPSF.

[Sequence Listing Free Text]

SEQ ID NO:1 is a base sequence in one mode of CTBP1-AS.

SEQ ID NO:2 is a base sequence of AX747592.

SEQ ID NO:3 is a base sequence of a target region of siRNA inhibiting the function of CTBP1-AS.

SEQ ID NO:4 is a base sequence of a target region of siRNA inhibiting the function of CTBP1-AS.

SEQ ID NO:5 is a base sequence of a target region of siRNA inhibiting the function of CTBP1-AS.

SEQ ID NO:6 is a base sequence of a target region of siRNA inhibiting the function of CTBP1-AS.

SEQ ID NO:7 is a base sequence of RNA constituting siRNA inhibiting the function of CTBP1-AS.

SEQ ID NO:8 is a base sequence of RNA constituting siRNA inhibiting the function of CTBP1-AS.

SEQ ID NO:9 is a base sequence of RNA constituting siRNA inhibiting the function of CTBP1-AS.

SEQ ID NO:10 is a base sequence of RNA constituting siRNA inhibiting the function of CTBP1-AS.

SEQ ID NO:11 is a base sequence of RNA constituting siRNA inhibiting the function of CTBP1-AS.

SEQ ID NO:12 is a base sequence of RNA constituting siRNA inhibiting the function of CTBP1-AS.

SEQ ID NO:13 is a base sequence of RNA constituting siRNA inhibiting the function of CTBP1-AS.

SEQ ID NO:14 is a base sequence of RNA constituting siRNA inhibiting the function of CTBP1-AS.

SEQ ID NO:15 is a base sequence of RNA constituting siRNA used as a control in siRNA in Examples.

SEQ ID NO:16 is a base sequence of RNA constituting siRNA used as a control in siRNA in Examples.

SEQ ID NO:17 is a base sequence of CTBP1-ASc.

SEQ ID NO:18 is a base sequence of CTBP1-ASb.

SEQ ID NO:19 is a base sequence of CTBP1-ASa.

SEQ ID NO:20 is a base sequence of CTBP1-ASd.

SEQ ID NO:21 is a base sequence of 3' Race primer used for 3' RACE PCR.

SEQ ID NO:22 is a base sequence of a PCR adaptor primer used for 3' RACE PCR.

SEQ ID NO:23 is a base sequence of a probe used in northern blotting of RNA derived from LNCaP cells.

SEQ ID NOS:24 to 52 are base sequences of a target region of siRNA inhibiting the function of CTBP1-AS.

SEQ ID NOS:53 to 104 are base sequences of RNA constituting siRNA inhibiting the function of CTBP1-AS.

SEQ ID NOS:105 to 108 are base sequences of a primer used in real time PCR.

SEQ ID NO:109 to 118 are base sequences of a primer used in real time RT-PCR.

SEQ ID NO:119 is a base sequence of sense strand of siPSF#1.

SEQ ID NO:120 is a base sequence of sense strand of siPSF#2.

SEQ ID NO:121 is a base sequence of sense strand of siPSF#3. SEQ ID NO:122 is a base sequence of sense strand of siPSF#4.

SEQ ID NO:123 is a base sequence of sense strand of siPSF#5.

SEQ ID NO:124 is a base sequence of sense strand of siPSF#6.

SEQ ID NO:125 is a base sequence of sense strand of siPSF#7.

SEQ ID NO:126 is a base sequence of sense strand of siPSF#8.

SEQ ID NO:127 is a base sequence of antisense strand of siPSF#1.

SEQ ID NO:128 is a base sequence of antisense strand of siPSF#2.

SEQ ID NO:129 is a base sequence of antisense strand of siPSF#3.

SEQ ID NO:130 is a base sequence of antisense strand of siPSF#4.

SEQ ID NO:131 is a base sequence of antisense strand of siPSF#5.

SEQ ID NO:132 is a base sequence of antisense strand of siPSF#6.

SEQ ID NO:133 is a base sequence of antisense strand of siPSF#7.

SEQ ID NO:134 is a base sequence of antisense strand of siPSF#8.

The invention claimed is:

1. A cell growth inhibitor comprising a PSF (PTB-associated splicing factor) expression inhibitor or function inhibitor as an active ingredient, wherein the PSF expression inhibitor or function inhibitor is a double-stranded RNA which inhibits expression of PSF, and one strand of the double-stranded RNA comprises a sequence represented by any of SEQ ID NO: 121, 122, 123, and 124.

2. The cell growth inhibitor according to claim 1, wherein the cell growth inhibitor inhibits the growth of the cells that express C-terminal binding protein 1-antisense (CTBP1-AS) comprising a base sequence of any of SEQ ID NO: 17 to 20.

3. The cell growth inhibitor according to claim 2, wherein the cells that express CTBP1-AS are prostate cancer cells and/or metastatic cancer cells thereof.

4. A method of treating prostate cancer in a subject, comprising administering a therapeutically effective amount of the cell growth inhibitor of claim 1 to the subject.

5. The cell growth inhibitor according to claim 1, wherein one strand of the double-stranded RNA consists of a sequence represented by any of SEQ ID NO: 121, 122, 123, and 124.

6. A method of treating prostate cancer in a subject, comprising administering a therapeutically effective amount of the cell growth inhibitor of claim 5.

7. The method according to claim 4, wherein the administering comprises contacting the cell growth inhibitor of claim 1 to a cell expressing (i) an antisense RNA to a CTBP1 (C-terminal binding protein 1) gene comprising from position 2348 to position 2372 of the base sequence represented by SEQ ID NO: 1; or (ii) a mutant or variant of the antisense RNA having a sequence that is 90% identical to from position 2348 to position 2372 of the base sequence represented by SEQ ID NO: 1.

8. The method according to claim 4, wherein the cell growth inhibitor inhibits the growth of the cells that express C-terminal binding protein 1-antisense (CTBP1-AS), comprising a base sequence of any of SEQ ID NOs: 17 to 20.

9. The method according to claim 8, wherein the cells that express CTBP1-AS are prostate cancer cells and/or metastatic cancer cells thereof.

10. The cell growth inhibitor according to claim 1, wherein the one strand of the double-stranded RNA comprises a sequence represented by any of SEQ ID NO: 121, 123, and 124.

* * * * *

SEQUENCE LISTING

```
<160> NUMBER OF SEQ ID NOS: 134

<210> SEQ ID NO 1
<211> LENGTH: 3885
<212> TYPE: RNA
<213> ORGANISM: Homo sapiens
<220> FEATURE:
```

<221> NAME/KEY: misc_feature
<223> OTHER INFORMATION: nucleic acid sequence of an example of CTBPA-AS

<400> SEQUENCE: 1
agggcuugcc uguggagagg cuggagucag ccgucagcgc ggaacuccug gucuucccac 60
ugccaccucu gcagcccccca ccagagauau cagaaaacau cagcuccagc cugcagccca 120
gacacuugaa gucaccuugg cugccccucc ucacacccgu gcccacguca gcaaaaccag 180
ggccggcuug uuaaccgugu ccagaaccca cccuucccac ccugcccagg ccaccucccu 240
caguggccca gggggcucca aguugaagag cccaagacag gucagagaug ggcugggcgg 300
ccucugccac ucaccuccgg agagggcagg gagcagaggc cucagucaug aggugggcu 360 guccucggcg ugggccucga gacugggagc cacugcccau acccaagaga ccucugcgag 420
cacuggggug cagagccagc ucugagaaac caggaggcug ggauuuugaa gaggacgccg 480
guaaacaggc ucagcugugg gccaaggaac gcgaaggaca cagggcagag cgcccacagg 540
acggacgacg acaagcgaca cgaggcccag cgcugccccc ucccgccucc ugacagcccg 600
gaccagucuc ugcagugcca gggccaccac acagaugccu ccuccacaca cucugguccg 660
aggguuuccg ggcccucugc ccaggcgccg aggcuggaga gcuccucccg ggccacaacu 720
ggucacuggc guggucucua uccgccucgg gcuugacggu uugaccagga gaaggggcgu 780
ggggcgggug ggccacaggg ggcaggccgu gggacaggga cauggcgcug gggacgauac 840
cuuccacagc agcugggaug ccagugggg ccacgcccac cacgcccgga ggguaccugc 900
ugggagaggg uccauccgug aggcccaccu guaggcggcc uggccaggcc ccaccugccc 960
uccuagcauc ggcagcaccg agggggccuc uccaggagga ccagcaguca gggccccgug 1020
cccauggcac uccuguguccc acugagcccu gaaggccacc ccagcccagg cuccuuccaa 1080
gaggcccugg uucucauggg ccuuucagcu gcagauguca gaggccgacc ugagcacagc 1140
ccuuuccagc ugcagauguc agaggccgac cugagcacag cccguuccag cugcagaugu 1200
gaaaccugaa ccuggcagca cggaagucac aagggccgac ccaacgcccc cagaaguaga 1260 guccugugu cccggcucca cgcaccugcu ugacggugaa gucguugaug agguggugguu 1320 ugugcucguu gaggccgcag ugcaggguca cgcagucgcu guggaagagc agguccugca 1380
gggugcugac acgcugcagc cccagcgccc gcuccacgcc auccgacaag uaagggucgu 1440
agaagagcac guugaagccg aaggccuugg cccgcagcgc cacugccugc ccccacgcgac 1500 cugguggcgu caagacacag ugugagaccc uugcucaccc guggccggga ggccggcccc 1560
gaaagccagg gucggagugg ccucugugcc ucaguuugac caucugccaa ggaugacacc 1620
agcugugguc aagccaaggu gcccacgcac gcuccacacg agcgcuccac guccgcucca 1680
acgcgcccac ugccaaggcg gaggagaugc acaggggugg aaaggguaca cuagccccuc 1740
ggcccacacc agcugccagc cacaccacuc cccugcagcc uguccacagg acgugacaug 1800
aaccacucag ugucaaacgg acuggucagu gggucuccac ccacccaaca cauguccucc 1860
gugcccaggc cccuccgcug gccuuucgau ccacccauca auguuuccgg caucucaauu 1920
ccagccacca cuacguggag acggcaaagg gggcaggagg gaaacuucca gaccagggag 1980
gccccgcugg gcucaggucc ugaccccuuc gaguggagcg gcagagaaag ccaucccagg 2040
cagacgugcc ugcccccacc ccagcagucc aaggcuggca cgggucccag cacaggagcc 2100
guggagcuug agccaccgug ucuggcuggg gccggcuccu ccucggggaa gggucugcag 2160
agugcucgug cccacuguga gccaacagca uggcugcaaa ggacacagga ccccaagccc 2220

```
gcgaacgugg ugucuccugc auugccucag agggaaccgc uacacaggaa ggaagcaggu   2280

ugagcgccgg ggcggguggg aagugggcgc aguuucaaag gcggcagcca gggcaggccu   2340

cccugagaag accaagcuug cuggagacau aaggggacag gaagggagcc agagagcugg   2400

aacaacacgu gcgaggggcc cgcggcggcc ugagggccaa ggagaccaga ccgccaggca   2460

cacagggugg ccggacgugg cccaaacgcc caggggaccc ccagucacuc ugggaagagg   2520

acugggggag gcugggaggc cagucagaag agcugaggac cgucuaaacg cacuacaucc   2580

uagaaaggga ggcgccuguu cuacgagaag gaacauggug gcuccuucca uccccaggga   2640

cgaggcugcu gcaggaggga ggagggcucg gcaggcggag gugggagcag caguucugag   2700

gguugcagcc acggccggag uacccgggca gcuccccagg ugcagaacag cccgucuguc   2760

aacgcccccu gccagggauc ccaccaaaug gggaggaaga gaacacaggc agacacagag   2820

aaaggcgucu cccacagcgc agaaggcgga cgacacgcug uuucccacug cgcacaacac   2880

aaagccccgg aagucgggcu gccgguggcg aaaaccagcu aaagccgcgg gccggcgccg   2940

gccacgccug acacgggaga gcagcggcug uucggggcga gaccauucuu cacuucuguc   3000

ucugccauuc ucuuccacau gaugucuggc uuaggauaag aaauuaugau gaugcaggug   3060

aagagacagg aggauguagu uucuaauuag aacaaaacac uggaagcgga cagacgcaca   3120

gaugaccgag gcuggaauca gccagcaaaa ccucuuaaua acuacuauaa acaugcucag   3180

agaugacaac aaguguggau guaaacagca gaaaaaugga ggcuuccgga agaugaaugg   3240

uaacucuaua aagaaccaca uagaaauucc agaacgaaaa caucccucug aaacggaacu   3300

cccuggacaa agcuaacugc aagaaaagga ucgggagcuu gaagggaggg gcucaaaguc   3360

agcagauggc auccaaacag aagcagagag aaaagaauuu aaaaaauaaa uuuuaaagaa   3420

caggccuugg uggcugacgc cuguaauccc agcacucugg gaggcugagg ugggcggauc   3480

acaaggucag gaguucgaga ccagccuggc caacauggug aaaccccguc ucuacuaaaa   3540

auacaaaaau uagccggacg ugguggcggg cgccuguagu ccaagcuacu cgggaggcug   3600

aggcaggaga auggcgugaa ccugggaagc agaggcugca gugagccgag aucgcgccac   3660

ugcacuccag acugggcgac agagcgagac uaccuuccac aaaaaaaaaa aggcaacaca   3720

uuuucggaca aagaaaagca aaaggaaucg gucacuggug agccacauuu cuaagacagu   3780

cuuuaggcua caggaacgug acgcccgagg acagccagaa ucggggggcg uaaacaaggc   3840

agaaagggug gaugugucgg uugauauuca aaagaaaaau uacug                   3885
```

```
<210> SEQ ID NO 2
<211> LENGTH: 3885
<212> TYPE: DNA
<213> ORGANISM: Homo sapiens
<220> FEATURE:
<221> NAME/KEY: misc_feature
<223> OTHER INFORMATION: nucleic acid sequence of AX747592

<400> SEQUENCE: 2

agggcttgcc tgtggagagg ctggagtcag ccgtcagcgc ggaactcctg gtcttcccac     60

tgccacctct gcagccccca ccagagatat cagaaaacat cagctccagc ctgcagccca    120

gacacttgaa gtcaccttgg ctgcccctcc tcacacccgt gcccacgtca gcaaaaccag    180

ggccggcttg ttaaccgtgt ccagaaccca cccttcccac cctgcccagg ccacctccct    240

cagtggccca gggggctcca agttgaagag cccaagacag gtcagagatg ggctgggcgg    300

cctctgccac tcacctccgg agagggcagg gagcagaggc ctcagtcatg aggtggggct    360
```

-continued

```
gtcctcggcg tgggcctcga gactgggagc cactgcccat acccaagaga cctctgcgag    420
cactggggtg cagagccagc tctgagaaac caggaggctg ggattttgaa gaggacgccg    480
gtaaacaggc tcagctgtgg gccaaggaac gcgaaggaca cagggcagag cgcccacagg    540
acggacgacg acaagcgaca cgaggcccag cgctgccccc tcccgcctcc tgacagcccg    600
gaccagtctc tgcagtgcca gggccaccac acagatgcct cctccacaca ctctggtccg    660
agggtttccg ggccctctgc ccaggcgccg aggctggaga gctcctcccg ggccacaact    720
ggtcactggc gtggtctcta tccgcctcgg gcttgacggt ttgaccagga gaaggggcgt    780
ggggcgggtg ggccacaggg ggcaggccgt gggacaggga catggcgctg ggacgatac     840
cttccacagc agctgggatg ccagtggggg ccacgcccac cacgcccgga gggtacctgc    900
tgggagaggg tccatccgtg aggcccacct gtaggcggcc tggccaggcc ccacctgccc    960
tcctagcatc ggcagcaccg agggggcctc tccaggagga ccagcagtca gggccccgtg   1020
cccatggcac tcctgtgtcc actgagccct gaaggccacc ccagcccagg ctccttccaa   1080
gaggccctgg ttctcatggg cctttcagct gcagatgtca gaggccgacc tgagcacagc   1140
cctttccagc tgcagatgtc agaggccgac ctgagcacag cccgttccag ctgcagatgt   1200
gaaacctgaa cctggcagca cggaagtcac aagggccgac ccaacgcccc cagaagtaga   1260
gtcctgtgtc cccggctcca cgcacctgct tgacggtgaa gtcgttgatg aggtggtggt   1320
tgtgctcgtt gaggccgcag tgcagggtca cgcagtcgct gtggaagagc aggtcctgca   1380
gggtgctgac acgctgcagc cccagcgccc gctccacgcc atccgacaag taagggtcgt   1440
agaagagcac gttgaagccg aaggccttgg cccgcagcgc cactgcctgc cccacgcgac   1500
ctggtggcgt caagacacag tgtgagaccc ttgctcaccc gtggccggga ggccggcccc   1560
gaaagccagg gtcggagtgg cctctgtgcc tcagtttgac catctgccaa ggatgacacc   1620
agctgtggtc aagccaaggt gcccacgcac gctccacacg agcgctccac gtccgctcca   1680
acgcgcccac tgccaaggcg gaggagatgc acaggggtgg aaagggtaca ctagcccctc   1740
ggcccacacc agctgccagc cacaccactc ccctgcagcc tgtccacagg acgtgacatg   1800
aaccactcag tgtcaaacgg actggtcagt gggtctccac ccacccaaca catgtcctcc   1860
gtgcccaggc ccctccgctg gcctttcgat ccacccatca atgtttccgg catctcaatt   1920
ccagccacca ctacgtggag acggcaaagg gggcaggagg gaaacttcca gaccagggag   1980
gccccgctgg gctcaggtcc tgaccccttc gagtggagcg gcagagaaag ccatcccagg   2040
cagacgtgcc tgcccccacc ccagcagtcc aaggctggca cgggtcccag cacaggagcc   2100
gtggagcttg agccaccgtg tctggctggg gccggctcct cctcggggaa gggtctgcag   2160
agtgctcgtg cccactgtga gccaacagca tggctgcaaa ggacacagga ccccaagccc   2220
gcgaacgtgg tgtctcctgc attgcctcag agggaaccgc tacacaggaa ggaagcaggt   2280
tgagcgccgg ggcgggtggg aagtgggcgc agtttcaaag gcggcagcca gggcaggcct   2340
ccctgagaag accaagcttg ctggagacat aaggggacag gaagggagcc agagagctgg   2400
aacaacacgt gcgagggggc cgcggcggcc tgagggccaa ggagaccaga ccgccaggca   2460
cacagggtgg ccggacgtgg cccaaacgcc caggggaccc ccagtcactc tgggaagagg   2520
actgggggag gctgggaggc cagtcagaag agctgaggac cgtctaaacg cactacatcc   2580
tagaaaggga ggcgcctgtt ctacgagaag gaacatggtg gctccttcca tccccaggga   2640
cgaggctgct gcaggaggga ggagggctcg gcaggcggag gtgggagcag cagttctgag   2700
ggttgcagcc acggccggag tacccgggca gctccccagg tgcagaacag cccgtctgtc   2760
```

```
aacgcccccct gccagggatc ccaccaaatg gggaggaaga gaacacaggc agacacagag   2820

aaaggcgtct cccacagcgc agaaggcgga cgacacgctg tttcccactg cgcacaacac   2880

aaagccccgg aagtcgggct gccggtggcg aaaaccagct aaagccgcgg gccggcgccg   2940

gccacgcctg acacgggaga gcagcggctg ttcggggcga gaccattctt cacttctgtc   3000

tctgccattc tcttccacat gatgtctggc ttaggataag aaattatgat gatgcaggtg   3060

aagagacagg aggatgtagt ttctaattag aacaaaacac tggaagcgga cagacgcaca   3120

gatgaccgag gctggaatca gccagcaaaa cctcttaata actactataa acatgctcag   3180

agatgacaac aagtgtggat gtaaacagca gaaaaatgga ggcttccgga agatgaatgg   3240

taactctata aagaaccaca tagaaattcc agaacgaaaa catccctctg aaacggaact   3300

ccctggacaa agctaactgc aagaaaagga tcgggagctt gaagggaggg gctcaaagtc   3360

agcagatggc atccaaacag aagcagagag aaaagaattt aaaaaataaa ttttaaagaa   3420

caggccttgg tggctgacgc ctgtaatccc agcactctgg gaggctgagg tgggcggatc   3480

acaaggtcag gagttcgaga ccagcctggc caacatggtg aaaccccgtc tctactaaaa   3540

atacaaaaat tagccggacg tggtggcggg cgcctgtagt ccaagctact cgggaggctg   3600

aggcaggaga atggcgtgaa cctgggaagc agaggctgca gtgagccgag atcgcgccac   3660

tgcactccag actgggcgac agagcgagac taccttccac aaaaaaaaaa aggcaacaca   3720

ttttcggaca aagaaaagca aaaggaatcg gtcactggtg agccacattt ctaagacagt   3780

ctttaggcta caggaacgtg acgcccgagg acagccagaa tcgggggcg taaacaaggc   3840

agaaagggtg gatgtgtcgg ttgatattca aaagaaaaat tactg                   3885
```

```
<210> SEQ ID NO 3
<211> LENGTH: 25
<212> TYPE: RNA
<213> ORGANISM: Homo sapiens
<220> FEATURE:
<221> NAME/KEY: misc_feature
<223> OTHER INFORMATION: target region of siRNA against CTBP1-AS
<220> FEATURE:
<221> NAME/KEY: misc_feature
<223> OTHER INFORMATION: an example of target region of siRNA against
      CTBP1-AS

<400> SEQUENCE: 3

cacucagugu caaacggacu gguca                                         25


<210> SEQ ID NO 4
<211> LENGTH: 25
<212> TYPE: RNA
<213> ORGANISM: Homo sapiens
<220> FEATURE:
<221> NAME/KEY: misc_feature
<223> OTHER INFORMATION: an example of target region of siRNA against
      CTBP1-AS

<400> SEQUENCE: 4

cccaucaaug uuuccggcau cucaa                                         25


<210> SEQ ID NO 5
<211> LENGTH: 25
<212> TYPE: RNA
<213> ORGANISM: Homo sapiens
<220> FEATURE:
<221> NAME/KEY: misc_feature
<223> OTHER INFORMATION: an example of target region of siRNA against
      CTBP1-AS
```

<400> SEQUENCE: 5
aagaccaagc uugcuggaga cauaa 25

<210> SEQ ID NO 6
<211> LENGTH: 25
<212> TYPE: RNA
<213> ORGANISM: Homo sapiens
<220> FEATURE:
<221> NAME/KEY: misc_feature
<223> OTHER INFORMATION: an example of target region of siRNA against CTBP1-AS

<400> SEQUENCE: 6
gagacaggag gauguaguuu cuaau 25

<210> SEQ ID NO 7
<211> LENGTH: 25
<212> TYPE: RNA
<213> ORGANISM: Artificial
<220> FEATURE:
<223> OTHER INFORMATION: one strand of siRNA[1]

<400> SEQUENCE: 7
ugaccagucc guuugacacu gagug 25

<210> SEQ ID NO 8
<211> LENGTH: 25
<212> TYPE: RNA
<213> ORGANISM: Artificial
<220> FEATURE:
<223> OTHER INFORMATION: one strand of siRNA[1]

<400> SEQUENCE: 8
cacucagugu caaacggacu gguca 25

<210> SEQ ID NO 9
<211> LENGTH: 25
<212> TYPE: RNA
<213> ORGANISM: Artificial
<220> FEATURE:
<223> OTHER INFORMATION: one strand of siRNA[2]

<400> SEQUENCE: 9
uugagaugcc ggaaacauug auggg 25

<210> SEQ ID NO 10
<211> LENGTH: 25
<212> TYPE: RNA
<213> ORGANISM: Artificial
<220> FEATURE:
<223> OTHER INFORMATION: one strand of siRNA[2]

<400> SEQUENCE: 10
cccaucaaug uuuccggcau cucaa 25

<210> SEQ ID NO 11
<211> LENGTH: 25
<212> TYPE: RNA
<213> ORGANISM: Artificial
<220> FEATURE:
<223> OTHER INFORMATION: one strand of siRNA[3]

<400> SEQUENCE: 11
uuaugucucc agcaagcuug gucuu 25

-continued

<210> SEQ ID NO 12
<211> LENGTH: 25
<212> TYPE: RNA
<213> ORGANISM: Artificial
<220> FEATURE:
<223> OTHER INFORMATION: one strand of siRNA[3]

<400> SEQUENCE: 12
aagaccaagc uugcuggaga cauaa 25

<210> SEQ ID NO 13
<211> LENGTH: 25
<212> TYPE: RNA
<213> ORGANISM: Artificial
<220> FEATURE:
<223> OTHER INFORMATION: one strand of siRNA[4]

<400> SEQUENCE: 13
gagacaggag gauguaguuu cuaau 25

<210> SEQ ID NO 14
<211> LENGTH: 25
<212> TYPE: RNA
<213> ORGANISM: Artificial
<220> FEATURE:
<223> OTHER INFORMATION: one strand of siRNA[4]

<400> SEQUENCE: 14
auuagaaacu acauccuccu gucuc 25

<210> SEQ ID NO 15
<211> LENGTH: 25
<212> TYPE: RNA
<213> ORGANISM: Artificial
<220> FEATURE:
<223> OTHER INFORMATION: one strand of control siRNA

<400> SEQUENCE: 15
aagacgaucg uucgggacaa cauaa 25

<210> SEQ ID NO 16
<211> LENGTH: 25
<212> TYPE: RNA
<213> ORGANISM: Artificial
<220> FEATURE:
<223> OTHER INFORMATION: one strand of control siRNA

<400> SEQUENCE: 16
uuauguuguc ccgaacgauc gucuu 25

<210> SEQ ID NO 17
<211> LENGTH: 3710
<212> TYPE: RNA
<213> ORGANISM: Homo sapiens
<220> FEATURE:
<221> NAME/KEY: misc_feature
<223> OTHER INFORMATION: nucleic acid seqeunce of CTBP1-ASc

<400> SEQUENCE: 17
agagcuccuc ccgggcuaca acuggucacu ggcguggucu cuauccgccu cgggcuugac 60
gguuuggcca ggagaagggg cguggggcgg gugggccaca gggggcaggc cgugggacag 120
ggacauggcg cuggggacga uaccuuccac agcagcuggg augccagugg gggccacgcc 180
caccacgccc ggaggguacc ugcugggaga ggguccaucc gugaggccca ccuguaggcg 240

-continued gccuggccag gccccaccug cccuccuagc aucggcagca ccgagggggc cucuccagga 300
ggaccagcag ucagcugcag augucagagg ccgaccugag cacagcccgu uccagcugca 360
gaugugaaac cugaaccugg cagcacggaa gucacaaggg ccgacccaac gcccccaggu 420
agcugcaucu gucccccacug ugacaacagc aagggcuuca ggggaauuug guguucaaag 480
guaugagguu cugucuuguc cagagaguau uuuagauguc cugaguagaa cucagaacac 540
agaaaacgcu gucugggcag acagggcuuc ccccagcagg gcuggcagcc gccgccaugu 600
ggcucgcuga aggcaggguc uugcccaggu gcagauggcu gcugggaggg accugccuga 660
cacccccacc uguaccugcc ccgcagaagu agaguccugu guccccggcu ccacgcaccu 720
gcuugacggu gaagucguug augagguggu gguugugcuc guugaggccg cagugcaggg 780
ucacgcaguc gcuguggaag agcagguccu gcagggugcu gacacgcugc agccccagcg 840
cccgcuccac gccauccgac aaguaagggu cguagaagag cacguugaag ccgaaggccu 900
uggcccgcag cgccacugcc ugccccacgc gaccuggugg cgucaagaca cagugugaga 960
cccuugcuca cccguggccg ggaggccggc cccgaaagcc agggucggag uggccucugu 1020
gccucaguuu gaccaucugc caaggaugac accagcugug gucaagccaa ggugcccacg 1080
cacgcuccac acgagcgcuc cacguccgcu ccaacgcgcc cacugccaag gcggaggaga 1140
ugcacagggg uggaaagggu acacuagccc cucggcccac accagcugcc agccacacca 1200
cuccccugca gccuguccac aggacgugac augaaccacu cagugucaaa cggacugguc 1260
agugggucuc cacccaccca acacaugucc uccgugccca ggccccuccg cuggccuuuc 1320
gauccaccca ucaauguuuc cggcaucuca auuccagcca ccacuacgug gagacggcaa 1380
agggggcagg agggaaacuu ccagaccagg gaggccccgc ugggcucagg uccugacccc 1440
uucgagugga gcggcagaga aagccauccc aggcagacgu gccugccccc accccagcag 1500
uccaaggcug gcacgggucc cagcacagga gccguggagc uugagccacc gugucuggcu 1560
ggggccggcu ccuccucggg gaagggucug cagagugcuc gugcccacug ugagccaaca 1620
gcauggcugc aaaggacaca ggaccccaag cccgcgaacg uggugucucc ugcauugccu 1680
cagagggaac cgcuacacag gaaggaagca gguugagcgc cggggcgggu gggaaguggg 1740
cgcaguuuca aaggcggcag ccagggcagg ccucccugag aagaccaagc uugcuggaga 1800
cauaagggga caggaaggga gccagagagc uggaacaaca cgugcgaggg gcccgcggcg 1860
gccugagggc caaggagacc agaccgccag gcacacaggg uggccggacg uggcccaaac 1920
gcccagggga cccccaguca cucugggaag aggacugggg gaggcuggga ggccagucag 1980
aagagcugag gaccgucuaa acgcacuaca uccuagaaag ggaggcgccu guucuacgag 2040
aaggaacaug guggcuccuu ccauccccag ggacgaggcu gcugcaggag ggaggagggc 2100
ucggcaggcg gaggugggag cagcaguucu gaggguugca gccacggccg gaguacccgg 2160
gcagcucccc aggugcagaa cagcccgucu gucaacgccc ccugccaggg aucccaccaa 2220 augggggagga agagaacaca ggcagacaca gagaaaggcg ucucccacag cgcagaaggc 2280
ggacgacacg cuguuuccca cugcgcacaa cacaaagccc cggaagucgg gcugccggug 2340
gcgaaaacca gcuaaagccg cgggccggcg ccggccacgc cugacacggg agagcagcgg 2400
cuguucgggg cgagaccauu cuucacuucu gucucugcca uucucuucca caugaugucu 2460
ggcuuaggau aagaaauuau gaugaugcag gugaagagac aggaggaugu aguuucuaau 2520
uagaacaaaa cacuggaagc ggacagacgc acagaugacc gaggcuggaa ucagccagca 2580
aaaccucuua auaacuacua uaaacaugcu cagagaugac aacaagugug gauguaaaca 2640

-continued

```
gcagaaaaau ggaggcuucc ggaagaugaa ugguaacucu auaaagaacc acauagaaau   2700

uccagaacga aaacaucccu cugaaacgga acucccugga caaagcuaac ugcaagaaaa   2760

ggaucgggag cuugaaggga ggggcucaaa gucagcagau ggcauccaaa cagaagcaga   2820

gagaaaagaa uuuaaaaaau aaauuuuaaa gaacaggccu ugguggcuga cgccuguaau   2880

cccagcacuc ugggaggcug aggugggcgg aucacaaggu caggaguucg agaccagccu   2940

ggccaacaug gugaaacccc gucucuacua aaaauacaaa aauuagccgg acguggugc    3000

gggcgccugu aguccaagcu acucgggagg cugaggcagg agaauggcgu gaaccuggga   3060

agcagaggcu gcagugagcc gagaucgcgc cacugcacuc cagacugggc gacagagcga   3120

gacuaccuuc cacaaaaaaa aaaaaggcaa cacauuuucg gacaaagaaa agcaaaagga   3180

aucggucacu ggugagccac auuucuaaga cagucuuuag gcuacaggaa cgugacgccc   3240

gaggacagcc agaaucgggg ggcguaaaca aggcagaaag gguggaugug ucgguugaua   3300

uucaaaagaa aaauuacuga aaaauuccuu gacagacuca ugacuaauag cuucuuguac   3360

gguuuucugc auaauagacg uggaaaaucg gcccgagggu gagaggagcc accgcgggcc   3420

ucuggccgcc cuggacgagu cuucacaggu uaugcugggu ggcagugagu uaugaaggcg   3480

uauccuaauc ucuaaaguaa aacuaaacac gaucacuaag cagaguauag guuaaaaagc   3540

aacaacagau gcaaggaauc auuuaacacc ugauuaauau aaaagaaggc cagaaaggaa   3600

aaacaaggau gaacagaaaa cacguagcca gaugacaccg aaauccaaau caucagcaau   3660

uacacuaaaa auaaaugaac ugaacacuca agaggcaaag acugucagac              3710
```

<210> SEQ ID NO 18
<211> LENGTH: 5041
<212> TYPE: RNA
<213> ORGANISM: Homo sapiens
<220> FEATURE:
<221> NAME/KEY: misc_feature
<223> OTHER INFORMATION: nucleic acid seqeunce of CTBP1-ASb

<400> SEQUENCE: 18

```
agagcuccuc ccgggcuaca acuggucacu ggcguggucu cuauccgccu cgggcuugac     60

gguuuggcca ggagaagggg cguggggcgg gugggccaca gggggcaggc cgugggacag    120

ggacauggcg cuggggacga uaccuuccac agcagcuggg augccagugg gggccacgcc    180

caccacgccc ggaggguacc ugcugggaga ggguccaucc gugaggccca ccuguaggcg    240

gccuggccag gccccaccug cccuccuagc aucggcagca ccgagggggc cucuccagga    300

ggaccagcag ucagcugcag augucagagg ccgaccugag cacagcccgu uccagcugca    360

gaugugaaac cugaaccugg cagcacggaa gucacaaggg ccgacccaac gcccccaggu    420

agcugcaucu guccccacug ugacaacagc aagggcuuca ggggaauuug guguucaaag    480

guaugagguu cugucuuguc cagagaguau uuuagauguc cugaguagaa cucagaacac    540

agaaaacgcu gucugggcag acagggcuuc ccccagcagg gcuggcagcc gccgccaugu    600

ggcucgcuga aggcaggguc uugcccaggu gcagauggcu gcugggaggg accugccuga    660

caccccccacc uguaccugcc ccgcagaagu agaguccugu guccccggcu ccacgcaccu    720

gcuugacggu gaagucguug augaggugcu gguugugcuc guugaggccg cagugcaggg    780

ucacgcaguc gcuguggaag agcaggucu gcagggugcu gacacgcugc agccccagcg    840

cccgcuccac gccauccgac aaguaagggu cguagaagag cacguugaag ccgaaggccu    900

uggcccgcag cgccacugcc ugccccacgc gaccuggugg cgucaagaca cagugugaga    960
```

```
cccuugcuca cccguggccg ggaggccggc cccgaaagcc agggucggag uggccucugu   1020
gccucaguuu gaccaucugc caaggaugac accagcugug gucaagccaa ggugcccacg   1080
cacgcuccac acgagcgcuc cacguccgcu ccaacgcgcc cacugccaag gcggaggaga   1140
ugcacagggg uggaaagggu acacuagccc cucggcccac accagcugcc agccacacca   1200
cuccccugca gccuguccac aggacgugac augaaccacu cagugucaaa cggacugguc   1260
agugggucuc cacccaccca acacaugucc uccgugccca ggccccuccg cuggccuuuc   1320
gauccaccca ucaauguuuc cggcaucuca auuccagcca ccacuacgug gagacggcaa   1380
agggggcagg agggaaacuu ccagaccagg gaggccccgc ugggcucagg uccugacccc   1440
uucgagugga gcggcagaga aagccauccc aggcagacgu gccugccccc accccagcag   1500
uccaaggcug gcacgggucc cagcacagga gccguggagc uugagccacc gugucuggcu   1560
ggggccggcu ccuccucggg gaagggucug cagagugcuc gugcccacug ugagccaaca   1620
gcauggcugc aaaggacaca ggaccccaag cccgcgaacg uggugucucc ugcauugccu   1680
cagagggaac cgcuacacag gaaggaagca gguugagcgc cggggcgggu gggaaguggg   1740
cgcaguuuca aaggcggcag ccagggcagg ccucccugag aagaccaagc uugcuggaga   1800
cauaagggga caggaaggga gccagagagc uggaacaaca cgugcgaggg gcccgcggcg   1860
gccugagggc caaggagacc agaccgccag gcacacaggg uggccggacg uggcccaaac   1920
gcccagggga cccccaguca cucugggaag aggacugggg gaggcuggga ggccagucag   1980
aagagcugag gaccgucuaa acgcacuaca uccuagaaag ggaggcgccu guucuacgag   2040
aaggaacaug guggcuccuu ccauccccag ggacgaggcu gcugcaggag ggaggagggc   2100
ucggcaggcg gaggugggag cagcaguucu gaggguugca gccacggccg gaguacccgg   2160
gcagcucccc aggugcagaa cagcccgucu gucaacgccc ccugccaggg aucccaccaa   2220
auggggagga agagaacaca ggcagacaca gagaaaggcg ucucccacag cgcagaaggc   2280
ggacgacacg cuguuuccca cugcgcacaa cacaaagccc cggaagucgg gcugccggug   2340
gcgaaaacca gcuaaagccg cgggccggcg ccggccacgc cugacacggg agagcagcgg   2400
cuguucgggg cgagaccauu cuucacuucu gucucugcca uucucuucca caugaugucu   2460
ggcuuaggau aagaaauuau gaugaugcag gugaagagac aggaggaugu aguuucuaau   2520
uagaacaaaa cacuggaagc ggacagacgc acagaugacc gaggcuggaa ucagccagca   2580
aaaccucuua auaacuacua uaaacaugcu cagagaugac aacaagugug gauguaaaca   2640
gcagaaaaau ggaggcuucc ggaagaugaa ugguaacucu auaaagaacc acauagaaau   2700
uccagaacga aaacaucccu cugaaacgga acucccugga caaagcuaac ugcaagaaaa   2760
ggaucgggag cuugaaggga ggggcucaaa gucagcagau ggcauccaaa cagaagcaga   2820
gagaaaagaa uuuaaaaaau aaauuuuaaa gaacaggccu ugguggcuga cgccuguaau   2880
cccagcacuc ugggaggcug aggugggcgg aucacaaggu caggaguucg agaccagccu   2940
ggccaacaug gugaaacccc gucucuacua aaaauacaaa aauuagccgg acguggugge   3000
gggcgccugu aguccaagcu acucgggagg cugaggcagg agaauggcgu gaaccuggga   3060
agcagaggcu gcagugagcc gagaucgcgc cacugcacuc cagacugggc gacagagcga   3120
gacuaccuuc cacaaaaaaa aaaaaggcaa cacauuuucg gacaaagaaa agcaaaagga   3180
aucggucacu ggugagccac auuucuaaga cagucuuuag gcuacaggaa cgugacgccc   3240
gaggacagcc agaaucgggg ggcguaaaca aggcagaaag gguggaugug ucgguugaua   3300
```

uucaaaagaa aaauuacuga aaaauuccuu gacagacuca ugacuaauag cuucuuguac 3360
gguuuucugc auaauagacg uggaaaaucg gcccgagggu gagaggagcc accgcgggcc 3420
ucuggccgcc cuggacgagu cuucacaggu uaugcugggu ggcagugagu uaugaaggcg 3480
uauccuaauc ucuaaaguaa aacuaaacac gaucacuaag cagaguauag guuaaaaagc 3540
aacaacagau gcaaggaauc auuuaacacc ugauuaauau aaaagaaggc cagaaaggaa 3600
aaacaaggau gaacagaaaa cacguagcca gaugacaccg aaauccaaau caucagcaau 3660
uacacuaaaa auaaaugaac ugaacacuca agaggcaaag acugucagac ugaaaaaaga 3720
aagaggaacu aacucuauac uauuaauaac agacacacuu uaaacauaaa agacagaagu 3780
caggcgccgu ggcucacacc cguaauccca gcacuuuggg aggccaaggc agggugacca 3840
cuugagccca ggaguucuag accauccuga gcaacacagc aagacuuugu cucuaccaaa 3900
aaauaauaau aauaauaaua acaauuaauu uaaaaaaauu gcaguggcac gcaccuauag 3960
uccuaacuac uucggaggcu aaggcaagag gaucucuuga gccccagugc ucaaggcugc 4020
agugagccgu gaccgcacca ccacacucca gcccgaguga cagagcaaga ccuugucucu 4080
gaaugaauga auauaagaac agagauaagc uaaaauuaaa aggaugaaaa aagacauacc 4140
acacaaacac ugaucaaaag agcugggaug gcugccucaa caucagacca auuaauuaga 4200
ccacaaaaag accaacagga aacguccuac uuaauggua aaugucagaa acuuuuucuc 4260
ccacaucaac acgguaacac ccacacucac ugcugcugau gauuguagcu aaugcaaaaa 4320
ggcaaaaaua aagaaauuaa agaaauaaaa gguacagaga ucagaaagga aaauguaaau 4380
cuguguuuau cugcagauga cacagcagug ugugcaagag aaaauucaag agaaucuguu 4440
uuuggcagag gcaggucuca uuacgccauc caggcugguu ucuaacuccu ggugauccuc 4500
cggccucggc cucauaacgc acuaggauaa caggcacaag ccacugcacc cggccuaaca 4560
uggagaauuu agaacgcugu gggauaugag guugguuuac aaaacucaag uguauuucua 4620
ccuacuaaua accaacuguc aagaaacaau uaggccgggc acaguggcuc augccuguaa 4680
ucccaacacu ucgggaggcc aagaugggug gaucacuuga agucaggagu ucgagccugg 4740
ccaacauggc aaaaacuugu cucuacuaaa aauacaaaaa uuagccaggc augguggcgu 4800
gugccuguaa ucccagcuac ucaggaggcu gaggcaggag aauugcuuga acccaggaag 4860
uggagguugc agugagccga gaucaugcca cuguacucca gccuggcaag agagugugac 4920
ucugucucaa aaaaaaaaaa aaaaaggggc agagauugca gugugccgaa aucacgccac 4980
uguacuccag ccugggcgac agagcaagac ugucuccaaa aaaaaaaaaa gaaaaaaaga 5040
a 5041

<210> SEQ ID NO 19
<211> LENGTH: 15756
<212> TYPE: RNA
<213> ORGANISM: Homo sapiens
<220> FEATURE:
<221> NAME/KEY: misc_feature
<223> OTHER INFORMATION: nucleic acid seqeunce of CTBP1-ASa

<400> SEQUENCE: 19
agagcuccuc ccgggcuaca acuggucacu ggcguggucu cuauccgccu cgggcuugac 60
gguuuggcca ggagaagggg cguggggcgg gugggccaca gggggcaggc cgugggacag 120
ggacauggcg cuggggacga uaccuuccac agcagcuggg augccagugg gggccacgcc 180
caccacgccc ggaggguacc ugcugggaga ggguccaucc gugaggccca ccuguaggcg 240

-continued

```
gccuggccag gccccaccug cccuccuagc aucggcagca ccgagggggc cucuccagga    300
ggaccagcag ucagcugcag augucagagg ccgaccugag cacagcccgu uccagcugca    360
gaugugaaac cugaaccugg cagcacggaa gucacaaggg ccgacccaac gcccccaggu    420
agcugcaucu guccccacug ugacaacagc aagggcuuca ggggaauuug guguucaaag    480
guaugagguu cugucuuguc cagagaguau uuuagauguc cugaguagaa cucagaacac    540
agaaaacgcu gucugggcag acagggcuuc ccccagcagg gcuggcagcc gccgccaugu    600
ggcucgcuga aggcaggguc uugcccaggu gcagauggcu gcugggaggg accugccuga    660
cacccccacc uguaccugcc ccgcagaagu agaguccugu guccccggcu ccacgcaccu    720
gcuugacggu gaagucguug augagguggu gguugugcuc guugaggccg cagugcaggg    780
ucacgcaguc gcuguggaag agcagguccu gcagggugcu gacacgcugc agccccagcg    840
cccgcuccac gccauccgac aaguaagggu cguagaagag cacguugaag ccgaaggccu    900
uggcccgcag cgccacugcc ugccccacgc gaccuggugg cgucaagaca cagugugaga    960
cccuugcuca cccguggccg ggaggccggc cccgaaagcc agggucggag uggccucugu   1020
gccucaguuu gaccaucugc caaggaugac accagcugug gucaagccaa ggugcccacg   1080
cacgcuccac acgagcgcuc cacguccgcu ccaacgcgcc cacugccaag gcggaggaga   1140
ugcacagggg uggaaagggu acacuagccc cucggcccac accagcugcc agccacacca   1200
cuccccugca gccuguccac aggacgugac augaaccacu cagugucaaa cggacugguc   1260
agugggucuc cacccaccca acacaugucc uccgugccca ggccccuccg cuggccuuuc   1320
gauccaccca ucaauguuuc cggcaucuca auuccagcca ccacuacgug gagacggcaa   1380
agggggcagg agggaaacuu ccagaccagg gaggccccgc ugggcucagg uccugacccc   1440
uucgagugga gcggcagaga aagccauccc aggcagacgu gccugccccc accccagcag   1500
uccaaggcug gcacgggucc cagcacagga gccguggagc uugagccacc gugucuggcu   1560
ggggccggcu ccuccucggg gaagggucug cagagugcuc gugcccacug ugagccaaca   1620
gcauggcugc aaaggacaca ggaccccaag cccgcgaacg uggugucucc ugcauugccu   1680
cagagggaac cgcuacacag gaaggaagca gguugagcgc cggggcgggu gggaagugggg  1740
cgcaguuuca aaggcggcag ccagggcagg ccucccugag aagaccaagc uugcuggaga   1800
cauaagggga caggaaggga gccagagagc uggaacaaca cgugcgaggg gcccgcggcg   1860
gccugagggc caaggagacc agaccgccag gcacacaggg uggccggacg uggcccaaac   1920
gcccagggga cccccaguca cucugggaag aggacugggg gaggcuggga ggccagucag   1980
aagagcugag gaccgucuaa acgcacuaca uccuagaaag ggaggcgccu guucuacgag   2040
aaggaacaug guggcuccuu ccaucccag ggacgaggcu gcugcaggag ggaggagggc    2100
ucggcaggcg gaggugggag cagcaguucu gaggguugca gccacggccg gaguacccgg   2160
gcagcucccc aggugcagaa cagcccgucu gucaacgccc ccugccaggg aucccaccaa   2220
auggggagga agagaacaca ggcagacaca gagaaaggcg ucucccacag cgcagaaggc   2280
ggacgacacg cuguuuccca cugcgcacaa cacaaagccc cggaagucgg gcugccggug   2340
gcgaaaacca gcuaaagccg cgggccggcg ccggccacgc cugacacggg agagcagcgg   2400
cuguucgggg cgagaccauu cuucacuucu gucucugcca uucucuucca caugaugucu   2460
ggcuuaggau aagaaauuau gaugaugcag gugaagagac aggaggaugu aguuucuaau   2520
uagaacaaaa cacuggaagc ggacagacgc acagaugacc gaggcuggaa ucagccagca   2580
aaaccucuua auaacuacua uaaacaugcu cagagaugac aacaagugug gauguaaaca   2640
```

-continued

```
gcagaaaaau ggaggcuucc ggaagaugaa ugguaacucu auaaagaacc acauagaaau   2700
uccagaacga aaacaucccu cugaaacgga acucccugga caaagcuaac ugcaagaaaa   2760
ggaucgggag cuugaaggga ggggcucaaa gucagcagau ggcauccaaa cagaagcaga   2820
gagaaaagaa uuuaaaaaau aaauuuuaaa gaacaggccu ugguggcuga cgccuguaau   2880
cccagcacuc ugggaggcug aggugggcgg aucacaaggu caggaguucg agaccagccu   2940
ggccaacaug gugaaacccc gucucuacua aaaauacaaa aauuagccgg acguggugge   3000
gggcgccugu aguccaagcu acucgggagg cugaggcagg agaauggcgu gaaccuggga   3060
agcagaggcu gcagugagcc gagaucgcgc cacugcacuc cagacugggc gacagagcga   3120
gacuaccuuc cacaaaaaaa aaaaaggcaa cacauuuucg gacaaagaaa agcaaaagga   3180
aucggucacu ggugagccac auuucuaaga cagucuuuag gcuacaggaa cgugacgccc   3240
gaggacagcc agaaucgggg ggcguaaaca aggcagaaag gguggaugug ucgguugaua   3300
uucaaaagaa aaauuacuga aaaauuccuu gacagacuca ugacuaauag cuucuuguac   3360
gguuuucugc auaauagacg uggaaaaucg gcccgagggu gagaggagcc accgcgggcc   3420
ucuggccgcc cuggacgagu cuucacaggu uaugcugggu ggcagugagu uaugaaggcg   3480
uauccuaauc ucuaaaguaa aacuaaacac gaucacuaag cagaguauag guuaaaaagc   3540
aacaacagau gcaaggaauc auuuaacacc ugauuaauau aaaagaaggc cagaaaggaa   3600
aaacaaggau gaacagaaaa cacguagcca gaugacaccg aaauccaaau caucagcaau   3660
uacacuaaaa auaaaugaac ugaacacuca agaggcaaag acugucagac ugaaaaaaga   3720
aagaggaacu aacucuauac uauuaauaac agacacacuu uaaacauaaa agacagaagu   3780
caggcgccgu ggcucacacc cguaauccca gcacuuuggg aggccaaggc agggugacca   3840
cuugagccca ggaguucuag accauccuga gcaacacagc aagacuuugu cucuaccaaa   3900
aaauaauaau aauaauaaua acaauuaauu uaaaaaaauu gcaguggcac gcaccuauag   3960
uccuaacuac uucggaggcu aaggcaagag gaucucuuga gccccagugc ucaaggcugc   4020
agugagccgu gaccgcacca ccacacucca gcccgaguga cagagcaaga ccuugucucu   4080
gaaugaauga auauaagaac agagauaagc uaaaauuaaa aggaugaaaa aagacauacc   4140
acacaaacac ugaucaaaag agcugggaug gcugccucaa caucagacca auuaauuaga   4200
ccacaaaaag accaacagga aacguccuac uuaaugguga aaugucagaa acuuuuucuc   4260
ccacaucaac acgguaacac ccacacucac ugcugcugau gauuguagcu aaugcaaaaa   4320
ggcaaaaaua aagaaauuaa agaaauaaaa gguacagaga ucagaaagga aaauguaaau   4380
cuguguuuau cugcagauga cacagcagug ugugcaagag aaaauucaag agaaucuguu   4440
uuuggcagag gcaggucuca uuacgccauc caggcugguu ucuaacuccu ggugauccuc   4500
cggccucggc cucauaacgc acuaggauaa caggcacaag ccacugcacc cggccuaaca   4560
uggagaauuu agaacgcugu gggauaugag guugguuuac aaaacucaag uguauuucua   4620
ccuacuaaua accaacuguc aagaaacaau uaggccgggc acaguggcuc augccuguaa   4680
ucccaacacu ucgggaggcc aagaugggug gaucacuuga agucaggagu ucgagccugg   4740
ccaacauggc aaaaacuugu cucuacuaaa aauacaaaaa uuagccaggc augguggcgu   4800
gugccuguaa ucccagcuac ucaggaggcu gaggcaggag aauugcuuga acccaggaag   4860
uggagguugc agugagccga gaucaugcca cuguacucca gccuggcaag agagugugac   4920
ucugucucaa aaaaaaaaaa aaaaaggggc agagauugca gugugccgaa aucacgccac   4980
```

-continued

```
uguacuccag ccugggcgac agagcaagac ugucuccaaa aaaaaaaaaa gaaaaaaaga   5040
auuaaacauu uauaacagca uuacaaaugc caaaugccua acaauaaacu uaaugaacua   5100
cguggaaacc uucuacugau aacgacgaaa caccguuaag aaaaguuaaa auaaauggag   5160
agaucauauu uauguccga agguucaaua uuauuaggaa gucagcauuc ccaaaacuga   5220
uuuuaaggac ucaacaaaau gaaaauugau gagcugauuc cagaauggaa auggaaaugc   5280
acagcaggac cuaaaacagc caagacccuc gucaagaaca ugguggagga ucucaaggcu   5340
cacagccgug cagacagcgu cacaugggag gaaagggaag aaaaacaggu ccacggaaca   5400
gaagagucca gacggaccca cucacaugug gccaacugcc uuuccacaga ggagccaagc   5460
caaccggaag gagggcuccu cggcgcaucg ugccgcagcg accugccauc ccgggaaagg   5520
gugggccacc accccagccu cacaccacgu gugaguggca gcccaggaga cccuggaccu   5580
agagguagaa gcuuccagaa gaaaacacag agaaccuguu acccggauga cccuggggua   5640
aacagauucc ucaggacaca aaagguauuc accuaaaaaa cgggugauac gcugggcuuc   5700
auaaaaacug aaaacguguu cucgucacag agagagguca agaaagugaa aagucaagcc   5760
acggccugag auauucguaa acaagaaaaa acaaaaauuu ugaaauuaug aaaauaucca   5820
caaugcaugu cgaucugaca agaaccugac gcagaccacg ugagggcuuc guaaccaaca   5880
cgaaaaagac ggccggaggu gcuccgagug gccaagggca caaagaggug cucagccucc   5940
ucacuuauca ggaaacuaua gguuaaaauu aaaauaucac aaaauaccug cuggaagggc   6000
uagaauuaca cagagugcug gcaaggauac gcggcugccg gagcaugacg ccgcgccccu   6060
gccugaagaa cagcgacucc uuccaggcga aacaaugucc ugcucuggga cucagaaauu   6120
ccacuccuag guacaaaccc aagagacgug agucuaugug cacaaaaaag acgggcagaa   6180
auguguucac acaaguuuug uuuguaauau uagccaaaaa cuuacaaaau gcaucaccaa   6240
gagucuggag aagcaaaucg ugcuguguuc acgugaugga accguuauca gaaacugcug   6300
ggucguauga aaacacaggu gagacccaga ggcaucaccc cgacugacgg gaggcggaca   6360
cagaaggcug cgugcccgug aucccaccuc ggcacagcug gggaaggccc ucugcucuag   6420
gaagcgggac ccggguccuc gcagggucgu cgcggggccg ccacgggaga agggggcccg   6480
agggagcugu cugugugcag gagccugcuc ugucaacgug cugguggguu caugggguga   6540
auguguacaa uguuuuccug ugugcaccua agacagugca uuuuucagaa ggaaggaagg   6600
aagggaagga gggaggaaag aaagaaacaa gaaggagaug uaagucacgg gcaccagagc   6660
cucguagagc agaggaagcg gccgccccu agucugcgcc gaguggcacc aacaccguga   6720
gccacacgcu gcccagggcu uccacauucc uguagccacc acacacgcgg auuccacgcu   6780
aagaacaacc cagacagugu gugcacagca gagggcagau ggggacaugc acacccuggg   6840
agagccugag uggcuggugc ccagcaccgg ccccgccugg agcaugaggc ucuuccacag   6900
agggugggau ggggcucagg gacaagggcg aggggcgggg cgggggacgg gacgcaggug   6960
uucugcaguc aagggugcca gguggcagc cggggugggg uaggggucc guccacaagg   7020
uagaggcugc agcgucaggg ggcucguguc ccuaaggaca gaacugcucu ccucagcucc   7080
cgaggccgag ggagcgcuga ccuggccugg uucaucacaa gaucaccaca gacagagggg   7140
cccgcgccga gagcgaggga agcagcugcc ccccagcagc uccaggggg ccugcccgag   7200
agcccacagg acgaccuggg ccagugcagg gcagaacgcc caugguaaac ccccacaacc   7260
ugccaggucc acccugcacu ccucaggacg ccggggucc cgcaccugca guccccaccc   7320
acacuccuca ggccaggccu gggcgggggc ccuggcaggu ggggguccuua acgaacgggg   7380
```

-continued uggccacagc ccuacccucu gagggcaucc cgaccugggu guuccaaccc ccacucagca 7440
cggggcccug ggaggggcug guugggccca gcuccacaau cagccuggga aggcgccgcc 7500
cucaggccuc agaguggcca cgggaagagc ccggggccuu cagggccggg accacagacc 7560
ccgaccccag gagagacagg acacaugacu cugggggcaa cacacccacc uacucuuacc 7620
aggggaacua cagacauccc uggccacaca gacacagccc auaccccccc cacaucccac 7680
agucccucgu acaccucagg ugagguguca gaccuguggc ugcaggacag gcggugaccu 7740
gcaggcaagg cacacaugag gcgccuccug uccugugggc uugcucugga gacagcggag 7800
gcaccgcccc cuggacaagg ccagcaggca guccacgaau cugaaggucc acagagcccc 7860
gaguccccgg ccccucccga ccucugcccc aaccugggcu uccugcccac ccucccuccu 7920
ccccucaaca aaccacacau gcgggccaug gcccugacau aggaggggcc gcccaggccu 7980
cagaugggca gaggugugag gaacaggcac cucagggcuc ugggauccuc acaggcucca 8040
gccagcccug ggguccuggu gggggcacca gcaagaccgu gagagacgug uccaggaaga 8100
gacaggcacg uguuccaugc acauccguga accaaccucu cccacuaacc uaggugnggc 8160
cgccucaccg agaccacccg aaacguccga uuccccaaac gcuggcggga caaggacagc 8220
ggucagcagg agugggcugc cuggauguuu gggaagcggg gggccggccg gucaagggga 8280
gucccuggca uggcaaggcc cuugcauccc caugggggccu ccugaggaac ccgcgaucug 8340
gggagacagg cagcugggcc aaggugucca gggagucuuc agaaaaggua caccaccccc 8400
gcccacccuc ucagggagca ccuucccacc ccacaccugg gccccgccca gaugcucccc 8460
cucccucacg gggccccuca ccuggccucu cccagcucua cuuucccuua agacauggcu 8520
cuacucccag gaucucacac acgcacacac acacgugcac aaacaugcac acgcuugccg 8580
cucugagcuc aaccugggcc uggcugugug gggccgguuc accgcugcau gccggaccca 8640
ggacagugcu gggcccagga uaggcggcug caaagcgagu gggcaaauga agagcgaggg 8700
gucgcugaaa ggcaaaccac uccccgggga uagggccagc gccaggggca gcugcuggug 8760
accacggagg aagcccacgg cugcccgaac cccggcccca gcaggaucua cacagccagc 8820
uccaggggac ucaaggggcg agcacaugcu agaccguggu ugaugugcgu gcccacacau 8880
augccgguau cuaucugcgu acgugcccau gacugacauc aaugugugucс caugugaggu 8940
cauguguaug gugugauauc caugugugu gcccaugugu gccaugugau acccgugugu 9000
gugugcugug acaucuguau guccccgugc ggcccaugug ugugcugcga uguccaugug 9060
ugaugucugu gugggggucca cgugugugcu gugaugaccg ugugaugucu augcaggccu 9120
gugugagacc caugugugcu gugugaggcu guguguacug ugacaucugu guguuaucug 9180
ugcgugccca ugaggccugu gugugcugug auguccgugu gugaugucug ugaggcccac 9240
gugugcugug gcgugugaca uccgugcagg cccgugaggc ccacgugugu gcugugacau 9300
ccguguguga ugucugugug ugccacgaug ucuuguguga ggccuguaug ugugcugugg 9360
uguugugugu gacaucugug caggcccugu gugcugugac guccgugcag gccaguguga 9420
gacccauggg uguguuguga uaucugugug aggcugugug cugugacauc uguguuaucu 9480
gugugugccc gugaggucca cgucugugcu gugaugucca ugugugauuu cugugugcgc 9540
ccgugagguc auguauacug ugaugucugu gaggcccaca ugugugcugu ggcaucuaug 9600
acauccgugc aggccaguau guguacugug acaucggugu gugaugucug ugugugccau 9660
gaugucugug ugaggcccac augugugcuc ugauuucugu gugaggcugu guacugugac 9720
auccgugugu uaucuaugug cccaugaagc ccaugugagu gcugugacgu ccgugugugu 9780
uaucugcaug ugcccaugag acccacgugc ugugaugucu gugugaggcu gugugugcug 9840
uggcauccgu guacguuauc ugugugugcc ugugugagac ccacgugugc ugugacgucc 9900
gugcacguag ggcacacgcc ugggacuccc gggcccuggu gccugugcgc acucaguccu 9960
guccuggguu gggaccgaca ccugcagcag ccccaccccg ccccgggccu cuccuccugg 10020
gcacagcuga agagcggcag cgccagacac agggagggac acaggcgugg agcugcggcc 10080
gacgcaccaa guccgaugau gcccaagguc uccccgcgga uccuggcagc gccggacgcc 10140
accucgcgga ucugcucgac gcucuggacu cgugugcccu cccgcagcgc cuggugcagc 10200
cagguggccc gccgguacag guucaggaug uggcacagcg ucgagucggc cgucuccucc 10260
acagacgccg cgggcacguu gcagacggca augccugugg ggacaaggac acggcgguca 10320
cccccgggcc gggcccagcc uccgggagga caccggggcc gccgugacug gagcggguuu 10380
gaagcuuccc aaggaagaag ccaaaggccg uguccccaag gccaccccgg gaggccacga 10440
gaugaacacg uugcucacag gucgggcgca acagagcaac uccaggagcc ccaccuccac 10500
uuuagguuca cguggcagca cacacacggc aacugcucgg ugugugguag ggcugggggug 10560
ugagacgcug cccugacccc ucccgacuca gcgcuggcag cccaggaaga gacaagcacg 10620
ugucuccccg cgucaccucg ccaccccgau uccucucggg gguacccugc ugggaggcug 10680
uggccagguc agaaucuggg ugccggcccc gccugcacac cccuacgugg acauccgcac 10740
auguccucag gccuccccca ggcccagccg ggccccgaag ccccuuccgc ccuccaugcc 10800
ccaccccugc agucgguaac acugaagcug gagccauucc uggaaagcaa guccauccca 10860
uuucucccga guggccaggc acgcccaugu gugaccccua cuccccgcuc ccggccuugu 10920
ccccagagac aggcccuucc ccagccagug ccccucccug agccuauuua cccucauccc 10980
uggcuugucc cuggccaggg ccgccccugc acggcacuuc ccaccccauc cggaugauug 11040
cauuccugug uccgacuggc cauccgucuc ccuggggagg aggagggggc aggaggccag 11100
gacagggcug cauucauagg cccggaagcu ggacaggacc guguggguucc gcaaggggguc 11160
ccgggggccg ggagagggcc ugaugugggg cggcgcaggc aggggcugca uagccccuag 11220
acacaacuca cuuggacgua aaaauguuaa acaagggaga cugagggaga gccaagccag 11280
gcgccacacg agauuggaac aaagaccucc ugagggugg ccagauccca ggggugcccc 11340
agaccauccc uggcugaaga acagagccca ggccugggaa acuccacggg uaacagagau 11400
gguaaacagc agggaccccu caaaaagcac caggcaugca cccgacacca cacacccagg 11460
ccugcacccg acaccgcagc cggcccuucc ugggacgcca ccacagagac aaaggcggga 11520
ggaggcuggc acacagguuu ggcccauggg cgccggcgga agcagcugaa gccagugcag 11580
gagaccccca gauggaggca uggcuuccga caccaccugc guccccccgca ggaacacaga 11640
cgguuccaac uuugcaaugc cauaaacugu auccuaggaa aagggaagca aaaccgugag 11700
gcgcuggcca acugugggca agggcagggu acaaccucgc cuguuaccag caucgagagg 11760
aggagaaaaa acagaccgag ccuggcagaa aacagaaagu gcgcuccaag caggacggcc 11820
aagcaccgcc ccaaguuugu ucuaaugagu gucuguacau ggaugcagac acaugugcau 11880
guuccaugug cguguaggug cacgggugca gacgugcgug uuccaugagu guuccauaug 11940
cugagugcac aagcagaggu gcauguguuc ugugugauga gcaugugauc caugugcuga 12000
gugcgugugc acaggugcag augagugugc gugauccgug ugcugagugc augugcacgg 12060
gugcagauga gugugugugu uccaugugcu gagugcacau gcacggcugc agaugugcgu 12120

```
guucugugug uguucugugu gcugagugug cgugauccgu gugcugagug cgugugcacg  12180
ggugcagaug agugugcagg auccgugugc ugagugcaug ugcacgggug cagaugagug  12240
ugcguguucc augugcugag ugcacaugca uggcugcaga ugugcguguu cugugugcug  12300
agugugcgug auccgugugc ugagugcaug ugcacgggug cagaugagug ugcaagaucc  12360
gugugcuaac ugcaugugca ugggugcaga ugagugugcg uguuccaugu gcugagugca  12420
caugcacgga ugcagaugug cguguuccgu guguguucug ugugcugagu gugcgugauc  12480
caugugcuga gugcacaggu gcagacgugu guguucugug ugcugagugc acacguacug  12540
gguugcaaca cgcugcuguu cccgcugugu cucgggacag agaccuauga gcccuauuac  12600
agccauacac ugacggcccu gcccucaccc ccagggucccc aguacccaag caaggggcac  12660
cagccagaca ugcaugcaga ccugugugaa gccacagcug gauuuccugc ugcccaaaag  12720
agaggaagug cccugagaug aggcucugug aggaacugaa uggcugcaac cucaugccgg  12780
ccccagacgg gaccacgaac caccgccagc cacaccaggc aaugugcaac ggggucccuca  12840
guguggcagu gaagccucca uggacgaagc aagacgggac ggagcuugca ugaaugggca  12900
caggagagaa cucggagccg gccuaccuaa aucccccggcc gacuugaugu cgauguuguc  12960
aaaaccacug ccaauccgga cgaugaugcg gagggcuuug aacuucucca gguccucccu  13020
ggugagagug augguguggu acaucagggc ccccacagcc ucguucagga ccugcagcga  13080
gaaagcacac aggcucagcc cggaaccuga agacccucgg gcuuggccuu cggggguggg  13140
gcugccccgg cugggaaauu agccugugge ccucaggcuu guuccccaag caccagcccg  13200
gacacuggga gaggcuacau gaaggcuucc ccgccacgcg cggccccuca accucugccc  13260
aggcguccug agucccagca auucccaccg cagccuccuc agccgcaugu aggcugcagg  13320
ccggcacugg ucagaguugc ccgcucccca cugugguggc ugagaugucu ccuuuugagc  13380
gugcgcccca ccgagacucu gcucagccuu guggaagaaa cggggucccg ccuggcgagg  13440
acacaggagg gggggugcgg ccacacccag gaaggacacu gagcaggugc agcuggguggg  13500
gguggccagg gaaccugaga ccugcaggcc cggggaugca gguagaaagu gguaagucccc  13560
cgcggcacac aagcacgucg gcggaggcag gcagacgcca cccagccgua aggauacauc  13620
cacaggagca ugcacugccc ccgugucgcc caagaaccug cccagaaaug cugccccugg  13680
cuggcgaggc uugggucuga gcaguguuca caacagucac guuuuuaauu ucagugucca  13740
ugacaacucu uagaccggaa cagcuccccgc gaacaaagac cuggcacaca gcacagcagc  13800
ccaacccugg cgccuccacu cagccaguac auggcaucgc uguggucacg gccaacccca  13860
cccugccaag ggcucccagu uacccccagc ccagggaggg caggggcagu gugggggugca  13920
gaggcacaca gguggaggaa gugcccuagg ccgaagaacc aggugcagca cugggcacag  13980
ggugggggaug ugugugcacc accugcgcau ccacccacac ccaaacacau ccacccgcac  14040
acguccaucc cacacucccg ugcaugacaa cgcccaccca cgggugcaga gaugcucugu  14100
gcgaacagcc guggcugagg acaccaggac augcaggccu cguccacaug ggcauguccg  14160
aguccccgga gacaccagug agccucccau guggacauga cucccaccca ccaccugucc  14220
agcggggccc cagguacucc ugacggauca auggcgcagg cucagcacag agguugccgg  14280
ggccuaggug gcgucuuucc cucccuuccu gccgagcaug gagccuggg aucccgggcg  14340
gcagugccug gguugcugga ccgcagggcg uccugugggga gcugacccug ccugggugccu  14400
gggcagagca gcugguguug ggcaggcaua cgugggcagg gugagggcag cccccaggaa  14460
```

gacgcucacc acccagcugc aaccccuucu ccuacagugc ccggaccucc agcuuagcca 14520
gaacagauga uucccuuuga ggcuggcaca gccucccuuc ccuccugccc accgcagggg 14580
accuagagga gaggaccaug gaggaccaca cagaccaggg ccacagcaga ggcugggcag 14640
caggggaggg gagcccuggg cuagccuggg cauucuccag gaagaaggga agguuggagc 14700
accucggcug caggaggcag ggaggcaucu acccggacca cagaggaaca ggugugugua 14760
acacucauca guucauggac agggcugaug gcugccccgg gccuccuggg agggcuuuga 14820
ggcugcaugc augcagaccc cuggugcacc agacgcagug uggacggggu gaccccuggu 14880
gcaccagaug caguguggac ggggugaacc cuggguguacc acacuugacc agacguagug 14940
uggacggggu gaggccacaa ggacagcaug ggcaggcaga ggccagcagu gggcgacugg 15000
ugcacagcug ugguggaggc gagcggugcg gccaggaaga ccccugcgcu gcguggacug 15060
gagaugggcg cccacacacc aaggaggugc uucgggcagc cuggcaaagc agccgcagcu 15120
aagagagagu caccugcaga ugaagcuucg ucggcaccca cugugggcag gaggggcugc 15180
gcaugcgagc ggugggcaga ggcgcagugg gagaugggcc cuggggucag ggacaggccu 15240
ggugccagac gugagcccgg ggggcuggcc ugggcagcug gaugugcagg ggccacuucc 15300
acagugugug ugcagaggcu cggcauggac aggcuggaca gacccacacc acacaggcuu 15360
guguguacgc aggcaacagc cugcuuucac ccggagcacu ggccacgggc cucgaaaagu 15420
cgauucugaa ccgcggcacg ucaccucccg cacauucgga ggagacagcg aucagauuca 15480
cgugaauaug acgaauauuc auccgcgcag ccuuaagguu gcuuccugca ucggcucuuc 15540
cgugaugaaa aucuaucuca ucuagguaag cucggagaag ccgaagcgug cgccggccaa 15600
gggcccuccu uugggcuccg ggcgcgccca cccagcugag cugugaagcg caagcugccu 15660
ccccgacgag gcuuucauca cuugccugug cacgauucuu aauacacuuu uuucaggucc 15720
uugcccuuuu cccuacugaa uacagguuua acaaca 15756

<210> SEQ ID NO 20
<211> LENGTH: 3189
<212> TYPE: RNA
<213> ORGANISM: Homo sapiens
<220> FEATURE:
<221> NAME/KEY: misc_feature
<223> OTHER INFORMATION: nucleic acid seqeunce of CTBP1-ASd

<400> SEQUENCE: 20
gagagcuccu cccgggccac aacuggucac uggcgugguc ucuauccgcc ucgggcuuga 60
cgguuugacc aggagaaggg gcguggggcg ggugggccac agggggcagg ccgugggaca 120
gggacauggc gcuggggacg auaccuucca cagcagcugg gaugccagug ggggccacgc 180
ccaccacgcc cggaggguac cugcugggag agggguccauc cgugaggccc accuguaggc 240
ggccuggcca ggccccaccu gcccuccuag caucggcagc accgaggggg ccucuccagg 300
aggaccagca gucagggccc cgugcccaug gcacuccugu guccacugag cccugaaggc 360
caccccagcc caggcuccuu ccaagaggcc cugguucuca ugggccuuuc agcugcagau 420
gucagaggcc gaccugagca cagcccuuuc cagcugcaga ugucagaggc cgaccugagc 480
acagcccguu ccagcugcag augugaaacc ugaaccuggc agcacggaag ucacaagggc 540
cgacccaacg cccccagaag uagaguccug uguccccggc uccacgcacc ugcuugacgg 600
ugaagucguu gaugaggugg ugguugugcu cguugaggcc gcagugcagg gucacgcagu 660
cgcuguggaa gagcaggucc ugcagggugc ugacacgcug cagccccagc gcccgcucca 720

-continued

```
cgccauccga caaguaaggg ucguagaaga gcacguugaa gccgaaggcc uuggcccgca    780
gcgccacugc cugccccacg cgaccuggug gcgucaagac acagugugag acccuugcuc    840
acccguggcc gggaggccgg ccccgaaagc cagggucgga guggccucug ugccucaguu    900
ugaccaucug ccaaggauga caccagcugu ggucaagcca aggugcccac gcacgcucca    960
cacgagcgcu ccacguccgc uccaacgcgc ccacugccaa ggcggaggag augcacaggg   1020
guggaaaggg uacacuagcc ccucggccca caccagcugc cagccacacc acucccccugc  1080
agccugucca caggacguga caugaaccac ucagugucaa acggacuggu cagugggucu   1140
ccacccaccc aacacauguc cuccgugccc aggcccccucc gcuggccuuu cgauccaccc  1200
aucaauguuu ccggcaucuc aauuccagcc accacuacgu ggagacggca aagggggcag   1260
gagggaaacu uccagaccag ggaggccccg cugggcucag guccugaccc cuucgagugg   1320
agcggcagag aaagccaucc caggcagacg ugccugcccc caccccagca guccaaggcu   1380
ggcacggguc ccagcacagg agccguggag cuugagccac cgugucuggc uggggccggc   1440
uccuccucgg ggaagggucu gcagagugcu cgugcccacu gugagccaac agcauggcug   1500
caaaggacac aggaccccaa gcccgcgaac guggugucuc cugcauugcc ucagagggaa   1560
ccgcuacaca ggaaggaagc agguugagcg ccggggcggg ugggaagugg gcgcaguuuc   1620
aaaggcggca gccagggcag gccucccuga gaagaccaag cuugcuggag acauaagggg   1680
acaggaaggg agccagagag cuggaacaac acgugcgagg ggcccgcggc ggccugaggg   1740
ccaaggagac cagaccgcca ggcacacagg guggccggac guggcccaaa cgcccagggg   1800
acccccaguc acucugggaa gaggacuggg ggaggcuggg aggccaguca gaagagcuga   1860
ggaccgucua aacgcacuac auccuagaaa gggaggcgcc uguucuacga gaaggaacau   1920
gguggcuccu uccaucccca gggacgaggc ugcugcagga gggaggaggg cucggcaggc   1980
ggagguggga gcagcaguuc ugaggguugc agccacggcc ggaguacccg ggcagcuccc   2040
caggugcaga acagcccguc ugucaacgcc cccugccagg gaucccacca aaugggggagg  2100
aagagaacac aggcagacac agagaaaggc gucucccaca gcgcagaagg cggacgacac   2160
gcuguuuccc acugcgcaca acacaaagcc ccggaagucg ggcugccggu ggcgaaaacc   2220
agcuaaagcc gcgggccggc gccggccacg ccugacacgg gagagcagcg gcuguucggg   2280
gcgagaccau ucuucacuuc ugucucugcc auucucuucc acaugauguc uggcuuagga   2340
uaagaaauua ugaugaugca ggugaagaga caggaggaug uaguuucuaa uuagaacaaa   2400
acacuggaag cggacagacg cacagaugac cgaggcugga aucagccagc aaaaccucuu   2460
aauaacuacu auaaacaugc ucagagauga caacaagugu ggauguaaac agcagaaaaa   2520
uggaggcuuc cggaagauga augguaacuc uauaaagaac cacauagaaa uuccagaacg   2580
aaaacauccc ucugaaacgg aacucccugg acaaagcuaa cugcaagaaa aggaucggga   2640
gcuugaaggg aggggcucaa agucagcaga uggcauccaa acagaagcag agagaaaaga   2700
auuuaaaaaa uaaauuuuaa agaacaggcc uugguggcug acgccuguaa ucccagcacu   2760
cugggaggcu gaggugggcg gaucacaagg ucaggaguuc gagaccagcc uggccaacau   2820
ggugaaaccc cgucucuacu aaaaauacaa aaauuagccg gacgguggug cgggcgccug   2880
uaguccaagc uacucgggag gcugaggcag gagaauggcg ugaaccuggg aagcagaggc   2940
ugcagugagc cgagaucgcg ccacugcacu ccagacuggg cgacagagcg agacuaccuu   3000
ccacaaaaaa aaaaaggcaa cacauuuucg gacaaagaaa agcaaaagga aucggucacu   3060
ggugagccac auuucuaaga cagucuuuag gcuacaggaa cgugacgccc gaggacagcc   3120
```

agaaucgggg ggcguaaaca aggcagaaag gguggaugug ucgguugaua uucaaaagaa 3180
aaauuacug 3189

<210> SEQ ID NO 21
<211> LENGTH: 39
<212> TYPE: DNA
<213> ORGANISM: Artificial sequence
<220> FEATURE:
<223> OTHER INFORMATION: 3' RACE primer used in 3' RACE PCR

<400> SEQUENCE: 21
gaccacgcgt atcgatgtcg actttttttt tttttttv 39

<210> SEQ ID NO 22
<211> LENGTH: 22
<212> TYPE: DNA
<213> ORGANISM: Artificial sequence
<220> FEATURE:
<223> OTHER INFORMATION: PCR adaptor primer used in 3' RACE PCR

<400> SEQUENCE: 22
gaccacgcgt atcgatgtcg ac 22

<210> SEQ ID NO 23
<211> LENGTH: 2230
<212> TYPE: RNA
<213> ORGANISM: Artificial sequence
<220> FEATURE:
<223> OTHER INFORMATION: nucleic acid sequence of the probe used in
nothern blotting of RN A derived from LNCaP cells

<400> SEQUENCE: 23
cugcuugacg gugaagucgu ugaugaggug gugguugugc ucguugaggc cgcagugcag 60
ggucacgcag ucgcugugga agagcagguc cugcagggug cugacacgcu gcagccccag 120
cgcccgcucc acgccauccg acaaguaagg gucguagaag agcacguuga agccgaaggc 180
cuuggcccgc agcgccacug ccugccccac gcgaccuggu ggcgucaaga cacaguguga 240
gacccuugcu cacccguggc cgggaggccg gccccgaaag ccagggucgg aguggccucu 300
gugccucagu uugaccaucu gccaaggaug acaccagcug uggucaagcc aaggugccca 360
cgcacgcucc acacgagcgc uccacguccg cuccaacgcg cccacugcca aggcggagga 420
gaugcacagg gguggaaagg guacacuagc cccucggccc acaccagcug ccagccacac 480
cacuccccug cagccugucc acaggacgug acaugaacca cucaguguca aacggacugg 540 ucagugggguc uccacccacc caacacaugu ccuccgugcc caggccccuc cgcuggccuu 600
ucgauccacc caucaauguu uccggcaucu caauuccagc caccacuacg uggagacggc 660
aaagggggca ggagggaaac uuccagacca gggaggcccc gcugggcuca gguccugacc 720
ccuucgagug gagcggcaga gaaagccauc ccaggcagac gugccugccc ccaccccagc 780
aguccaaggc uggcacgggu cccagcacag gagccgugga gcuugagcca ccgugucugg 840
cuggggccgg cuccuccucg gggaaggguc ugcagagugc ucgugcccac ugugagccaa 900
cagcauggcu gcaaaggaca caggacccca agcccgcgaa cgugguqucu ccugcauugc 960 cucagaggga accgcuacac aggaaggaag cagguugagc gccggggcgg gugggaagug 1020
ggcgcaguuu caaaggcggc agccagggca ggccucccug agaagaccaa gcuugcugga 1080
gacauaaggg gacaggaagg gagccagaga gcuggaacaa cacgugcgag gggcccgcgg 1140
cggccugagg gccaaggaga ccagaccgcc aggcacacag gguggccgga cguggcccaa 1200

-continued acgcccaggg gacccccagu cacucuggga agaggacugg gggaggcugg gaggccaguc 1260
agaagagcug aggaccgucu aaacgcacua cauccuagaa agggaggcgc cuguucuacg 1320
agaaggaaca ugguggcucc uuccaucccc agggacgagg cugcugcagg agggaggagg 1380
gcucggcagg cggaggUggg agcagcaguu cugaggguug cagccacggc cggaguaccc 1440
gggcagcucc ccaggugcag aacagcccgu cugucaacgc ccccugccag ggaucccacc 1500
aaauggggag gaagagaaca caggcagaca cagagaaagg cgucucccac agcgcagaag 1560
gcggacgaca cgcuguuucc cacugcgcac aacacaaagc cccggaaguc gggcugccgg 1620
uggcgaaaac cagcuaaagc cgcgggccgg cgccggccac gccugacacg ggagagcagc 1680
ggcuguucgg ggcgagacca uucuucacuu cugucucugc cauucucuuc cacaugaugu 1740
cuggcuuagg auaagaaauu augaugaugc aggugaagag acaggaggau guaguuucua 1800
auuagaacaa aacacuggaa gcggacagac gcacagauga ccgaggcugg aaucagccag 1860
caaaaccucu uaauaacuac uauaaacaug cucagagaug acaacaagug uggauguaaa 1920
cagcagaaaa auggaggcuu ccggaagaug aaugguaacu cuauaaagaa ccacauagaa 1980
auuccagaac gaaaacaucc cucugaaacg gaacucccug gacaaagcua acugcaagaa 2040
aaggaucggg agcuugaagg gaggggcuca aagucagcag auggcaucca aacagaagca 2100
gagagaaaag aauuuaaaaa auaaaauuua aagaacaggc cuuggguggcu gacgccugua 2160 aucccagcac ucugggaggc ugaggugggc ggaucacaag gucaggaguu cgagaccagc 2220
cuggccaaca 2230

<210> SEQ ID NO 24
<211> LENGTH: 23
<212> TYPE: DNA
<213> ORGANISM: Homo sapiens
<220> FEATURE:
<221> NAME/KEY: misc_feature
<223> OTHER INFORMATION: an example of target region of siRNA against
CTBP1-AS

<400> SEQUENCE: 24
accaacagga aacgtcctac tta 23

<210> SEQ ID NO 25
<211> LENGTH: 23
<212> TYPE: DNA
<213> ORGANISM: Homo sapiens
<220> FEATURE:
<221> NAME/KEY: misc_feature
<223> OTHER INFORMATION: an example of target region of siRNA against
CTBP1-AS

<400> SEQUENCE: 25
ctcaacatca gaccaattaa tta 23

<210> SEQ ID NO 26
<211> LENGTH: 23
<212> TYPE: DNA
<213> ORGANISM: Homo sapiens
<220> FEATURE:
<221> NAME/KEY: misc_feature
<223> OTHER INFORMATION: an example of target region of siRNA against
CTBP1-AS

<400> SEQUENCE: 26
accaactgtc aagaaacaat tag 23

<210> SEQ ID NO 27
<211> LENGTH: 23
<212> TYPE: DNA
<213> ORGANISM: Homo sapiens
<220> FEATURE:
<221> NAME/KEY: misc_feature
<223> OTHER INFORMATION: an example of target region of siRNA against CTBP1-AS

<400> SEQUENCE: 27
ctcactgctg ctgatgattg tag 23

<210> SEQ ID NO 28
<211> LENGTH: 23
<212> TYPE: DNA
<213> ORGANISM: Homo sapiens
<220> FEATURE:
<221> NAME/KEY: misc_feature
<223> OTHER INFORMATION: an example of target region of siRNA against CTBP1-AS

<400> SEQUENCE: 28
gacataccac acaaacactg atc 23

<210> SEQ ID NO 29
<211> LENGTH: 23
<212> TYPE: DNA
<213> ORGANISM: Homo sapiens
<220> FEATURE:
<221> NAME/KEY: misc_feature
<223> OTHER INFORMATION: an example of target region of siRNA against CTBP1-AS

<400> SEQUENCE: 29
gaccaattaa ttagaccaca aaa 23

<210> SEQ ID NO 30
<211> LENGTH: 23
<212> TYPE: DNA
<213> ORGANISM: Homo sapiens
<220> FEATURE:
<221> NAME/KEY: misc_feature
<223> OTHER INFORMATION: an example of target region of siRNA against CTBP1-AS

<400> SEQUENCE: 30
tcccacatca acacggtaac acc 23

<210> SEQ ID NO 31
<211> LENGTH: 23
<212> TYPE: DNA
<213> ORGANISM: Homo sapiens
<220> FEATURE:
<221> NAME/KEY: misc_feature
<223> OTHER INFORMATION: an example of target region of siRNA against CTBP1-AS

<400> SEQUENCE: 31
cacccggcct aacatggaga att 23

<210> SEQ ID NO 32
<211> LENGTH: 23
<212> TYPE: DNA
<213> ORGANISM: Homo sapiens
<220> FEATURE:
<221> NAME/KEY: misc_feature
<223> OTHER INFORMATION: an example of target region of siRNA against CTBP1-AS

<400> SEQUENCE: 32
acccggccta acatggagaa ttt 23

<210> SEQ ID NO 33
<211> LENGTH: 23
<212> TYPE: DNA
<213> ORGANISM: Homo sapiens
<220> FEATURE:
<221> NAME/KEY: misc_feature
<223> OTHER INFORMATION: an example of target region of siRNA against CTBP1-AS

<400> SEQUENCE: 33
ggcctcataa cgcactagga taa 23

<210> SEQ ID NO 34
<211> LENGTH: 23
<212> TYPE: DNA
<213> ORGANISM: Homo sapiens
<220> FEATURE:
<221> NAME/KEY: misc_feature
<223> OTHER INFORMATION: an example of target region of siRNA against CTBP1-AS

<400> SEQUENCE: 34
aacgctgtgg gatatgaggt tgg 23

<210> SEQ ID NO 35
<211> LENGTH: 23
<212> TYPE: DNA
<213> ORGANISM: Homo sapiens
<220> FEATURE:
<221> NAME/KEY: misc_feature
<223> OTHER INFORMATION: an example of target region of siRNA against CTBP1-AS

<400> SEQUENCE: 35
cccggcctaa catggagaat tta 23

<210> SEQ ID NO 36
<211> LENGTH: 23
<212> TYPE: DNA
<213> ORGANISM: Homo sapiens
<220> FEATURE:
<221> NAME/KEY: misc_feature
<223> OTHER INFORMATION: an example of target region of siRNA against CTBP1-AS

<400> SEQUENCE: 36
gcctaacatg gagaatttag aac 23

<210> SEQ ID NO 37
<211> LENGTH: 23
<212> TYPE: DNA
<213> ORGANISM: Homo sapiens
<220> FEATURE:
<221> NAME/KEY: misc_feature
<223> OTHER INFORMATION: an example of target region of siRNA against CTBP1-AS

<400> SEQUENCE: 37
tcctacttaa tggtgaaatg tca 23

<210> SEQ ID NO 38
<211> LENGTH: 23
<212> TYPE: DNA

<213> ORGANISM: Homo sapiens
<220> FEATURE:
<221> NAME/KEY: misc_feature
<223> OTHER INFORMATION: an example of target region of siRNA against CTBP1-AS

<400> SEQUENCE: 38
ctctatacta ttaataacag aca 23

<210> SEQ ID NO 39
<211> LENGTH: 23
<212> TYPE: DNA
<213> ORGANISM: Homo sapiens
<220> FEATURE:
<221> NAME/KEY: misc_feature
<223> OTHER INFORMATION: an example of target region of siRNA against CTBP1-AS

<400> SEQUENCE: 39
gcctcataac gcactaggat aac 23

<210> SEQ ID NO 40
<211> LENGTH: 23
<212> TYPE: DNA
<213> ORGANISM: Homo sapiens
<220> FEATURE:
<221> NAME/KEY: misc_feature
<223> OTHER INFORMATION: an example of target region of siRNA against CTBP1-AS

<400> SEQUENCE: 40
ttctcccaca tcaacacggt aac 23

<210> SEQ ID NO 41
<211> LENGTH: 23
<212> TYPE: DNA
<213> ORGANISM: Homo sapiens
<220> FEATURE:
<221> NAME/KEY: misc_feature
<223> OTHER INFORMATION: an example of target region of siRNA against CTBP1-AS

<400> SEQUENCE: 41
gcctcggcct cataacgcac tag 23

<210> SEQ ID NO 42
<211> LENGTH: 23
<212> TYPE: DNA
<213> ORGANISM: Homo sapiens
<220> FEATURE:
<221> NAME/KEY: misc_feature
<223> OTHER INFORMATION: an example of target region of siRNA against CTBP1-AS

<400> SEQUENCE: 42
tgctgctgat gattgtagct aat 23

<210> SEQ ID NO 43
<211> LENGTH: 23
<212> TYPE: DNA
<213> ORGANISM: Homo sapiens
<220> FEATURE:
<221> NAME/KEY: misc_feature
<223> OTHER INFORMATION: an example of target region of siRNA against CTBP1-AS

<400> SEQUENCE: 43
aggaactaac tctatactat taa 23

<210> SEQ ID NO 44
<211> LENGTH: 23
<212> TYPE: DNA
<213> ORGANISM: Homo sapiens
<220> FEATURE:
<221> NAME/KEY: misc_feature
<223> OTHER INFORMATION: an example of target region of siRNA against CTBP1-AS

<400> SEQUENCE: 44
cactaagcag agtataggtt aaa 23

<210> SEQ ID NO 45
<211> LENGTH: 23
<212> TYPE: DNA
<213> ORGANISM: Homo sapiens
<220> FEATURE:
<221> NAME/KEY: misc_feature
<223> OTHER INFORMATION: an example of target region of siRNA against CTBP1-AS

<400> SEQUENCE: 45
ttaacacctg attaatataa aag 23

<210> SEQ ID NO 46
<211> LENGTH: 23
<212> TYPE: DNA
<213> ORGANISM: Homo sapiens
<220> FEATURE:
<221> NAME/KEY: misc_feature
<223> OTHER INFORMATION: an example of target region of siRNA against CTBP1-AS

<400> SEQUENCE: 46
ttgacacctg attaatataa aag 23

<210> SEQ ID NO 47
<211> LENGTH: 23
<212> TYPE: DNA
<213> ORGANISM: Homo sapiens
<220> FEATURE:
<221> NAME/KEY: misc_feature
<223> OTHER INFORMATION: an example of target region of siRNA against CTBP1-AS

<400> SEQUENCE: 47
tgaacactca agaggcaaag act 23

<210> SEQ ID NO 48
<211> LENGTH: 23
<212> TYPE: DNA
<213> ORGANISM: Homo sapiens
<220> FEATURE:
<221> NAME/KEY: misc_feature
<223> OTHER INFORMATION: an example of target region of siRNA against CTBP1-AS

<400> SEQUENCE: 48
tggacactca agaggcaaag act 23

<210> SEQ ID NO 49
<211> LENGTH: 23
<212> TYPE: DNA
<213> ORGANISM: Homo sapiens
<220> FEATURE:
<221> NAME/KEY: misc_feature
<223> OTHER INFORMATION: an example of target region of siRNA against

CTBP1-AS

<400> SEQUENCE: 49
gaccgtctaa acgcactaca tcc 23

<210> SEQ ID NO 50
<211> LENGTH: 23
<212> TYPE: DNA
<213> ORGANISM: Homo sapiens
<220> FEATURE:
<221> NAME/KEY: misc_feature
<223> OTHER INFORMATION: an example of target region of siRNA against CTBP1-AS

<400> SEQUENCE: 50
cccgcgaacg tggtgtctcc tgc 23

<210> SEQ ID NO 51
<211> LENGTH: 23
<212> TYPE: DNA
<213> ORGANISM: Homo sapiens
<220> FEATURE:
<221> NAME/KEY: misc_feature
<223> OTHER INFORMATION: an example of target region of siRNA against CTBP1-AS

<400> SEQUENCE: 51
tgacaacaag tgtggatgta aac 23

<210> SEQ ID NO 52
<211> LENGTH: 23
<212> TYPE: DNA
<213> ORGANISM: Homo sapiens
<220> FEATURE:
<221> NAME/KEY: misc_feature
<223> OTHER INFORMATION: an example of target region of siRNA against CTBP1-AS

<400> SEQUENCE: 52
tggcaacaag tgtggatgta aac 23

<210> SEQ ID NO 53
<211> LENGTH: 21
<212> TYPE: RNA
<213> ORGANISM: Artificial sequence
<220> FEATURE:
<223> OTHER INFORMATION: sense strand of siRNA No.1

<400> SEQUENCE: 53
caacaggaaa cguccuacuu a 21

<210> SEQ ID NO 54
<211> LENGTH: 21
<212> TYPE: RNA
<213> ORGANISM: Artificial sequence
<220> FEATURE:
<223> OTHER INFORMATION: sense strand of siRNA No.2

<400> SEQUENCE: 54
caacaucaga ccaauuaauu a 21

<210> SEQ ID NO 55
<211> LENGTH: 21
<212> TYPE: RNA
<213> ORGANISM: Artificial sequence
<220> FEATURE:
<223> OTHER INFORMATION: sense strand of siRNA No.3

<400> SEQUENCE: 55
caacugucaa gaaacaauua g 21

<210> SEQ ID NO 56
<211> LENGTH: 21
<212> TYPE: RNA
<213> ORGANISM: Artificial sequence
<220> FEATURE:
<223> OTHER INFORMATION: sense strand of siRNA No.4

<400> SEQUENCE: 56
cacugcugcu gaugauugua g 21

<210> SEQ ID NO 57
<211> LENGTH: 21
<212> TYPE: RNA
<213> ORGANISM: Artificial sequence
<220> FEATURE:
<223> OTHER INFORMATION: sense strand of siRNA No.5

<400> SEQUENCE: 57
cauaccacac aaacacugau c 21

<210> SEQ ID NO 58
<211> LENGTH: 21
<212> TYPE: RNA
<213> ORGANISM: Artificial sequence
<220> FEATURE:
<223> OTHER INFORMATION: sense strand of siRNA No.6

<400> SEQUENCE: 58
ccaauuaauu agaccacaaa a 21

<210> SEQ ID NO 59
<211> LENGTH: 21
<212> TYPE: RNA
<213> ORGANISM: Artificial sequence
<220> FEATURE:
<223> OTHER INFORMATION: sense strand of siRNA No.7

<400> SEQUENCE: 59
ccacaucaac acgguaacac c 21

<210> SEQ ID NO 60
<211> LENGTH: 21
<212> TYPE: RNA
<213> ORGANISM: Artificial sequence
<220> FEATURE:
<223> OTHER INFORMATION: sense strand of siRNA No.8

<400> SEQUENCE: 60
cccggccuaa cauggagaau u 21

<210> SEQ ID NO 61
<211> LENGTH: 21
<212> TYPE: RNA
<213> ORGANISM: Artificial sequence
<220> FEATURE:
<223> OTHER INFORMATION: sense strand of siRNA No.9

<400> SEQUENCE: 61
ccggccuaac auggagaauu u 21

<210> SEQ ID NO 62

<211> LENGTH: 21
<212> TYPE: RNA
<213> ORGANISM: Artificial sequence
<220> FEATURE:
<223> OTHER INFORMATION: sense strand of siRNA No.10

<400> SEQUENCE: 62
ccucauaacg cacuaggaua a 21

<210> SEQ ID NO 63
<211> LENGTH: 21
<212> TYPE: RNA
<213> ORGANISM: Artificial sequence
<220> FEATURE:
<223> OTHER INFORMATION: sense strand of siRNA No.11

<400> SEQUENCE: 63
cgcuguggga uaugagguug g 21

<210> SEQ ID NO 64
<211> LENGTH: 21
<212> TYPE: RNA
<213> ORGANISM: Artificial sequence
<220> FEATURE:
<223> OTHER INFORMATION: sense strand of siRNA No.12

<400> SEQUENCE: 64
cggccuaaca uggagaauuu a 21

<210> SEQ ID NO 65
<211> LENGTH: 21
<212> TYPE: RNA
<213> ORGANISM: Artificial sequence
<220> FEATURE:
<223> OTHER INFORMATION: sense strand of siRNA No.13

<400> SEQUENCE: 65
cuaacaugga gaauuuagaa c 21

<210> SEQ ID NO 66
<211> LENGTH: 21
<212> TYPE: RNA
<213> ORGANISM: Artificial sequence
<220> FEATURE:
<223> OTHER INFORMATION: sense strand of siRNA No.14

<400> SEQUENCE: 66
cuacuuaaug gugaaauguc a 21

<210> SEQ ID NO 67
<211> LENGTH: 21
<212> TYPE: RNA
<213> ORGANISM: Artificial sequence
<220> FEATURE:
<223> OTHER INFORMATION: sense strand of siRNA No.15

<400> SEQUENCE: 67
cuauacuauu aauaacagac a 21

<210> SEQ ID NO 68
<211> LENGTH: 21
<212> TYPE: RNA
<213> ORGANISM: Artificial sequence
<220> FEATURE:
<223> OTHER INFORMATION: sense strand of siRNA No.16

<400> SEQUENCE: 68
cucauaacgc acuaggauaa c 21

<210> SEQ ID NO 69
<211> LENGTH: 21
<212> TYPE: RNA
<213> ORGANISM: Artificial sequence
<220> FEATURE:
<223> OTHER INFORMATION: sense strand of siRNA No.17

<400> SEQUENCE: 69
cucccacauc aacacgguaa c 21

<210> SEQ ID NO 70
<211> LENGTH: 21
<212> TYPE: RNA
<213> ORGANISM: Artificial sequence
<220> FEATURE:
<223> OTHER INFORMATION: sense strand of siRNA No.18

<400> SEQUENCE: 70
cucggccuca uaacgcacua g 21

<210> SEQ ID NO 71
<211> LENGTH: 21
<212> TYPE: RNA
<213> ORGANISM: Artificial sequence
<220> FEATURE:
<223> OTHER INFORMATION: sense strand of siRNA No.19

<400> SEQUENCE: 71
cugcugauga uuguagcuaa u 21

<210> SEQ ID NO 72
<211> LENGTH: 21
<212> TYPE: RNA
<213> ORGANISM: Artificial sequence
<220> FEATURE:
<223> OTHER INFORMATION: sense strand of siRNA No.20

<400> SEQUENCE: 72
gaacuaacuc uauacuauua a 21

<210> SEQ ID NO 73
<211> LENGTH: 21
<212> TYPE: RNA
<213> ORGANISM: Artificial sequence
<220> FEATURE:
<223> OTHER INFORMATION: sense strand of siRNA No.21

<400> SEQUENCE: 73
cuaagcagag uauagguuaa a 21

<210> SEQ ID NO 74
<211> LENGTH: 21
<212> TYPE: RNA
<213> ORGANISM: Artificial sequence
<220> FEATURE:
<223> OTHER INFORMATION: sense strand of siRNA No.22

<400> SEQUENCE: 74
gacaccugau uaauauaaaa g 21

<210> SEQ ID NO 75
<211> LENGTH: 21
<212> TYPE: RNA

<213> ORGANISM: Artificial sequence
<220> FEATURE:
<223> OTHER INFORMATION: sense strand of siRNA No.23

<400> SEQUENCE: 75
gacacucaag aggcaaagac u 21

<210> SEQ ID NO 76
<211> LENGTH: 21
<212> TYPE: RNA
<213> ORGANISM: Artificial sequence
<220> FEATURE:
<223> OTHER INFORMATION: sense strand of siRNA No.24

<400> SEQUENCE: 76
ccgucuaaac gcacuacauc c 21

<210> SEQ ID NO 77
<211> LENGTH: 21
<212> TYPE: RNA
<213> ORGANISM: Artificial sequence
<220> FEATURE:
<223> OTHER INFORMATION: sense strand of siRNA No.25

<400> SEQUENCE: 77
cgcgaacgug gugucuccug c 21

<210> SEQ ID NO 78
<211> LENGTH: 21
<212> TYPE: RNA
<213> ORGANISM: Artificial sequence
<220> FEATURE:
<223> OTHER INFORMATION: sense strand of siRNA No.26

<400> SEQUENCE: 78
gcaacaagug uggauguaaa c 21

<210> SEQ ID NO 79
<211> LENGTH: 21
<212> TYPE: RNA
<213> ORGANISM: Artificial sequence
<220> FEATURE:
<223> OTHER INFORMATION: antisense strand of siRNA No.1

<400> SEQUENCE: 79
aguaggacgu uuccuguugg u 21

<210> SEQ ID NO 80
<211> LENGTH: 21
<212> TYPE: RNA
<213> ORGANISM: Artificial sequence
<220> FEATURE:
<223> OTHER INFORMATION: antisense strand of siRNA No.2

<400> SEQUENCE: 80
auuaauuggu cugauguuga g 21

<210> SEQ ID NO 81
<211> LENGTH: 21
<212> TYPE: RNA
<213> ORGANISM: Artificial sequence
<220> FEATURE:
<223> OTHER INFORMATION: antisense strand of siRNA No.3

<400> SEQUENCE: 81
aauuguuucu ugacaguugg u 21

<210> SEQ ID NO 82
<211> LENGTH: 21
<212> TYPE: RNA
<213> ORGANISM: Artificial sequence
<220> FEATURE:
<223> OTHER INFORMATION: antisense strand of siRNA No.4

<400> SEQUENCE: 82
acaaucauca gcagcaguga g 21

<210> SEQ ID NO 83
<211> LENGTH: 21
<212> TYPE: RNA
<213> ORGANISM: Artificial sequence
<220> FEATURE:
<223> OTHER INFORMATION: antisense strand of siRNA No.5

<400> SEQUENCE: 83
ucaguguuug ugugguaugu c 21

<210> SEQ ID NO 84
<211> LENGTH: 21
<212> TYPE: RNA
<213> ORGANISM: Artificial sequence
<220> FEATURE:
<223> OTHER INFORMATION: antisense strand of siRNA No.6

<400> SEQUENCE: 84
uuguggucua auuaauuggu c 21

<210> SEQ ID NO 85
<211> LENGTH: 21
<212> TYPE: RNA
<213> ORGANISM: Artificial sequence
<220> FEATURE:
<223> OTHER INFORMATION: antisense strand of siRNA No.7

<400> SEQUENCE: 85
uguuaccgug uugauguggg a 21

<210> SEQ ID NO 86
<211> LENGTH: 21
<212> TYPE: RNA
<213> ORGANISM: Artificial sequence
<220> FEATURE:
<223> OTHER INFORMATION: antisense strand of siRNA No.8

<400> SEQUENCE: 86
uucuccaugu uaggccgggu g 21

<210> SEQ ID NO 87
<211> LENGTH: 21
<212> TYPE: RNA
<213> ORGANISM: Artificial sequence
<220> FEATURE:
<223> OTHER INFORMATION: antisense strand of siRNA No.9

<400> SEQUENCE: 87
auucuccaug uuaggccggg u 21

<210> SEQ ID NO 88
<211> LENGTH: 21
<212> TYPE: RNA
<213> ORGANISM: Artificial sequence
<220> FEATURE:

<223> OTHER INFORMATION: antisense strand of siRNA No.10

<400> SEQUENCE: 88
auccuagugc guuaugaggc c 21

<210> SEQ ID NO 89
<211> LENGTH: 21
<212> TYPE: RNA
<213> ORGANISM: Artificial sequence
<220> FEATURE:
<223> OTHER INFORMATION: antisense strand of siRNA No.11

<400> SEQUENCE: 89
aaccucauau cccacagcgu u 21

<210> SEQ ID NO 90
<211> LENGTH: 21
<212> TYPE: RNA
<213> ORGANISM: Artificial sequence
<220> FEATURE:
<223> OTHER INFORMATION: antisense strand of siRNA No.12

<400> SEQUENCE: 90
aauucuccau guuaggccgg g 21

<210> SEQ ID NO 91
<211> LENGTH: 21
<212> TYPE: RNA
<213> ORGANISM: Artificial sequence
<220> FEATURE:
<223> OTHER INFORMATION: antisense strand of siRNA No.13

<400> SEQUENCE: 91
ucuaaauucu ccauguuagg c 21

<210> SEQ ID NO 92
<211> LENGTH: 21
<212> TYPE: RNA
<213> ORGANISM: Artificial sequence
<220> FEATURE:
<223> OTHER INFORMATION: antisense strand of siRNA No.14

<400> SEQUENCE: 92
acauuucacc auuaaguagg a 21

<210> SEQ ID NO 93
<211> LENGTH: 21
<212> TYPE: RNA
<213> ORGANISM: Artificial sequence
<220> FEATURE:
<223> OTHER INFORMATION: antisense strand of siRNA No.15

<400> SEQUENCE: 93
ucuguuauua auaguauaga g 21

<210> SEQ ID NO 94
<211> LENGTH: 21
<212> TYPE: RNA
<213> ORGANISM: Artificial sequence
<220> FEATURE:
<223> OTHER INFORMATION: antisense strand of siRNA No.16

<400> SEQUENCE: 94
uauccuagug cguuaugagg c 21

<210> SEQ ID NO 95
<211> LENGTH: 21
<212> TYPE: RNA
<213> ORGANISM: Artificial sequence
<220> FEATURE:
<223> OTHER INFORMATION: antisense strand of siRNA No.17

<400> SEQUENCE: 95
uaccguguug augugggaga a 21

<210> SEQ ID NO 96
<211> LENGTH: 21
<212> TYPE: RNA
<213> ORGANISM: Artificial sequence
<220> FEATURE:
<223> OTHER INFORMATION: antisense strand of siRNA No.18

<400> SEQUENCE: 96
agugcguuau gaggccgagg c 21

<210> SEQ ID NO 97
<211> LENGTH: 21
<212> TYPE: RNA
<213> ORGANISM: Artificial sequence
<220> FEATURE:
<223> OTHER INFORMATION: antisense strand of siRNA No.19

<400> SEQUENCE: 97
uagcuacaau caucagcagc a 21

<210> SEQ ID NO 98
<211> LENGTH: 21
<212> TYPE: RNA
<213> ORGANISM: Artificial sequence
<220> FEATURE:
<223> OTHER INFORMATION: antisense strand of siRNA No.20

<400> SEQUENCE: 98
aauaguauag aguuaguucc u 21

<210> SEQ ID NO 99
<211> LENGTH: 21
<212> TYPE: RNA
<213> ORGANISM: Artificial sequence
<220> FEATURE:
<223> OTHER INFORMATION: antisense strand of siRNA No.21

<400> SEQUENCE: 99
uaaccuauac ucugcuuagu g 21

<210> SEQ ID NO 100
<211> LENGTH: 21
<212> TYPE: RNA
<213> ORGANISM: Artificial sequence
<220> FEATURE:
<223> OTHER INFORMATION: antisense strand of siRNA No.22

<400> SEQUENCE: 100
uuuauauuaa ucagguguca a 21

<210> SEQ ID NO 101
<211> LENGTH: 21
<212> TYPE: RNA
<213> ORGANISM: Artificial sequence
<220> FEATURE:
<223> OTHER INFORMATION: antisense strand of siRNA No.23

<400> SEQUENCE: 101
ucuuugccuc uugagugucc a 21

<210> SEQ ID NO 102
<211> LENGTH: 21
<212> TYPE: RNA
<213> ORGANISM: Artificial sequence
<220> FEATURE:
<223> OTHER INFORMATION: antisense strand of siRNA No.24

<400> SEQUENCE: 102
auguagugcg uuuagacggu c 21

<210> SEQ ID NO 103
<211> LENGTH: 21
<212> TYPE: RNA
<213> ORGANISM: Artificial sequence
<220> FEATURE:
<223> OTHER INFORMATION: antisense strand of siRNA No.25

<400> SEQUENCE: 103
aggagacacc acguucgcgg g 21

<210> SEQ ID NO 104
<211> LENGTH: 21
<212> TYPE: RNA
<213> ORGANISM: Artificial sequence
<220> FEATURE:
<223> OTHER INFORMATION: antisense strand of siRNA No.26

<400> SEQUENCE: 104
uuacauccac acuuguugcc a 21

<210> SEQ ID NO 105
<211> LENGTH: 19
<212> TYPE: DNA
<213> ORGANISM: Artificial sequence
<220> FEATURE:
<223> OTHER INFORMATION: Forward primer used for Real-time PCR directed
to CTBP1

<400> SEQUENCE: 105
ggacgcctgt atggaagca 19

<210> SEQ ID NO 106
<211> LENGTH: 17
<212> TYPE: DNA
<213> ORGANISM: Artificial sequence
<220> FEATURE:
<223> OTHER INFORMATION: Reverse primer used for Real-time PCR directed
to CTBP1

<400> SEQUENCE: 106
tccgcagacg ccttttg 17

<210> SEQ ID NO 107
<211> LENGTH: 24
<212> TYPE: DNA
<213> ORGANISM: Artificial sequence
<220> FEATURE:
<223> OTHER INFORMATION: Forward primer used for Real-time PCR directed
to CTBP1-ARBS

<400> SEQUENCE: 107
gcactgtgtg gcataaaaag aaaa 24

```
<210> SEQ ID NO 108
<211> LENGTH: 17
<212> TYPE: DNA
<213> ORGANISM: Artificial sequence
<220> FEATURE:
<223> OTHER INFORMATION: Reverse primer used for Real-time PCR directed
      to CTBP1-ARBS

<400> SEQUENCE: 108

tggaacgtgc cccagaa                                                  17


<210> SEQ ID NO 109
<211> LENGTH: 18
<212> TYPE: DNA
<213> ORGANISM: Artificial sequence
<220> FEATURE:
<223> OTHER INFORMATION: Forward primer used for Real-time RT-PCR
      directed to CTBP1

<400> SEQUENCE: 109

tggccactgt ggccttct                                                 18


<210> SEQ ID NO 110
<211> LENGTH: 21
<212> TYPE: DNA
<213> ORGANISM: Artificial sequence
<220> FEATURE:
<223> OTHER INFORMATION: Reverse primer used for Real-time RT-PCR
      directed to CTBP1

<400> SEQUENCE: 110

cgttcaggac cttctcatgg a                                             21


<210> SEQ ID NO 111
<211> LENGTH: 19
<212> TYPE: DNA
<213> ORGANISM: Artificial sequence
<220> FEATURE:
<223> OTHER INFORMATION: Forward primer used for Real-time RT-PCR
      directed to CTBP1-AS

<400> SEQUENCE: 111

aacctggcag cacggaagt                                                19


<210> SEQ ID NO 112
<211> LENGTH: 21
<212> TYPE: DNA
<213> ORGANISM: Artificial sequence
<220> FEATURE:
<223> OTHER INFORMATION: Reverse primer used for Real-time RT-PCR
      directed to CTBP1-AS

<400> SEQUENCE: 112

gagcacaacc accacctcat c                                             21


<210> SEQ ID NO 113
<211> LENGTH: 22
<212> TYPE: DNA
<213> ORGANISM: Artificial sequence
<220> FEATURE:
<223> OTHER INFORMATION: Forward primer used for Real-time RT-PCR
      directed to TMPRSS2

<400> SEQUENCE: 113

tcaacccctc taactggtgt ga                                            22
```

```
<210> SEQ ID NO 114
<211> LENGTH: 20
<212> TYPE: DNA
<213> ORGANISM: Artificial sequence
<220> FEATURE:
<223> OTHER INFORMATION: Reverse primer used for Real-time RT-PCR
      directed to TMPRSS2

<400> SEQUENCE: 114

aggcgaacac accgattctc                                              20


<210> SEQ ID NO 115
<211> LENGTH: 20
<212> TYPE: DNA
<213> ORGANISM: Artificial sequence
<220> FEATURE:
<223> OTHER INFORMATION: Forward primer used for Real-time RT-PCR
      directed to SMAD3

<400> SEQUENCE: 115

ccccagagca atattccaga                                              20


<210> SEQ ID NO 116
<211> LENGTH: 20
<212> TYPE: DNA
<213> ORGANISM: Artificial sequence
<220> FEATURE:
<223> OTHER INFORMATION: Reverse primer used for Real-time RT-PCR
      directed to SMAD3

<400> SEQUENCE: 116

ggctcgcagt aggtaactgg                                              20


<210> SEQ ID NO 117
<211> LENGTH: 20
<212> TYPE: DNA
<213> ORGANISM: Artificial sequence
<220> FEATURE:
<223> OTHER INFORMATION: Forward primer used for Real-time RT-PCR
      directed to p53

<400> SEQUENCE: 117

cccctctgag tcaggaaaca                                              20


<210> SEQ ID NO 118
<211> LENGTH: 20
<212> TYPE: DNA
<213> ORGANISM: Artificial sequence
<220> FEATURE:
<223> OTHER INFORMATION: Reverse primer used for Real-time RT-PCR
      directed to p53

<400> SEQUENCE: 118

tcatctggac ctgggtcttc                                              20


<210> SEQ ID NO 119
<211> LENGTH: 21
<212> TYPE: DNA
<213> ORGANISM: Artificial sequence
<220> FEATURE:
<223> OTHER INFORMATION: Sense strand of siPSF#1.

<400> SEQUENCE: 119

gcacguuuga guacgaauau u                                            21


<210> SEQ ID NO 120
<211> LENGTH: 21
```

<212> TYPE: DNA
<213> ORGANISM: Artificial sequence
<220> FEATURE:
<223> OTHER INFORMATION: Sense strand of siPSF#2.

<400> SEQUENCE: 120
ggcacguuug aguacgaaua u 21

<210> SEQ ID NO 121
<211> LENGTH: 21
<212> TYPE: DNA
<213> ORGANISM: Artificial sequence
<220> FEATURE:
<223> OTHER INFORMATION: Sense strand of siPSF#3.

<400> SEQUENCE: 121
gcauauuagg cuacguauuc c 21

<210> SEQ ID NO 122
<211> LENGTH: 21
<212> TYPE: DNA
<213> ORGANISM: Artificial sequence
<220> FEATURE:
<223> OTHER INFORMATION: Sense strand of siPSF#4.

<400> SEQUENCE: 122
gaugaucgug gaagaucuac a 21

<210> SEQ ID NO 123
<211> LENGTH: 21
<212> TYPE: DNA
<213> ORGANISM: Artificial sequence
<220> FEATURE:
<223> OTHER INFORMATION: Sense strand of siPSF#5.

<400> SEQUENCE: 123
gggagauccc uaugguucag g 21

<210> SEQ ID NO 124
<211> LENGTH: 21
<212> TYPE: DNA
<213> ORGANISM: Artificial sequence
<220> FEATURE:
<223> OTHER INFORMATION: Sense strand of siPSF#6.

<400> SEQUENCE: 124
guuugggcag guaaaauuau g 21

<210> SEQ ID NO 125
<211> LENGTH: 21
<212> TYPE: DNA
<213> ORGANISM: Artificial sequence
<220> FEATURE:
<223> OTHER INFORMATION: Sense strand of siPSF#7.

<400> SEQUENCE: 125
cauagguuau gaagcuaauc c 21

<210> SEQ ID NO 126
<211> LENGTH: 21
<212> TYPE: DNA
<213> ORGANISM: Artificial sequence
<220> FEATURE:
<223> OTHER INFORMATION: Sense strand of siPSF#8.

<400> SEQUENCE: 126
ggcauagguu augaagcuaa u 21

<210> SEQ ID NO 127
<211> LENGTH: 21
<212> TYPE: DNA
<213> ORGANISM: Artificial sequence
<220> FEATURE:
<223> OTHER INFORMATION: Antisense strand of siPSF#1.

<400> SEQUENCE: 127
uauucguacu caaacgugcc a 21

<210> SEQ ID NO 128
<211> LENGTH: 21
<212> TYPE: DNA
<213> ORGANISM: Artificial sequence
<220> FEATURE:
<223> OTHER INFORMATION: Antisense strand of siPSF#2.

<400> SEQUENCE: 128
auucguacuc aaacgugcca u 21

<210> SEQ ID NO 129
<211> LENGTH: 21
<212> TYPE: DNA
<213> ORGANISM: Artificial sequence
<220> FEATURE:
<223> OTHER INFORMATION: Antisense strand of siPSF#3.

<400> SEQUENCE: 129
aauacguagc cuaauaugca u 21

<210> SEQ ID NO 130
<211> LENGTH: 21
<212> TYPE: DNA
<213> ORGANISM: Artificial sequence
<220> FEATURE:
<223> OTHER INFORMATION: Antisense strand of siPSF#4.

<400> SEQUENCE: 130
uagaucuucc acgaucaucc a 21

<210> SEQ ID NO 131
<211> LENGTH: 21
<212> TYPE: DNA
<213> ORGANISM: Artificial sequence
<220> FEATURE:
<223> OTHER INFORMATION: Antisense strand of siPSF#5.

<400> SEQUENCE: 131
ugaaccauag ggaucuccca u 21

<210> SEQ ID NO 132
<211> LENGTH: 21
<212> TYPE: DNA
<213> ORGANISM: Artificial sequence
<220> FEATURE:
<223> OTHER INFORMATION: Antisense strand of siPSF#6.

<400> SEQUENCE: 132
uaauuuuacc ugcccaaaca g 21

<210> SEQ ID NO 133
<211> LENGTH: 21
<212> TYPE: DNA
<213> ORGANISM: Artificial sequence -continued

```
<220> FEATURE:
<223> OTHER INFORMATION: Antisense strand of siPSF#7.

<400> SEQUENCE: 133

auuagcuuca uaaccuaugc c                                         21


<210> SEQ ID NO 134
<211> LENGTH: 21
<212> TYPE: DNA
<213> ORGANISM: Artificial sequence
<220> FEATURE:
<223> OTHER INFORMATION: Antisense strand of siPSF#8.

<400> SEQUENCE: 134

uagcuucaua accuaugcca c                                         21
```